United States Patent
Chen et al.

(10) Patent No.: US 11,787,858 B2
(45) Date of Patent: Oct. 17, 2023

(54) ANTI-LILRB3 ANTIBODIES AND METHODS OF USE THEREOF

(71) Applicant: Icahn School of Medicine at Mount Sinai, New York, NY (US)

(72) Inventors: Shu-Hsia Chen, New York, NY (US); Ping-Ying Pan, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 563 days.

(21) Appl. No.: 16/471,395

(22) PCT Filed: Dec. 22, 2017

(86) PCT No.: PCT/US2017/068270
§ 371 (c)(1),
(2) Date: Jun. 19, 2019

(87) PCT Pub. No.: WO2018/119425
PCT Pub. Date: Jun. 28, 2018

(65) Prior Publication Data
US 2020/0071398 A1    Mar. 5, 2020

Related U.S. Application Data

(60) Provisional application No. 62/437,972, filed on Dec. 22, 2016.

(51) Int. Cl.
| | |
|---|---|
| *C07K 16/28* | (2006.01) |
| *A61P 35/00* | (2006.01) |
| *C07K 16/30* | (2006.01) |
| *C12N 5/12* | (2006.01) |
| *A61K 39/00* | (2006.01) |

(52) U.S. Cl.
CPC .......... *C07K 16/2803* (2013.01); *A61P 35/00* (2018.01); *C07K 16/30* (2013.01); *C12N 5/12* (2013.01); *A61K 2039/505* (2013.01); *C07K 2317/565* (2013.01); *C07K 2317/75* (2013.01); *C07K 2317/76* (2013.01)

(58) Field of Classification Search
CPC ................ C07K 16/2803; C07K 16/30; C07K 2317/565; C07K 2317/75; C07K 2317/76; C07K 2317/70; C07K 2317/73; A61P 35/00; C12N 5/12; A61K 2039/505
See application file for complete search history.

(56) References Cited

U.S. PATENT DOCUMENTS

| | | |
|---|---|---|
| 2011/0256154 A1 | 10/2011 | Vincent et al. |
| 2013/0039974 A1 | 2/2013 | Kufe et al. |
| 2015/0174203 A1 | 6/2015 | Chen et al. |

FOREIGN PATENT DOCUMENTS

| | | | |
|---|---|---|---|
| WO | 2009/012944 A1 | 1/2009 | |
| WO | 2011091177 A1 | 7/2011 | |
| WO | 2011091181 A1 | 7/2011 | |
| WO | 2011/106528 A1 | 9/2011 | |
| WO | WO-2013071058 A1 * | 5/2013 | ........... A61K 31/517 |
| WO | 2013/117647 A1 | 8/2013 | |
| WO | 2016127247 A1 | 8/2016 | |
| WO | 2016/139297 A1 | 9/2016 | |
| WO | WO-2017156298 A1 * | 9/2017 | ....... A61K 39/39566 |

OTHER PUBLICATIONS

Chinese Office Action dated Jan. 12, 2023, in Chinese Application No. 201780087114.6, 7 pages.
Canadian Office Action dated Feb. 9, 2023, in Canadian Application No. 3047833, 4 pages.

* cited by examiner

*Primary Examiner* — Julie Wu
*Assistant Examiner* — John L Van Druff
(74) *Attorney, Agent, or Firm* — Fox Rothschild LLP

(57) ABSTRACT

Antibodies and antibody fragments that specifically bind to LILRB3 are disclosed. Also provided herein are compositions comprising antibodies and antibody fragments that specifically bind to LILRB3 and methods of use thereof.

9 Claims, 16 Drawing Sheets
Specification includes a Sequence Listing.

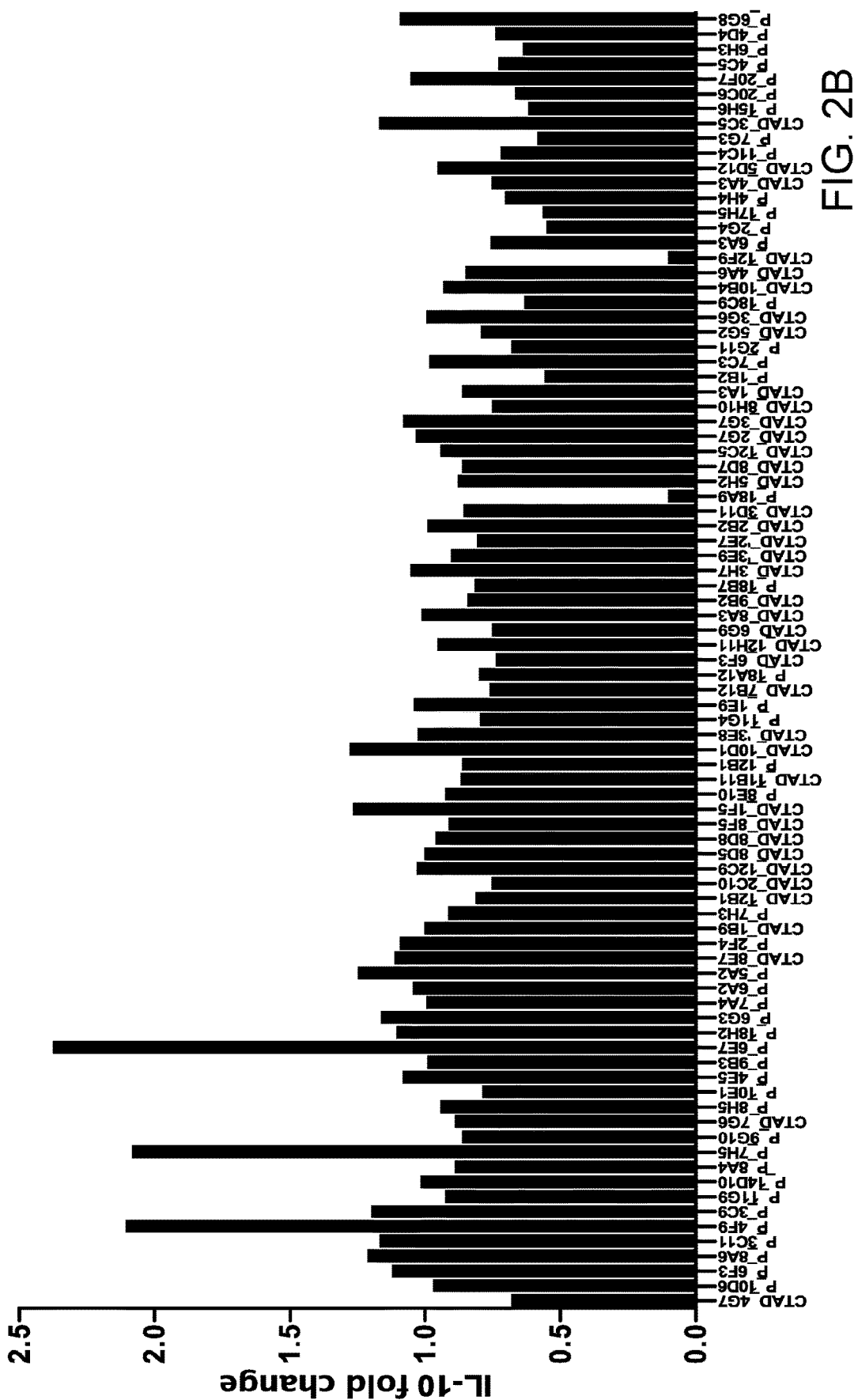

ANTI-LILRB3 ANTIBODIES AND METHODS OF USE THEREOF

CROSS-REFERENCE TO RELATED APPLICATIONS

This application is the U.S. National Application under 35 U.S.C. § 371 of International Patent Application No. PCT/US2017/068270, filed Dec. 22, 2017, which claims the benefit of priority of U.S. Provisional Application No. 62/437,972, filed Dec. 22, 2016, the entire content of each of which are hereby incorporated by reference.

FEDERALLY SPONSORED RESEARCH OR DEVELOPMENT

This invention was made with Government support under Grant Nos. CA109322 and CA127483 awarded by the National Institutes of Health. The Government has certain rights in the invention.

TECHNICAL FIELD

This invention relates generally to antibodies or antigen-binding fragments thereof that bind to modulate leukocyte immunoglobulin (Ig)-like receptor (LILR) B3 (LILRB3) ("anti-LLIRB3 antibodies") and modulate LLIRB3 signaling to induce acquisition of either the M1 or the M2 functional phenotype in myeloid cells, compositions comprising anti-LLIRB3 antibodies, and uses thereof.

BACKGROUND

Leukocyte immunoglobulin (Ig)-like receptor (LILR), also known as immunoglobulin like transcripts (ILTs), are a family of inhibitory and stimulatory cell surface receptors encoded within the leukocyte receptor complex and are expressed by immune cell types of both myeloid and lymphoid lineage. ILTs influence both innate and acquired immune systems and demonstrate wide-ranging effects of LILR signaling on immune cell activity. The inhibitory activities of inhibitory receptors (LILRBs) occur upon co-crosslinking with activating receptors.

Myeloid-derived suppressor cells (MDSCs) are myeloid progenitors with immune suppressive functions that have included Gr1+CD11b+CD115+Ly6C+ monocytic (M)-cells and Gr1+CD11b+Ly6G+ granulocytic (G)-cells in mice (Gabrilovich et al., Cancer Res. 67:425, 2007; Huang et al., Cancer Res. 66:1123-1131, 2006). Human MDSCs are characterized as CD33+CD14+CD16+, CD11b+CD14LowCD33+ or Lin−HLA−DRLow−CD33+ myeloid cells (Chen et. al., Clin. Cancer Res., 21(18):4073-2742, 2015; Ostrand-Rosenberg et al., J. Immunol. 182:4499-4506, 2009; Raychaudhuri et al., Neuro. Oncol. 13:591-599, 2011). In recent years, MDSCs have been found to play an important role in the regulation of the immune response in infection, malignancy, transplantation, and other immune disorders (e.g., Yin et al., J. Immunol. 185:5828-5834, 2010).

MDSCs can be differentiated and polarized into M1- and M2-linage cells (M1-cells expressing iNOS, TNF-α, IFN-gR, MHC class I, and CCR7, and M2-cells expressing arginase, IL-10, CD36, CD206, CD163, PD-L1, DC-SIGN and CCR2). M2-cells possess an enhanced ability to suppress Teff activation and proliferation compared to their M1-like counterparts in co-cultures of T-cells and in vivo (Ma et al., Immunity 34:385-395, 2011). M2-cells also possess higher potency in Treg expansion than those with an M1 phenotype, both in vitro and in vivo (Ma et al., Immunity 34:385-395, 2011). As M2-cells suppress Teff activation and proliferation, and promote Treg expansion, M2-cells can be used to treat autoimmune diseases, where a decrease in pro-inflammatory immune response is desired.

M1-cells have increased direct tumor killing and promote the development of anti-tumoral immunity through the augmentation of free radicals, death ligand, HLA-DR and immunostimulating cytokines-TNFa, (see, e.g., Ma et al., Immunity 34:385-395, 2011), and therefore, M1-cells can be used to treat cancer or other disorders where an increase in pro-inflammatory immune response is desired.

SUMMARY

The present disclosure features antibodies and antigen-binding fragments thereof that bind to leukocyte immunoglobulin (Ig)-like receptor B3 ("LILRB3"), e.g., an anti-LILRB3 antibody or antigen-binding fragments thereof. These antibodies can be grouped into two classes: a first class (Class I) includes LILRB3 antagonist antibodies and antigen-binding fragments thereof for use in the treatment of cancer; and a second class (Class II) including LILRB3 agonist antibodies and antigen-binding fragments thereof for use in the treatment in immune suppression.

In one aspect, the disclosure provides an antibody or antigen-binding fragment thereof that specifically binds to LILRB3, wherein the antibody or antigen-binding fragment comprises a heavy chain complementarity determining region (CDR) 1 comprising an amino acid sequence as set forth in one of SEQ ID NOs: 44-52, 54-55, 57-58, or the amino acid sequence as set forth in one of SEQ ID NOs: 44-52, 54-55, 57-58 with a substitution at two or fewer amino acid positions, a heavy chain CDR 2 comprising an amino acid sequence as set forth in one of SEQ ID NOs: 59-70, or the amino acid sequence as set forth in one of SEQ ID NOs: 59-70 with a substitution at two or fewer amino acid positions, and a heavy chain CDR 3 comprising an amino acid sequence as set forth in one of SEQ ID NOs: 71-86, or the amino acid sequence as set forth in one of SEQ ID NOs: 71-86 with a substitution at two or fewer amino acid positions.

In one aspect, the disclosure provides an antibody or antigen-binding fragment thereof that specifically binds to LILRB3, wherein the antibody or antigen-binding fragment comprises a light chain CDR 1 comprising an amino acid sequence as set forth in one of SEQ ID NOs: 1-17, or the amino acid sequence as set forth in one of SEQ ID NOs: 1-17 with a substitution at two or fewer amino acid positions, a light chain CDR 2 comprising an amino acid sequence as set forth in one of SEQ ID NOs: 18-26, or the amino acid sequence as set forth in one of SEQ ID NOs: 18-26 with a substitution at two or fewer amino acid positions, and a light chain CDR 3 comprising an amino acid sequence as set forth in one of SEQ ID NOs: 27-43, or the amino acid sequence as set forth in one of SEQ ID NOs: 27-43 with a substitution at two or fewer amino acid positions.

In one aspect, the disclosure provides an antibody or antigen-binding fragment thereof specifically binds to LILRB3, wherein the antibody or antigen-binding fragment thereof comprises a heavy chain variable region comprising complementarity determining region CDR1, CDR2, and CDR3, consisting of the amino acid sequences: (i) GYTFT-TYG (SEQ ID NO: 44), MNTYSGVP (SEQ ID NO: 59), and CARMGRGSLYGMDYW (SEQ ID NO: 71), respectively; (ii) GYTFTTYG (SEQ ID NO: 44), INTYSGVP (SEQ ID NO: 60) and CARSGHSYSLYVMGYW (SEQ ID NO: 72), respectively; (iii) GYTFTTYG (SEQ ID NO: 44), INTYSGVP (SEQ ID NO: 60) and CARSGHNYSLYVMGYW (SEQ ID NO: 73), respectively; (iv) GYTFTTYG (SEQ ID NO: 44), INTYSGVP (SEQ ID NO: 60) and CARGALYYFDNW (SEQ ID NO: 74), respectively; (v) GYMFTTYG (SEQ ID NO: 45), INTYSGVP (SEQ ID NO: 60) and CARIGNTNSLYTVHYW (SEQ ID NO: 75), respectively; (vi) GYTFTTYG (SEQ ID NO: 44), INTYSGVP (SEQ ID NO: 60) and CARIGNTNSLYTVHYW (SEQ ID NO: 75), respectively; (vii) GYTFTNYG (SEQ ID NO: 46), INTYSGVP (SEQ ID NO: 60) and CARIGNTNSLYTVHYW (SEQ ID NO: 75), respectively; (viii) GYTFTTYG (SEQ ID NO: 44), INTYSGVP (SEQ ID NO: 60) and CTRIGNTNSLYTVHYW (SEQ ID NO: 76), respectively; (ix) GYSITSGHY (SEQ ID NO: 47), ISYDGNN (SEQ ID NO: 61) and CVRGYYYYGSRAMDYW (SEQ ID NO: 77), respectively; (x) GYSITSGHY (SEQ ID NO: 47), ISYDGND (SEQ ID NO: 62) and CVRGYYYYGSRAMDCW (SEQ ID NO: 78), respectively; (xi) GFSFSDYG (SEQ ID NO: 48), ISSGSSTI (SEQ ID NO: 63) and CGPSDYWYFDVW (SEQ ID NO: 79), respectively; (xii) GFTFSDYG (SEQ ID NO: 49), ISSGSSTI (SEQ ID NO: 63) and CARDYFYGNNYGFPYW (SEQ ID NO: 80), respectively; (xiii) GYTFINYY (SEQ ID NO: 50), IYPGNINS (SEQ ID NO: 64) and CAMTNSSAMDYW (SEQ ID NO: 81), respectively; (xiv) GYTFISYY (SEQ ID NO: 51), IYPGNVNT (SEQ ID NO: 65) and CAMTNSSAMDYW (SEQ ID NO: 81), respectively; (xv) GYTFTSYY (SEQ ID NO: 52), IYPGNVNT (SEQ ID NO: 65) and CAMTNSSAMDYW (SEQ ID NO: 81), respectively; (xvi) GFSLTNYD (SEQ ID NO: 54), IWTGGNT (SEQ ID NO: 66) and CVREGFRQGYYAMDYW (SEQ ID NO: 82), respectively; (xvii) GYTFTDYY (SEQ ID NO: 55), IDTKNGGT (SEQ ID NO: 67) and CASGGRGYW (SEQ ID NO: 83), respectively; (xviii) GYTFTNYG (SEQ ID NO: 46), INTYTGEP (SEQ ID NO: 68) and CTRNYYRPYYYAMDYW (SEQ ID NO: 84), respectively; (xix) GYSFTGYT (SEQ ID NO: 57), INPYNDNT (SEQ ID NO: 69) and CAREGNYYGASPWFAYW (SEQ ID NO: 85), respectively; and (xx) GYTFTHYG (SEQ ID NO: 58), INTSTGET (SEQ ID NO: 70) and CARYYYGSSRWRDYWFAYW (SEQ ID NO: 86), respectively.

In one aspect, the disclosure provides an antibody or antigen-binding fragment thereof specifically binds to LILRB3, wherein the antibody or antigen-binding fragment thereof comprises a heavy chain variable region comprising complementarity determining region (CDR)1, CDR2, and CDR3, consisting of the amino acid sequences: consisting of the amino acid sequences: (i) GYTFTTYG (SEQ ID NO: 44), MNTYSGVP (SEQ ID NO: 59), and CARMGRGSLYGMDYW (SEQ ID NO: 71), respectively; (ii) GYTFTTYG (SEQ ID NO: 44), INTYSGVP (SEQ ID NO: 60) and CARSGHSYSLYVMGYW (SEQ ID NO: 72), respectively; (iii) GYTFTTYG (SEQ ID NO: 44), INTYSGVP (SEQ ID NO: 60) and CARSGHNYSLYVMGYW (SEQ ID NO: 73), respectively; (iv) GYTFTTYG (SEQ ID NO: 44), INTYSGVP (SEQ ID NO: 60) and CARGALYYFDNW (SEQ ID NO: 74), respectively; (v) GYMFTTYG (SEQ ID NO: 45), INTYSGVP (SEQ ID NO: 60) and CARIGNTNSLYTVHYW (SEQ ID NO: 75), respectively; (vi) GYTFTTYG (SEQ ID NO: 44), INTYSGVP (SEQ ID NO: 60) and CARIGNTNSLYTVHYW (SEQ ID NO: 75), respectively; (vii) GYTFTNYG (SEQ ID NO: 46), INTYSGVP (SEQ ID NO: 60) and CARIGNTNSLYTVHYW (SEQ ID NO: 75), respectively; (viii) GYTFTTYG (SEQ ID NO: 44), INTYSGVP (SEQ ID NO: 60) and CTRIGNTNSLYTVHYW (SEQ ID NO: 76), respectively; (ix) GYSITSGHY (SEQ ID NO: 47), ISYDGNN (SEQ ID NO: 61) and CVRGYYYYGSRAMDYW (SEQ ID NO: 77), respectively; (x) GYSITSGHY (SEQ ID NO: 47), ISYDGND (SEQ ID NO: 62) and CVRGYYYYGSRAMDCW (SEQ ID NO: 78), respectively; (xi) GFSFSDYG (SEQ ID NO: 48), ISSGSSTI (SEQ ID NO: 63) and CGPSDYWYFDVW (SEQ ID NO: 79), respectively; (xii) GFTFSDYG (SEQ ID NO: 49), ISSGSSTI (SEQ ID NO: 63) and CARDYFYGNNYGFPYW (SEQ ID NO: 80), respectively; (xiii) GYTFINYY (SEQ ID NO: 50), IYPGNINS (SEQ ID NO: 64) and CAMTNSSAMDYW (SEQ ID NO: 81), respectively; (xiv) GYTFISYY (SEQ ID NO: 51), IYPGNVNT (SEQ ID NO: 65) and CAMTNSSAMDYW (SEQ ID NO: 81), respectively; (xv) GYTFTSYY (SEQ ID NO: 52), IYPGNVNT (SEQ ID NO: 65) and CAMTNSSAMDYW (SEQ ID NO: 81), respectively; (xvi) GFSLTNYD (SEQ ID NO: 54), IWTGGNT (SEQ ID NO: 66) and CVREGFRQGYYAMDYW (SEQ ID NO: 82), respectively; (xvii) GYTFTDYY (SEQ ID NO: 55), IDTKNGGT (SEQ ID NO: 67) and CASGGRGYW (SEQ ID NO: 83), respectively; (xviii) GYTFTNYG (SEQ ID NO: 46), INTYTGEP (SEQ ID NO: 68) and CTRNYYRPYYYAMDYW (SEQ ID NO: 84), respectively; (xix) GYSFTGYT (SEQ ID NO: 57), INPYNDNT (SEQ ID NO: 69) and CAREGNYYGASPWFAYW (SEQ ID NO: 85), respectively; and (xx) GYTFTHYG (SEQ ID NO: 58), INTSTGET (SEQ ID NO: 70) and CARYYYGSSRWRDYWFAYW (SEQ ID NO: 86), respectively; and a light chain variable region comprising CDR1, CDR2, and CDR3, consisting of the amino acid sequences: (xxi) QSLLISTNQKNY (SEQ ID NO: 1), FAS (SEQ ID NO: 18) and CQQHYSIPPTF (SEQ ID NO: 27), respectively; (xxii) QSLFISTNQKNY (SEQ ID NO: 2), FAS (SEQ ID NO: 18) and CQQHYSSPPTF (SEQ ID NO: 28), respectively; (xxiii) QSLLISTNQINY (SEQ ID NO: 3), FAS (SEQ ID NO: 18) and CQQHYDPPLTF (SEQ ID NO: 29), respectively; (xxiv) QSLLISTNQKNY (SEQ ID NO: 1), FAS (SEQ ID NO: 18) and CQHHYDPPLTF (SEQ ID NO: 30), respectively; (xxv) QNLLNSSNQKNY (SEQ ID NO: 4), FAS (SEQ ID NO: 18) and CQQHYNTPPTF (SEQ ID NO: 31), respectively; (xxvi) QSLLNSSNQKNY (SEQ ID NO: 5), FAS (SEQ ID NO: 18) and CQQHYSPPPTF (SEQ ID NO: 32), respectively; (xxvii) QSLLISSNQNNY (SEQ ID NO: 6), FAS (SEQ ID NO: 18) and CQQHYSTPPTF (SEQ ID NO: 33), respectively; (xxviii) QDISNY (SEQ ID NO: 7), YTS (SEQ ID NO: 19) and CQQGHTLPYTF (SEQ ID NO: 34), respectively; (xxix) QDISNY (SEQ ID NO: 7), YTS (SEQ ID NO: 19) and CQQGNTLPYTF (SEQ ID NO: 35), respectively; (xxx) QNVGTN (SEQ ID NO: 8), STS (SEQ ID NO: 20) and CQQYNSYPFTF (SEQ ID NO: 36), respectively; (xxxi) QTIGTW (SEQ ID NO: 9), AAT (SEQ ID NO: 21) and CQQLYSTPLTF (SEQ ID NO: 37), respectively; (xxxii) QNIRTA (SEQ ID NO: 10), LAS (SEQ ID NO: 22) and CLQHWNYPFTF (SEQ ID NO: 38), respectively; (xxxiii) QNVRTA (SEQ ID NO: 11), LAS (SEQ ID NO: 22) and CLQHWNYPFTF (SEQ ID NO: 38), respectively; (xxxiv) LNVRTA (SEQ ID NO: 12), LAS (SEQ ID NO: 22) and CLQHWNYPFTF (SEQ ID NO: 38), respectively; (xxxv) QSLLYSSNQKNY (SEQ ID NO: 13), WAS (SEQ ID NO: 23) and CQQYYSYRTF (SEQ ID NO: 39), respectively; (xxxvi) QNVYTT (SEQ ID NO: 14), SAS (SEQ ID NO: 24) and CQQYNSYPYTF (SEQ ID NO: 40), respectively; (xxxvii) ENIYSY (SEQ ID NO: 15), DAK (SEQ ID NO: 25) and CQHHYGFPYTF (SEQ ID NO: 41), respectively; (xxxviii) ETVDTYGNRF (SEQ ID NO: 16), RAS (SEQ ID NO: 26) and CQQSNEDPFTF (SEQ ID NO: 42), and (xxxix) QDVSNA (SEQ ID NO: 17), SAS(SEQ ID NO: 24) and CPQHYSTLCTF (SEQ ID NO: 43), respectively.

In some aspects, the isolated antibody or antigen-binding fragment is an antagonist of LILRB3 activity.

In one aspect, the disclosure provides an antibody or antigen-binding fragment thereof that specifically binds to LILRB3, wherein the antibody or antigen-binding fragment comprises a heavy chain complementarity determining region (CDR) 1 comprising an amino acid sequence as set forth in one of SEQ ID NOs: 50, 52, 53, 55 and 109-114, or the amino acid sequence as set forth in one of SEQ ID NOs: 50, 52, 53, 55 and 109-114 with a substitution at two or fewer amino acid positions, a heavy chain CDR 2 comprising an amino acid sequence as set forth in one of SEQ ID NOs:65, and 115-123, or the amino acid sequence as set forth in one of SEQ ID NOs: 65, and 115-123 with a substitution at two or fewer amino acid positions, and a heavy chain CDR 3 comprising an amino acid sequence as set forth in one of SEQ ID NOs: 81, 124-131, or the amino acid sequence as set forth in one of SEQ ID NOs: 81, 124-131 with a substitution at two or fewer amino acid positions.

In one aspect, the disclosure provides an antibody or antigen-binding fragment thereof that specifically binds to LILRB3, wherein the antibody or antigen-binding fragment comprises light chain CDR 1 comprising an amino acid sequence as set forth in one of SEQ ID NOs: 1-17, or the amino acid sequence as set forth in one of SEQ ID NOs: 10, 11, 87-94, or the amino acid sequence as set forth in one of SEQ ID NOs: 10, 11, 87-94 with a substitution at two or fewer amino acid positions, a light chain CDR 2 comprises an amino acid sequence as set forth in one of SEQ ID NOs: 19, 22, 23, 95-99, or the amino acid sequence as set forth in one of SEQ ID NOs: 19, 22, 23, 95-99 with a substitution at two or fewer amino acid positions, and a light chain CDR 3 comprises an amino acid sequence as set forth in one of SEQ ID NOs: 38, 100-108, or the amino acid sequence as set forth in one of SEQ ID NOs: 38, 100-108 with a substitution at two or fewer amino acid positions.

In one aspect, the disclosure provides an antibody or antigen-binding fragment thereof specifically binds to LILRB3, wherein the antibody or antigen-binding fragment thereof comprises a heavy chain variable region comprising complementarity determining region (CDR)1, CDR2, and CDR3, consisting of the amino acid sequences: (xl) GFTFTGYW (SEQ ID NO: 109), ILPVSGIT (SEQ ID NO: 115) and CARRGSPYFDYW (SEQ ID NO: 124), respectively; (xli) GFSLNTFDMG (SEQ ID NO: 110), IWWDDDK (SEQ ID NO: 116) and CGRKPGGYGNYVL (SEQ ID NO: 125), respectively; (xlii) GFSLTRYG (SEQ ID NO: 111), IWSGGST (SEQ ID NO: 117) and CARDGRVYAMDYW (SEQ ID NO: 126), respectively; (xliii) GYTFTDYY (SEQ ID NO: 55), LNPYNGGT (SEQ ID NO: 118) and CARGSGNSFYAMDYW (SEQ ID NO: 127), respectively; (xliv) GYTFINYY (SEQ ID NO: 50), IYPGNVNS (SEQ ID NO: 119) and CAMTNSSAMDYW (SEQ ID NO: 81), respectively; (xlv) GYSITSGYY (SEQ ID NO: 112), ISYDGSN (SEQ ID NO: 120) and CTSIYGRFVYW (SEQ ID NO: 128), respectively; (xlvi) GFSLTRYG (SEQ ID NO: 111), IWSGGST (SEQ ID NO: 117) and CARDGRVYAMDYW (SEQ ID NO: 126), respectively; (xlvii) GYTFTNFW (SEQ ID NO: 113), IHPNSGST (SEQ ID NO: 121) and CARNSGDYL-VYFDSW (SEQ ID NO: 129), respectively, (xlviii) GYSFTGYF (SEQ ID NO: 114), INPSTGDT (SEQ ID NO: 122) and CARGATVVDYPFDYW (SEQ ID NO: 130), respectively, or (xlix) GYTFTSYW (SEQ ID NO: 53), IHPNGGST (SEQ ID NO: 123) and CTRGLTGLFAYW SEQ ID NO: 131), respectively.

In one aspect, the disclosure provides an antibody or antigen-binding fragment thereof specifically binds to LILRB3, wherein the antibody or antigen-binding fragment thereof comprises a heavy chain variable region comprising complementarity determining region (CDR)1, CDR2, and CDR3, consisting of the amino acid sequences: consisting of the amino acid sequences: (xl) GFTFTGYW (SEQ ID NO: 109), ILPVSGIT (SEQ ID NO: 115) and CARRGSPYFDYW (SEQ ID NO: 124), respectively; (xli) GFSLNTFDMG (SEQ ID NO: 110), IWWDDDK (SEQ ID NO: 116) and CGRKPGGYGNYVL (SEQ ID NO: 125), respectively; (xlii) GFSLTRYG (SEQ ID NO: 111), IWSGGST (SEQ ID NO: 117) and CARDGRVYAMDYW (SEQ ID NO: 126), respectively; (xliii) GYTFTDYY (SEQ ID NO: 55), LNPYNGGT (SEQ ID NO: 118) and CARGSGNSFYAMDYW (SEQ ID NO: 127), respectively; (xliv) GYTFINYY (SEQ ID NO: 50), IYPGNVNS (SEQ ID NO: 119) and CAMTNSSAMDYW (SEQ ID NO: 81), respectively; (xlv) GYSITSGYY (SEQ ID NO: 112), ISYDGSN (SEQ ID NO: 120) and CTSIYGRFVYW (SEQ ID NO: 128), respectively; (xlvi) GFSLTRYG (SEQ ID NO: 111), IWSGGST (SEQ ID NO: 117) and CARDGRVYAMDYW (SEQ ID NO: 126), respectively; (xlvii) GYTFTNFW (SEQ ID NO: 113), IHPNSGST (SEQ ID NO: 121) and CARNSGDYLVYFDSW (SEQ ID NO: 129), respectively, (xlviii) GYSFTGYF (SEQ ID NO: 114), INPSTGDT (SEQ ID NO: 122) and CARGATVVDYPFDYW (SEQ ID NO: 130), respectively, or (xlix) GYTFTSYW (SEQ ID NO: 53), IHPNGGST (SEQ ID NO: 123) and CTRGLTGLFAYW SEQ ID NO: 131), respectively; and a light chain variable region comprising CDR1, CDR2, and CDR3, consisting of the amino acid sequences: (1) SSVSSSY (SEQ ID NO: 87), GTS (SEQ ID NO: 95) and CHQYHRSPFTF (SEQ ID NO: 100), respectively; (li) SSVSY (SEQ ID NO: 88), DTS (SEQ ID NO: 96) and CFQGSGYPFTF (SEQ ID NO: 101), respectively; (lii) QSVLYSSDQKNY (SEQ ID NO: 89), WAS (SEQ ID NO: 23) and CHQYLSHTF (SEQ ID NO: 102), respectively; (liii) QDVNTA (SEQ ID NO: 90), WAS (SEQ ID NO: 23) and CQQLYKLPRTF (SEQ ID NO: 103), respectively; (lv) QNIRTA (SEQ ID NO: 10), LAS (SEQ ID NO: 22) and CLQHWNYPFTF (SEQ ID NO: 38), respectively; (lvi) SSVNY (SEQ ID NO: 92), YTS (SEQ ID NO:19) and CQQFSSSPYTF (SEQ ID NO: 105), respectively; (lvii) QNVRTA (SEQ ID NO: 11), LAS (SEQ ID NO: 22) and CLQHWNYPFTF (SEQ ID NO: 38), respectively; (lviii) SSVSY (SEQ ID NO: 88), DTS (SEQ ID NO: 96) and CQQWRSYQLTF (SEQ ID NO: 106), respectively; (lvix), QNINVW (SEQ ID NO: 93), KAS (SEQ ID NO: 98) and CQQGQSYPLTF (SEQ ID NO: 107)), respectively; and (lvx), QDINSY (SEQ ID NO: 94), RAN (SEQ ID NO: 99) and CLQYDEFLLTF (SEQ ID NO: 108), respectively.

In some aspects, the isolated antibody or antigen-binding fragment is an agonist of LILRB3 activity.

In one aspect, the disclosure provides an antibody or antigen-binding fragment thereof that specifically binds to LILRB3, wherein the antibody or antigen-binding fragment comprises a heavy chain complementarity determining region CDR 1 comprising an amino acid sequence as set forth in one of SEQ ID NOs: 44, 46, 49-52, 54, 112, 153, 190-214, or the amino acid sequence as set forth in one of SEQ ID NOs: 44, 46, 49-52, 54, 112, 153, 190-214 with a substitution at two or fewer amino acid positions, a heavy chain CDR 2 comprising an amino acid sequence as set forth in one of SEQ ID NOs: 60, 63, 64, 65119, 123, 215-237, or the amino acid sequence as set forth in one of SEQ ID NOs: 60, 63, 64, 65119, 123, 215-237 with a substitution at two or fewer amino acid positions, and a heavy chain CDR 3 comprising an amino acid sequence as set forth in one of SEQ ID NOs: 81, 82, 239-272, or the amino acid sequence as set forth in one of SEQ ID NOs: 81, 82, 239-272 with a substitution at two or fewer amino acid positions.

In one aspect, the disclosure provides an antibody or antigen-binding fragment thereof that specifically binds to LILRB3, wherein the antibody or antigen-binding fragment comprises a light chain CDR 1 comprising an amino acid sequence as set forth in one of SEQ ID NOs: 7, 8, 10, 11, 13, 15, 56, 87, 88, 94, 134-156, or the amino acid sequence as set forth in one of SEQ ID NOs: 7, 8, 10, 11, 13, 15, 56, 87, 88, 94, 134-156 with a substitution at two or fewer amino acid positions, a light chain CDR 2 comprising an amino acid sequence as set forth in one of SEQ ID NOs: 18, 19, 20, 21, 22, 23, 24, 26, 95, 99, 157-163, or the amino acid sequence as set forth in one of SEQ ID NOs: 18, 19, 20, 21, 22, 23, 24, 26, 95, 99, 157-163 with a substitution at two or fewer amino acid positions, and a light chain CDR 3 comprising an amino acid sequence as set forth in one of SEQ ID NOs: 38, 39, 40, 100, 108, 164-189, or the amino acid sequence as set forth in one of SEQ ID NOs: 38, 39, 40, 100, 108, 164-189 with a substitution at two or fewer amino acid positions.

In some aspects, the disclosure provides an isolated nucleic acid molecule encoding the anti-LILRB3 antibody or antigen-binding fragment thereof as disclosed herein. The disclosure also provides a vector comprising a nucleic acid molecule encoding the anti-LILRB3 antibody or antigen-binding fragment thereof as disclosed herein. Host cells, including prokaryotic or eukaryotic cells, comprising a vector comprising a nucleic acid molecule encoding the anti-LILRB3 antibody or antigen-binding fragment thereof as disclosed herein are also provided herein.

In some aspects, the disclosure provides methods for producing and anti-LILRB3 antibody or antigen-binding fragment thereof comprising the steps of (a) culturing a host cell of claim 8 under conditions suitable for expression of the LILRB3 antibody or antigen-binding fragment thereof by the host cell; and (b) recovering the LILRB3 antibody or antigen-binding fragment thereof.

Compositions comprising the anti-LILRB3 antibody or antigen-binding fragment thereof and a suitable pharmaceutical carrier are disclosed herein. In some aspects, the compositions further comprise a chemotherapeutic agent or an analgesic. In some aspects, the compositions further comprise a one or more additional agents selected from the group consisting of: a myeloid-derived suppressor cell, a mobilizing agent, a c-jun N-terminal kinase inhibitor, an anti-inflammatory agent, and an immunosuppressive agent.

The compositions of the present disclosure can be formulated, for example, for intravenous, intramuscular, oral, subcutaneous, intraperitoneal, intrathecal, intratumoral or intramuscular administration.

In some aspects, the disclosure provides methods for treating cancer in a subject, the method comprising administering to the subject a therapeutically effective amount of the antibody or antigen-binding fragment thereof that specifically binds to LILRB3 as described herein. In some aspects, the methods further comprise administering to the mammal a chemotherapeutic agent or an analgesic.

In one aspect, this disclosure provides a pharmaceutical composition comprising the anti-LILRB3 antibody or antigen-binding fragment thereof (e.g., Fab or scFv) described herein and a pharmaceutically acceptable carrier.

In certain embodiments of the above aspects, the antibody or antigen-binding fragment thereof has an apparent monovalent affinity of about 150 pM to about 100 nM.

In certain embodiments of all of the above aspects, the antibody or the antigen-binding fragment thereof is an Fab, an Fab', an F(ab')2, an Facb, an Fv, an Fd, a diabody, an scFv, or an sc(Fv)2. In a specific embodiment, the antibody or the antigen-binding fragment thereof is an Fab.

As used herein, the term "one or more" includes at least one, more suitably, one, two, three, four, five, ten, twenty, fifty, one-hundred, five-hundred, etc., of the item to which "one or more" refers.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 2A-2B are graphs showing the production of IL-10 from PBMCs obtained from healthy donors after treatment with anti-LILRB3 hybridoma supernatants or purified antibodies (5 μg/ml), or isotype control for 24 hours followed by stimulation with LPS (100 ng/ml) for 6 hours. Supernatants were collected and IL-10 concentrations were measured by ELISA. The overall difference in IL-10 concentrations is presented in FIG. 2A, while the relative fold change is shown in FIG. 2B. For each of FIG. 2A and FIG. 2B, the clones are ordered according to the clonal ranking presented in FIG. 1A

DETAILED DESCRIPTION

Figure 1A:
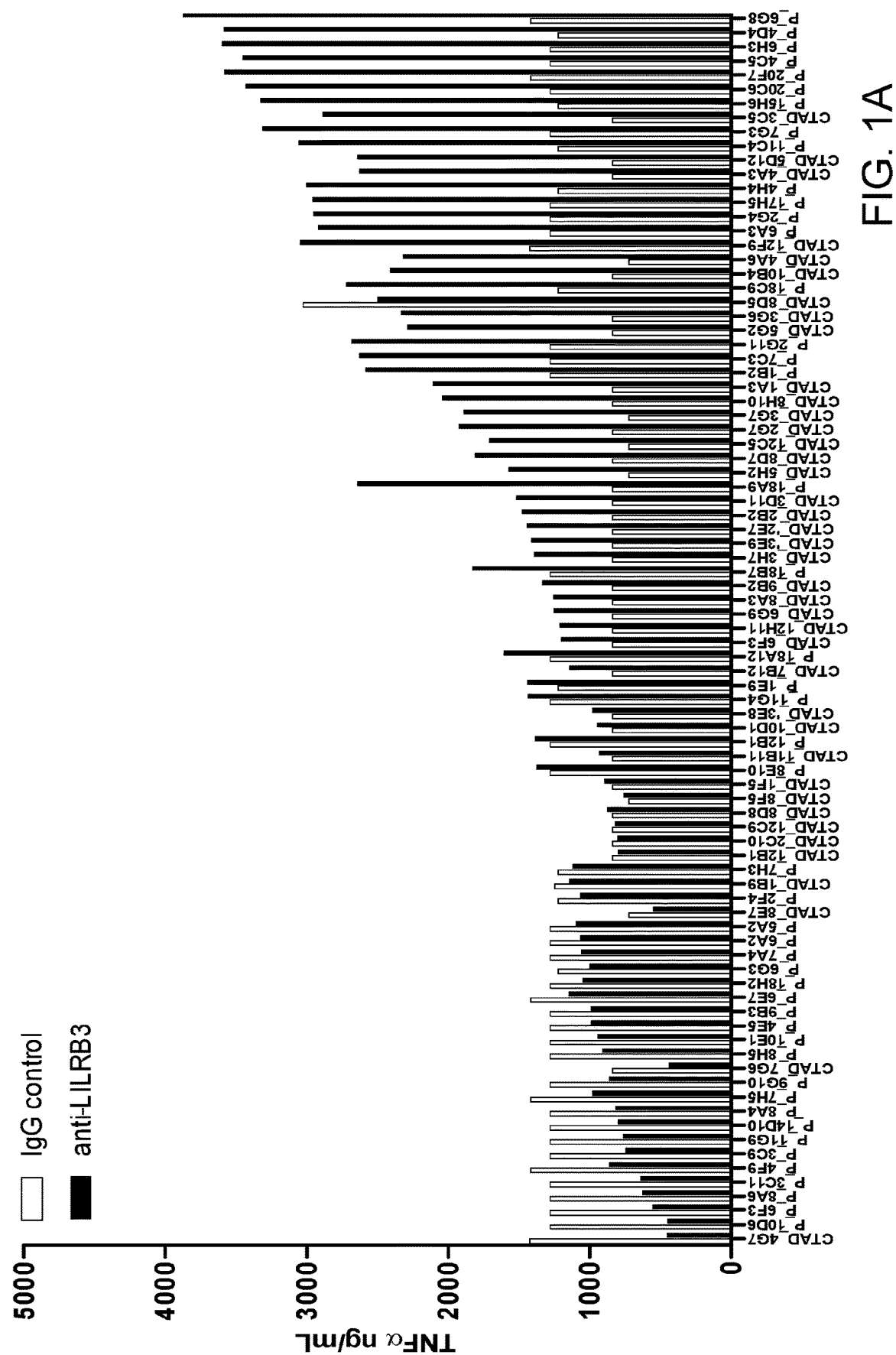
FIGS. 1A-1C are graphs showing the production of TNF-α from human peripheral blood mononuclear cells (PBMC) obtained from healthy donors after incubation with anti-LILRB3 hybridoma supernatants, or purified antibodies (5 μg/ml), or isotype control for 24 hours following stimulation with LPS (100 ng/ml). Anti-LILRB3 mAbs were ranked in order of clones that suppress TNF alpha release to those that enhance TNF alpha secretion. The levels of TNF-α were determined by ELISA. Clone ranking based on production of TNF-α from FIG. 1 is presented. The overall difference in TNF alpha levels from FIG. 1A is presented in FIG. 1B, while the relative fold change in TNF alpha release is shown in FIG. 1C.

This disclosure features antibodies and antigen-binding fragments that specifically bind LILRB3.

The disclosure also provides polynucleotides encoding the antibodies and antigen-binding fragments thereof described herein. In addition, this disclosure relates to methods of using the anti-LILRB3 antibodies and antigen-binding fragments thereof in the treatment of cancer and/or stimulating a pro-inflammatory immune response.

In order to provide a clear understanding of the specification and claims, the following definitions are provided below.

Definitions

It is understood that wherever embodiments are described herein with the language "comprising," otherwise analogous embodiments described in terms of "consisting of" and/or "consisting essentially of" are also provided.

The term "antibody" means an immunoglobulin molecule that recognizes and specifically binds to a target, such as a protein (e.g., the LILR3, a subunit thereof, or the receptor complex), polypeptide, peptide, carbohydrate, polynucleotide, lipid, or combinations of the foregoing through at least one antigen recognition site within the variable region of the immunoglobulin molecule. A typical antibody comprises at least two heavy (HC) chains and two light (LC) chains interconnected by disulfide bonds. Each heavy chain is comprised of a "heavy chain variable region" or "heavy chain variable domain" (abbreviated herein as $V_H$) and a heavy chain constant region. The heavy chain constant region is comprised of three domains, CH1, CH2, and CH3. Each light chain is comprised of a "light chain variable region" or "light chain variable domain" (abbreviated herein as $V_L$) and a light chain constant region. The light chain constant region is comprised of one domain, C1. The $V_H$ and $V_L$ regions can be further subdivided into regions of hypervariablity, termed Complementarity Determining Regions (CDR), interspersed with regions that are more conserved, termed framework regions (FRs). Each $V_H$ and $V_L$ region is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. As used herein, the term "antibody" encompasses intact polyclonal antibodies, intact monoclonal antibodies, antibody fragments (such as Fab, Fab', F(ab')2, Fd, Facb, and Fv fragments), single chain Fv (scFv), minibodies (e.g., sc(Fv)2, diabody), multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. Thus, the term "antibody" includes whole antibodies and any antigen-binding fragment or single chains thereof. Antibodies can be naked or conjugated to other molecules such as toxins, radioisotopes, small molecule drugs, polypeptides, etc.

The term "isolated antibody" refers to an antibody that has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, and including more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody as defined above, e.g., because the entire variable region of a chimeric antibody is non-human.

The term "antigen binding fragment" refers to a portion of an intact antibody and refers to the antigenic determining variable regions of an intact antibody. It is known in the art that the antigen binding function of an antibody can be performed by fragments of a full-length antibody. Examples of antigen-binding antibody fragments include, but are not limited to Fab, Fab', F(ab')2, Facb, Fd, and Fv fragments, linear antibodies, single chain antibodies, and multispecific antibodies formed from antibody fragments. In some instances, antibody fragments may be prepared by proteolytic digestion of intact or whole antibodies. For example, antibody fragments can be obtained by treating the whole antibody with an enzyme such as papain, pepsin, or plasmin. Papain digestion of whole antibodies produces F(ab)2 or Fab fragments; pepsin digestion of whole antibodies yields F(ab')2 or Fab'; and plasmin digestion of whole antibodies yields Facb fragments.

The term "Fab" refers to an antibody fragment that is essentially equivalent to that obtained by digestion of immunoglobulin (typically IgG) with the enzyme papain. The heavy chain segment of the Fab fragment is the Fd piece. Such fragments can be enzymatically or chemically produced by fragmentation of an intact antibody, recombinantly produced from a gene encoding the partial antibody sequence, or it can be wholly or partially synthetically produced. The term "F(ab')2" refers to an antibody fragment that is essentially equivalent to a fragment obtained by digestion of an immunoglobulin (typically IgG) with the enzyme pepsin at pH 4.0-4.5. Such fragments can be enzymatically or chemically produced by fragmentation of an intact antibody, recombinantly produced from a gene encoding the partial antibody sequence, or it can be wholly or partially synthetically produced. The term "Fv" refers to an antibody fragment that consists of one NH and one N domain held together by noncovalent interactions.

As used herein the term "scFv" or "scFv molecule" includes binding molecules which consist of one light chain variable domain (VL) or a portion thereof, and one heavy chain variable domain (VH) or a portion thereof, wherein each variable domain (or a portion thereof) is derived from the same or different antibodies. Single chain Fv molecules preferably comprise an scFv linker interposed between the VH domain and the VL domain. Exemplary scFv molecules are known in the art and are described, for example, in U.S. Pat. No. 5,892,019; Ho et al, Gene, 77:51 (1989); Bird et al., Science, 242:423 (1988); Pantoliano et al, *Biochemistry*, 30: 101 17 (1991); Milenic et al, *Cancer Research*, 51:6363 (1991); Takkinen et al, Protein Engineering, 4:837 (1991). The term "scFv linker" as used herein refers to a moiety interposed between the VL and VH domains of the scFv. The scFv linkers preferably maintain the scFv molecule in an antigen-binding conformation. In one embodiment, a scFv linker comprises or consists of an scFv linker peptide. In certain embodiments, an scFv linker peptide comprises or consists of a Gly-Ser peptide linker. In other embodiments, an scFv linker comprises a disulfide bond.

The terms "LILRB3 antibody," "anti-LILRB3 antibody," "anti-LILRB3," "antibody that binds to LILRB3" and any grammatical variations thereof refer to an antibody that is capable of specifically binding to the LILRB3 with sufficient affinity such that the antibody is useful as a therapeutic agent or diagnostic reagent in targeting LILRB3. The extent of binding of an anti-LILRB3 antibody disclosed herein to an unrelated, non-LILRB3 protein is less than about 10% of the binding of the antibody to LILRB3 as measured, e.g., by a radioimmunoassay (RIA), BIACORE™ (using recombinant LILRB3 as the analyte and antibody as the ligand, or vice versa), or other binding assays known in the art. In certain embodiments, an antibody that binds to LILRB3 has a dissociation constant (KD) of <1 µM, <100 nM, <50 nM, <10 nM, or <1 nM.

The term "% identical" between two polypeptide (or polynucleotide) sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence. The percentage of sequence identity is calculated by determining the number of positions at which the identical amino acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software both for online use and for download. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). B12seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence. One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org (ClustalX is a version of the ClustalW2 program ported to the Windows environment). Another suitable program is MUSCLE, available from www.drive5.com/muscle. ClustalW2 and MUSCLE are alternatively available, e.g., from the EBI.

The term "therapeutic agent" refers to any biological or chemical agent used in the treatment of a disease or disorder. Therapeutic agents include any suitable biologically active chemical compounds, biologically derived components such as cells, peptides, antibodies, and polynucleotides, and radiochemical therapeutic agents such as radioisotopes. In some embodiments, the therapeutic agent comprises a chemotherapeutic agent or an analgesic.

The terms "treat," and "treating," as used herein with reference to a disorder associated with increased cellular death, e.g., ischemia, refer to a decrease in the occurrence of tissue and/or cellular damage in an animal or human. The prevention may be complete, e.g., the total absence of tissue damage in a subject. The prevention may also be partial, such that the occurrence of tissue damage in a subject is less than that which would have occurred without the therapeutic agent.

The terms "prevent," "preventing," and "prevention," as used herein, shall refer to a decrease in the occurrence of a disease or decrease in the risk of acquiring a disease or its associated symptoms in a subject. The prevention may be complete, e.g., the total absence of disease or pathological cells in a subject. The prevention may also be partial, such that the occurrence of the disease or pathological cells in a subject is less than that which would have occurred without the present invention.

LILRB3

By the term "leukocyte immunoglobulin (Ig)-like receptor B3" or "LILRB3" is meant a mammalian (e.g., human) LILRB3 protein or mRNA, or a LILRB3 protein or mRNA derived from a mammalian (e.g., human) LILRB3 protein or mRNA. Non-limiting examples of LILRB3 proteins and mRNA are described herein. Additional examples of LILRB3 proteins and mRNA are known in the art.

Two amino acid polymorphisms of human LILRB3 are provided below:

(AAI04994)

(SEQ ID NO: 132)

MTPALTALLCLGLSLGPRTRVQAGPFPKPTLWAEPGSVISWGSPVTIW

CQGSLEAQEYRLDKEGSPEPLDRNNPLEPKNKARFSIPSMTEHHAGRY

RCHYYSSAGWSEPSDPLELVMTGFYNKPTLSALPSPVVASGGNMTLR

CGSQKGYHHFVLMKEGEHQLPRTLDSQQLHSGGFQALFPVGPVNPSH

RWRFTCYYYYMNTPQVWSHPSDPLEILPSGVSRKPSLLTLQGPVLAPG

QSLTLQCGSDVGYDRFVLYKEGERDFLQRPGQQPQAGLSQANFTLGP

VSRSHGGQYRCYGAHNLSSEWSAPSDPLNILMAGQIYDTVSLSAQPGP

TVASGENVTLLCQSWWQFDTFLLTKEGAAHPPLRLRSMYGAHKYQA

EFPMSPVTSAHAGTYRCYGSYSSNPHLLSFPSEPLELMVSGHSGGSSLP

PTGPPSTPGLGRYLEVLIGVSVAFVLLLFLLLFLLLRRQRHSKHRTSDQ

RKTDFQRPAGAAETEPKDRGLLRRSSPAADVQEENLYAAVKDTQSED

RVELDSQSPHDEDPQAVTYAPVKHSSPRREMASPPSSLSGEFLDTKDR

QVEEDRQMDTEAAASEASQDVTYAQLHSLTLRRKATEPPPSQEGEPP

AEPSIYATLAIH and its variants (XP_006723046.1):

(SEQ ID NO: 133)

MTPALTALLCLGLSLGPRTRMQAGPFPKPTLWAEPGSVISWGSPVTIW

CQGSLEAQEYQLDKEGSPEPWDRNNPLEPKNKARFSIPSMTQHHAGR

YRCHYYSSAGWSEPSDPLELVMTGFYNKPTLSALPSPVVASGGNMTL

RCGSQKGYHHFVLMKEGEHQLPRTLDSQQLHSGGFQALFPVGPVTPS

HRWRFTCYYYYTNTPWVWSHPSDPLEILPSGVSRKPSLLTLQGPVLAP

GQSLTLQCGSDVGYDRFVLYKEGERDFLQRPGQQPQAGLSQANFTLG

PVSRSYGGQYRCYGAHNLSSEWSAPSDPLDILITGQIYDTVSLSAQPGP

TVASGENMTLLCQSRGYFDTFLLTKEGAAHPPLRLRSMYGAHKYQAE

FPMSPVTSAHAGTYRCYGSRSSNPHLLSFPSEPLELMVSGHSGGSSLPP

TGPPSTPGLGRYLEVLIGVSVAFVLLLFLLLFLLLLRQRHSKHRTSDQR

KTDFQRPAGAAETEPKDRGLLRRSSPAADVQEENLCKRKRGDKWGC

WRDRSPKISVATGRGWEGSGAPWKMVLPHTVGPPCIRWPHLGAGQG

ASRTERSQRTRRRTPCSAPADAAVKDTQSEDRVELDSQSPHDEDPQAV

TYAPVKHSSPRREMASPPSSLSGEFLDTKDRQVEEDRQMDTEAAASEA

SQDVTYAQLHSLTLRRKATEPPPSQEGEPPAEPSIYATLAIH and its variants.

By the term "LILRB3 agonist" is meant an agent that specifically binds to LILRB3 protein and activates LILRB3 signaling pathways in a mammalian cell. Non-limiting examples of LILRB3 agonists are described herein. Examples of LILRB3 signaling pathways are described in the WO2013/181438, which is incorporated herein in its entirety.

By the term "LILRB3 antagonist" is meant an agent that specifically binds to LILRB3 protein and decreases the activity, activation or function of the LILRB3 signaling pathways in a mammalian cell. Non-limiting examples of LILRB3 antagonist are described herein.

Anti-LILRB3 Antibodies

This disclosure provides antibodies and antigen-binding fragments thereof that specifically bind to LILRB3. Examples of anti-LILRB3 antagonist antibodies (murine) are provided in Table 1.

TABLE 1

Murine Anti-LILRB3 CDR* Amino Acid Sequences

| ID | variable Light (VL) chain CDR sequences | | | Variable Heavy (VH) chain CDR sequences | | |
|---|---|---|---|---|---|---|
| | CDR1 | CDR2 | CDR3 | CDR1 | CDR2 | CDR3 |
| P 6H3 | QSLLISTNQKNY (SEQ ID NO: 1) | FAS (SEQ ID NO: 18) | CQQHYSIPPTF (SEQ ID NO: 27) | GYTFTTYG (SEQ ID NO: 44) | MNTYSGVP (SEQ ID NO: 59) | CARMGRGSLYGMDYW (SEQ ID NO: 71) |
| P 4H4 | QSLFISTNQKNY (SEQ ID NO: 2) | FAS (SEQ ID NO: 18) | CQQHYSSPPT F (SEQ ID NO: 28) | GYTFTTYG (SEQ ID NO: 44) | INTYSGVP (SEQ ID NO: 60) | CARSGHSYSLYVMGYW (SEQ ID NO: 72) |
| P 4D4 | QSLFISTNQKNY (SEQ ID NO: 2) | FAS (SEQ ID NO: 18) | CQQHYSSPPT F (SEQ ID NO: 28) | GYTFTTYG (SEQ ID NO: 44) | INTYSGVP (SEQ ID NO: 60) | CARSGHSYSLYVMGYW (SEQ ID NO: 72) |
| P 15H6 | QSLFISTNQKNY (SEQ ID NO: 2) | FAS (SEQ ID NO: 18) | CQQHYSSPPT F (SEQ ID NO: 28) | GYTFTTYG (SEQ ID NO: 44) | INTYSGVP (SEQ ID NO: 60) | CARSGHNYSLYVMGYW (SEQ ID NO: 73) |
| P 11C4 | QSLFISTNQKNY (SEQ ID NO: 2) | FAS (SEQ ID NO: 18) | CQQHYSSPPT F (SEQ ID NO: 28) | GYTFTTYG (SEQ ID NO: 44) | INTYSGVP (SEQ ID NO: 60) | CARSGHNYSLYVMGYW (SEQ ID NO: 73) |
| P 18C9 | QSLFISTNQKNY (SEQ ID NO: 2) | FAS (SEQ ID NO: 18) | CQQHYSSPPT F (SEQ ID NO: 28) | GYTFTTYG (SEQ ID NO: 44) | INTYSGVP (SEQ ID NO: 60) | CARSGHNYSLYVMGYW (SEQ ID NO: 73) |
| P 2G11 | QSLLISTNQINY (SEQ ID NO: 3) | FAS (SEQ ID NO: 18) | CQQHYDPPLT (SEQ ID NO: 29) | GYTFTTYG (SEQ ID NO: 44) | INTYSGVP (SEQ ID NO: 60) | CARGALYYFDNW (SEQ ID NO: 74) |
| P 2G4 | QSLFISTNQINY (SEQ ID NO: 3) | FAS (SEQ ID NO: 18) | CQQHYDPPLT (SEQ ID NO: 29) | GYTFTTYG (SEQ ID NO: 44) | INTYSGVP (SEQ ID NO: 60) | CARGALYYFDNW (SEQ ID NO: 74) |
| P 6A3 | QSLLISTNQKNY (SEQ ID NO: 1) | FAS (SEQ ID NO: 18) | CQHHYDPPLT (SEQ ID NO: 30) | GYTFTTYG (SEQ ID NO: 44) | INTYSGVP (SEQ ID NO: 60) | CARGALYYFDNW (SEQ ID NO: 74) |
| P 4C5 | QNLLNSSNQKNY (SEQ ID NO: 4) | FAS (SEQ ID NO: 18) | CQQHYNTPPT (SEQ ID NO: 31) | GYMFTTYG (SEQ ID NO: 45) | INTYSGVP (SEQ ID NO: 60) | CARIGNTNSLYTVHYW (SEQ ID NO: 75) |
| P 1B2 | QSLLNSSNQKNY (SEQ ID NO: 5) | FAS (SEQ ID NO: 18) | CQQHYSPPPT F (SEQ ID NO: 32) | GYTFTTYG (SEQ ID NO: 44) | INTYSGVP (SEQ ID NO: 60) | CARIGNTNSLYTVHYW (SEQ ID NO: 75) |

TABLE 1-continued

Murine Anti-LILRB3 CDR* Amino Acid Sequences

| ID | Variable Light (VL) chain CDR sequences | | | Variable Heavy (VH) chain CDR sequences | | |
|---|---|---|---|---|---|---|
| | CDR1 | CDR2 | CDR3 | CDR1 | CDR2 | CDR3 |
| P 17H5 | QSLLISSNQNNY (SEQ ID NO: 6) | FAS (SEQ ID NO: 18) | CQQHYSTPPT F (SEQ ID NO: 33) | GYTFTNYG (SEQ ID NO: 46) | INTYSGVP (SEQ ID NO: 60) | CARIGNTNSLYTVHYW (SEQ ID NO: 75) |
| P 7G3 | QNLLNSSNQKNY (SEQ ID NO: 4) | FAS (SEQ ID NO: 18) | CQQHYSTPPT F (SEQ ID NO: 33) | GYTFTTYG (SEQ ID NO: 44) | INTYSGVP (SEQ ID NO: 60) | CTRIGNTNSLYTVHYW (SEQ ID NO: 76) |
| P 20F7 | QDISNY (SEQ ID NO: 7) | YTS (SEQ ID NO: 19) | CQQGHTLPYT F (SEQ ID NO: 34) | GYSITSGHY (SEQ ID NO: 47) | ISYDGNN (SEQ ID NO: 61) | CVRGYYYGSRAMDYW (SEQ ID NO: 77) |
| P 6G8 | QDISNY (SEQ ID NO: 7) | YTS (SEQ ID NO: 19) | CQQGNTLPYT F (SEQ ID NO: 35) | GYSITSGHY (SEQ ID NO: 47) | ISYDGND (SEQ ID NO: 62) | CVRGYYYGSRAMDCW (SEQ ID NO: 78) |
| P 7C3 | QNVGTN (SEQ ID NO: 8) | STS (SEQ ID NO: 20) | CQQYNSYPFT F (SEQ ID NO: 36) | GFSFSDYG (SEQ ID NO: 48) | ISSGSSTI (SEQ ID NO: 63) | CGPSDYWYFDVVV (SEQ ID NO: 79) |
| P 20C6 | QTIGTW (SEQ ID NO: 9) | AAT (SEQ ID NO: 21) | CQQLYSTPLTF (SEQ ID NO: 37) | GFTFSDYG (SEQ ID NO: 49) | ISSGSSTI (SEQ ID NO: 63) | CARDYFYGNNYGFPYW (SEQ ID NO: 80) |
| CTAD 8H10 | QNIRTA (SEQ ID NO: 10) | LAS (SEQ ID NO: 22) | CLQHWNYPF TF (SEQ ID NO: 38) | GYTFINYY (SEQ ID NO: 50) | IYPGNINS (SEQ ID NO: 64) | CAMTNSSAMDYW (SEQ ID NO: 81) |
| CTAD 8D7 | QNVRTA (SEQ ID NO: 11) | LAS (SEQ ID NO: 22) | CLQHWNYPF TF (SEQ ID NO: 38) | GYTFISYY (SEQ ID NO: 51) | IYPGNVNT (SEQ ID NO: 65) | CAMTNSSAMDYW (SEQ ID NO: 81) |
| CTAD 5G2 | QNVRTA (SEQ ID NO: 11) | LAS (SEQ ID NO: 22) | CLQHWNYPF TF (SEQ ID NO: 38) | GYTFISYY (SEQ ID NO: 51) | IYPGNVNT (SEQ ID NO: 65) | CAMTNSSAMDYW (SEQ ID NO: 81) |
| CTAD 3D11 | QNVRTA (SEQ ID NO: 11) | LAS (SEQ ID NO: 22) | CLQHWNYPF TF (SEQ ID NO: 38) | GYTFISYY (SEQ ID NO: 51) | IYPGNVNT (SEQ ID NO: 65) | CAMTNSSAMDYW (SEQ ID NO: 81) |
| CTAD 12F9 | QNVRTA (SEQ ID NO: 11) | LAS (SEQ ID NO: 22) | CLQHWNYPF TF (SEQ ID NO: 38) | GYTFISYY (SEQ ID NO: 51) | IYPGNVNT (SEQ ID NO: 65) | CAMTNSSAMDYW (SEQ ID NO: 81) |

TABLE 1-continued

| ID | | Murine Anti-LILRB3 CDR* Amino Acid Sequences | | | | | |
|---|---|---|---|---|---|---|---|
| | | Variable Light (VL) chain CDR sequences | | | Variable Heavy (VH) chain CDR sequences | | |
| | | CDR1 | CDR2 | CDR3 | CDR1 | CDR2 | CDR3 |
| CTAD | 2B2 | QNVRTA (SEQ ID NO: 11) | LAS (SEQ ID NO: 22) | CLQHWNYPF TF (SEQ ID NO: 38) | GYTFISYY (SEQ ID NO: 51) | IYPGNVNT (SEQ ID NO: 65) | CAMTNSSAMDYW (SEQ ID NO: 81) |
| CTAD | 10B4 | LNVRTA (SEQ ID NO: 12) | LAS (SEQ ID NO: 22) | CLQHWNYPF TF (SEQ ID NO: 38) | GYTFTSYY (SEQ ID NO: 52) | IYPGNVNT (SEQ ID NO: 65) | CAMTNSSAMDYW (SEQ ID NO: 81) |
| CTAD | 8A3 | QSLLYSSNQKNY (SEQ ID NO: 13) | WAS (SEQ ID NO: 23) | CQQYYSYRTF (SEQ ID NO: 39) | GFSLTNYD (SEQ ID NO: 54) | IWTGGNT (SEQ ID NO: 66) | CVREGFRQGYYAMDYW (SEQ ID NO: 82) |
| P | 18A9 | QNVYTT (SEQ ID NO: 14) | SAS (SEQ ID NO: 24) | CQQYNSYPYT F (SEQ ID NO: 40) | GYTFTDYY (SEQ ID NO: 55) | IDTKNGGT (SEQ ID NO: 67) | CASGGRGYW (SEQ ID NO: 83) |
| CTAD | 3G7 | ENIYSY (SEQ ID NO: 15) | DAK (SEQ ID NO: 25) | CQHHYGFPYT F (SEQ ID NO: 41) | GYTFTNYG (SEQ ID NO: 46) | INTYTGEP (SEQ ID NO: 68) | CTRNYYRPYYYAMDYW (SEQ ID NO: 84) |
| CTAD | 4A6 | ENIYSY (SEQ ID NO: 15) | DAK (SEQ ID NO: 25) | CQHHYGFPYT F (SEQ ID NO: 41) | GYTFTNYG (SEQ ID NO: 46) | INTYTGEP (SEQ ID NO: 68) | CTRNYYRPYYYAMDYW (SEQ ID NO: 84) |
| CTAD | 3G6 | ETVDTYGNRF (SEQ ID NO: 16) | RAS (SEQ ID NO: 26) | CQQSNEDPFT F (SEQ ID NO: 42) | GYSFTGYT (SEQ ID NO: 57) | INPYNDNT (SEQ ID NO: 69) | CAREGNYYGASPWFAY W (SEQ ID NO: 85) |
| CTAD | 1A3 | QDVSNA (SEQ ID NO: 17) | SAS (SEQ ID NO: 24) | CPQHYSTLCTF (SEQ ID NO: 43) | GYTFTHYG (SEQ ID NO: 58) | INTSTGET (SEQ ID NO: 70) | CARYYYGSSRWRDYWFA YW (SEQ ID NO: 86) |

*The CDRs are based on Kabat Numbering System

TABLE 2

Murine Anti-LILRB3 CDR Amino Acid Sequences

| ID | variable Light (VL) chain CDR sequences | | | variable Heavy (VH) chain CDR sequences | | |
|---|---|---|---|---|---|---|
| | CDR1 | CDR2 | CDR3 | CDR1 | CDR2 | CDR3 |
| P 4F9 | SSVSSSY (SEQ ID NO: 87) | GTS (SEQ ID NO: 95) | CHQYHRSPFTF (SEQ ID NO: 100) | GFTFTGYW (SEQ ID NO: 109) | ILPVSGIT (SEQ ID NO: 115) | CARRGSPYFDYW (SEQ ID NO: 124) |
| P 3C11 | SSVSY (SEQ ID NO: 88) | DTS (SEQ ID NO: 96) | CFQGSGYPFTF (SEQ ID NO: 101) | GFSLNTFDMG (SEQ ID NO: 110) | IWWDDDK (SEQ ID NO: 116) | CGRKPGGYGNYVL (SEQ ID NO: 125) |
| P 6G3 | QSVLYSSDQKNY (SEQ ID NO: 89) | WAS (SEQ ID NO: 23) | CHQYLSHTF (SEQ ID NO: 102) | GFSLTRYG (SEQ ID NO: 111) | IWSGGST (SEQ ID NO: 117) | CARDGRVYAMDYW (SEQ ID NO: 126) |
| P 7H5 | QDVNTA (SEQ ID NO: 90) | WAS (SEQ ID NO: 23) | CQQLYKLPRTF (SEQ ID NO: 103) | GFSLTRYG (SEQ ID NO: 111) | IWSGGST (SEQ ID NO: 117) | CARDGRVYAMDYW (SEQ ID NO: 126) |
| P 6E7 | QSLVNSYGITY (SEQ ID NO: 91) | GIS (SEQ ID NO: 97) | CLQGTHQPWTF (SEQ ID NO: 104) | GYTFTDYY (SEQ ID NO: 55) | LNPYNGGT (SEQ ID NO: 118) | CARGSGNSFYAMDYW (SEQ ID NO: 127) |
| CTAD 8D5 | QNIRTA (SEQ ID NO: 10) | LAS (SEQ ID NO: 22) | CLQHWNYPFTF (SEQ ID NO: 38) | GYTFINYY (SEQ ID NO: 50) | IYPGNVNS (SEQ ID NO: 119) | CAMTNSSAMDYW (SEQ ID NO: 81) |
| CTAD 1B9 | QNIRTA (SEQ ID NO: 10) | LAS (SEQ ID NO: 22) | CLQHWNYPFTF (SEQ ID NO: 38) | GYTFINYY (SEQ ID NO: 50) | IYPGNVNS (SEQ ID NO: 119) | CAMTNSSAMDYW (SEQ ID NO: 81) |
| CTAD 12B1 | SSVNY (SEQ ID NO: 92) | YTS (SEQ ID NO: 19) | CQQFSSSPYTF (SEQ ID NO: 105) | GYSITSGYY (SEQ ID NO: 112) | ISYDGSN (SEQ ID NO: 120) | CTSIYGRPVYW (SEQ ID NO: 128) |
| CTAD 10D1 | QNVRTA (SEQ ID NO: 11) | LAS (SEQ ID NO: 22) | CLQHWNYPFTF (SEQ ID NO: 38) | GYTFTSYY (SEQ ID NO: 52) | IYPGNVNT (SEQ ID NO: 65) | CAMTNSSAMDYW (SEQ ID NO: 81) |
| P 5A2 | SSVSY (SEQ ID NO: 88) | DTS (SEQ ID NO: 96) | CQQWRSYQLTF (SEQ ID NO: 106) | GYTFTNFW (SEQ ID NO: 113) | IHPNSGST (SEQ ID NO: 121) | CARNSGDYLVYFDSW (SEQ ID NO: 129) |
| P 8A6 | QNINVW (SEQ ID NO: 93) | KAS (SEQ ID NO: 98) | CQQGQSYPLTF (SEQ ID NO: 107) | GYSFTGYF (SEQ ID NO: 114) | INPSTGDT (SEQ ID NO: 122) | CARGATVDYPFDYW (SEQ ID NO: 130) |
| P 3C9 | QDINSY (SEQ ID NO: 94) | RAN (SEQ ID NO: 99) | CLQYDEFLLTF (SEQ ID NO: 108) | GYTFTSVW (SEQ ID NO: 53) | IHPNGGST (SEQ ID NO: 123) | CTRGLTGLFAYW (SEQ ID NO: 131) |

*The CDRs are based on Kabat Numbering System

TABLE 3

| Clone | variable Light (VL) chain CDR sequences | | | variable Heavy (VH) chain CDR sequences | | |
|---|---|---|---|---|---|---|
| | CDR1 | CDR | CDR3 | CDR1 | CDR2 | CDR3 |
| 1E9 | ESVLIIDTNL (SEQ ID NO: 134) | HAS (SEQ ID NO: 157) | CLQSRKIPPTF (SEQ ID NO: 164) | GYTFTNYG (SEQ ID NO: 46) | INTYSGVP (SEQ ID NO: 60) | CARRAYGTSHFDYW (SEQ ID NO: 239) |
| 2F4 | ESVTIIDTHL (SEQ ID NO: 135) | HSS (SEQ ID NO: 158) | CLQSRKIPPTF (SEQ ID NO: 164) | GYTFTTYG (SEQ ID NO: 44) | INTYSGVP (SEQ ID NO: 60) | CARRAYGTSHFDYW SEQ ID NO: 239) |
| 6F3 | QDINSY (SEQ ID NO: 94) | RAN (SEQ ID NO: 99) | CLQYDEFLLTF (SEQ ID NO: 108) | GFSLTSYG (SEQ ID NO: 190) | IWGDGST (SEQ ID NO: 215) | CAKPNWDYYAMDYW (SEQ ID NO: 240) |
| 14D10 | QDINSY (SEQ ID NO: 94) | RAN (SEQ ID NO: 99) | CLQYDEFLLTF (SEQ ID NO: 108) | GYTFTDHT (SEQ ID NO: 191) | IYPKDGYT (SEQ ID NO: 216) | CARTWDYFDYW (SEQ ID NO: 241) |
| 6A2 | SSVSY (SEQ ID NO: 88) | ATS (SEQ ID NO: 95) | CQQWNTNPYTF (SEQ ID NO: 165) | GYTFTTYG (SEQ ID NO: 44) | INTYSGVP (SEQ ID NO: 60) | CARRFRDYYGTVFADYW (SEQ ID NO: 242) |
| 9G10 | QNVGTA (SEQ ID NO: 136) | SAS (SEQ ID NO: 24) | CQQYSSSPLTF (SEQ ID NO: 166) | GYTFNSYW (SEQ ID NO: 192) | IYPGSGST (SEQ ID NO: 217) | CARGLGRWFFDVW (SEQ ID NO: 243) |
| 10E1 | SSVSSSY (SEQ ID NO: 87) | GTS (SEQ ID NO: 160) | CQQYNGYPYTF (SEQ ID NO: 167) | GYAFSSSW (SEQ ID NO: 193) | IYPGDGDT (SEQ ID NO: 218) | CSREGDYYYGHFEYW (SEQ ID NO: 244) |
| 8E10 | QSLVHSNGNTY (SEQ ID NO: 137) | KVS (SEQ ID NO: 160) | CSQSTHVPWTF (SEQ ID NO: 168) | GFTFIDFG (SEQ ID NO: 194) | ISSGSSTV (SEQ ID NO: 219) | CARPELPYYAMDYW (SEQ ID NO: 245) |
| 10D6 | QSLVHSNGYTY (SEQ ID NO: 138) | KVS (SEQ ID NO: 160) | CSQSTHVPYTF (SEQ ID NO: 169) | GFTFSDFG (SEQ ID NO: 195) | ISSGSSTV (SEQ ID NO: 219) | CARPGLPYYYAMDYW (SEQ ID NO: 246) |
| 9B3 | QNVGSA (SEQ ID NO: 139) | LAS (SEQ ID NO: 22) | CQQYTSYPYTF (SEQ ID NO: 170) | GYTFTTYP (SEQ ID NO: 196) | FHPFNDYS (SEQ ID NO: 220) | CARLSNYGAWFPYW (SEQ ID NO: 247) |
| 18H2 | RDINGY (SEQ ID NO: 140) | RAN (SEQ ID NO: 99) | CLQYDEFLLTF (SEQ ID NO: 108) | GYTFTSYW (SEQ ID NO: 153) | IHPNGGST (SEQ ID NO: 123) | CARGLTGLFAYW (SEQ ID NO: 248) |
| 18B7 | SSVSSGY (SEQ ID NO: 141) | ITS (SEQ ID NO: 161) | CHQFHRSPFTF (SEQ ID NO: 171) | GYTFTGNW (SEQ ID NO: 197) | ILARSGNI (SEQ ID NO: 221) | CAKRRLLAMDDW (SEQ ID NO: 249) |

TABLE 3-continued

| Clone | variable Light (VL) chain CDR sequences ||| variable Heavy (VH) chain CDR sequences |||
|---|---|---|---|---|---|---|
| | CDR1 | CDR | CDR3 | CDR1 | CDR2 | CDR3 |
| P 8H5 | SSVSSSY (SEQ ID NO: 87) | STS (SEQ ID NO: 20) | CHQYHRSPFTF (SEQ ID NO: 100) | GYTFTGYW (SEQ ID NO: 198) | ILPGSIYI (SEQ ID NO: 222) | CAKRRLLSMDYW (SEQ ID NO: 250) |
| P 11G9 | SSVSSTY (SEQ ID NO: 142) | ITS (SEQ ID NO: 161) | CHQYHRSPYTF (SEQ ID NO: 172) | GYTFTGDW (SEQ ID NO: 199) | ILPGIGYT (SEQ ID NO: 223) | CARRLFYFDYW (SEQ ID NO: 251) |
| P 12B1 | QNVGTN (SEQ ID NO: 8) | SAS (SEQ ID NO: 24) | CQQYNSYPYTF (SEQ ID NO: 40) | GFNIKDYY (SEQ ID NO: 200) | IDAIDGET (SEQ ID NO: 224) | CGRGALFTTSLDYW (SEQ ID NO: 252) |
| P 8A4 | SSVSSSY (SEQ ID NO: 87) | GTS (SEQ ID NO: 95) | CQQYNGYPYTF (SEQ ID NO: 167) | GYAFSSSW (SEQ ID NO: 193) | IYPGDGDT (SEQ ID NO: 218) | CAREGDYYYGHFDYW (SEQ ID NO: 253) |
| P 11G4 | QSIVHSNGDTC (SEQ ID NO: 143) | KVS (SEQ ID NO: 160) | CSQSTHVPWTF (SEQ ID NO: 168) | GFSLTNYG (SEQ ID NO: 201) | IWGDGST (SEQ ID NO: 215) | CGKPNWDYYAMDYW (SEQ ID NO: 254) |
| P 4E5 | QSLLYSSYQKNY (SEQ ID NO: 144) | WAS (SEQ ID NO: 23) | CQQYYNPWTF (SEQ ID NO: 173) | GFTFSDYG (SEQ ID NO: 49) | ISSGSSTI (SEQ ID NO: 63) | CASDGYPYGMDYW (SEQ ID NO: 245) |
| P 7H3 | QGISNY (SEQ ID NO: 145) | YTS (SEQ ID NO: 19) | CQQYSKLPPTF (SEQ ID NO: 174) | GFTFSDFG (SEQ ID NO: 219) | ISSGSSTV (SEQ ID NO: 195) | CARPGLPYYYAMDYW (SEQ ID NO: 246) |
| P 18A12 | QDISDY (SEQ ID NO: 154) | YTS (SEQ ID NO: 19) | CQQGKTLPWTF (SEQ ID NO: 175) | GFTFSSYA (SEQ ID NO: 202) | ISSGGDYI (SEQ ID NO: 225) | CTRDRKEPYDSSYRYAMDYW (SEQ ID NO: 256) |
| CTAD 7B12 | QSLLNNSNQKNY (SEQ ID NO: 155) | FAS (SEQ ID NO: 18) | CQQHYSTPLTF (SEQ ID NO: 176) | GYTFINYY (SEQ ID NO: 50) | IYPGNVNS (SEQ ID NO: 119) | CAMTNSSAMDYW (SEQ ID NO: 81) |
| CTAD 6G9 | QNIRTA (SEQ ID NO: 10) | LAS (SEQ ID NO: 22) | CLQHWNYPFTF (SEQ ID NO: 38) | GYTFINYY (SEQ ID NO: 50) | IYPGNVNS (SEQ ID NO: 119) | CAMTNSSAMDYW (SEQ ID NO: 81) |
| CTAD 3C5 | QNIRTA (SEQ ID NO: 10) | LAS (SEQ ID NO: 22) | CLQHWNYPFTF (SEQ ID NO: 38) | GYTFINYY (SEQ ID NO: 50) | IYPGNVNS (SEQ ID NO: 119) | CAMTNSSAMDYW (SEQ ID NO: 81) |
| CTAD 9B2 | QNIRTA (SEQ ID NO: 10) | LAS (SEQ ID NO: 22) | CLQHWNYPFTF (SEQ ID NO: 38) | GYTFINYY (SEQ ID NO: 50) | IYPGNVNS (SEQ ID NO: 119) | CAMTNSSAMDYW (SEQ ID NO: 81) |

TABLE 3-continued

| Clone | variable Light (VL) chain CDR sequences | | | variable Heavy (VH) chain CDR sequences | | |
|---|---|---|---|---|---|---|
| | CDR1 | CDR | CDR3 | CDR1 | CDR2 | CDR3 |
| CTAD 12H11 | QNIRTA (SEQ ID NO: 10) | LAS (SEQ ID NO: 22) | CLQHWNYPFTF (SEQ ID NO: 38) | GYTFINYY (SEQ ID NO: 50) | IYPGNVNS (SEQ ID NO: 119) | CAMTNSSAMDYW (SEQ ID NO: 81) |
| CTAD 4A3 | QNIRTA (SEQ ID NO: 10) | LAS (SEQ ID NO: 22) | CLQHWNYPFTF (SEQ ID NO: 38) | GYTFINYY (SEQ ID NO: 50) | IYPGNVNS (SEQ ID NO: 119) | CAMTNSSAMDYW (SEQ ID NO: 81) |
| CTAD 5D12 | QNIRTA (SEQ ID NO: 10) | LAS (SEQ ID NO: 22) | CLQHWNYPFTF (SEQ ID NO: 38) | GYTFINYY (SEQ ID NO: 50) | IYPGNVNS (SEQ ID NO: 119) | CAMTNSSAMDYW (SEQ ID NO: 81) |
| CTAD 2E7 | QNIRTA (SEQ ID NO: 10) | LAS (SEQ ID NO: 22) | CLQHWNYPFTF (SEQ ID NO: 38) | GYTFINYY (SEQ ID NO: 50) | IYPGNVNS (SEQ ID NO: 119) | CAMTNSSAMDYW (SEQ ID NO: 81) |
| CTAD 1F5 | QNIRTA (SEQ ID NO: 10) | LAS (SEQ ID NO: 22) | CLQHWNYPFTF (SEQ ID NO: 38) | GYTFINYY (SEQ ID NO: 50) | IYPGNINS (SEQ ID NO: 64) | CAMTNSSAMDYW (SEQ ID NO: 81) |
| CTAD 2C10 | QNIRTA (SEQ ID NO: 11) | LAS (SEQ ID NO: 22) | CLQHWNYPFTF (SEQ ID NO: 38) | GYTFISYY (SEQ ID NO: 51) | IYPGNVNT (SEQ ID NO: 65) | CAMTNSSAMDYW (SEQ ID NO: 81) |
| CTAD 11B11 | QNIRTA (SEQ ID NO: 11) | LAS (SEQ ID NO: 22) | CLQHWNYPFTF (SEQ ID NO: 38) | GYTFISYY (SEQ ID NO: 51) | IYPGNVNT (SEQ ID NO: 65) | CAMTNSSAMDYW (SEQ ID NO: 81) |
| CTAD 3H7 | QNVRTA (SEQ ID NO: 11) | LAS (SEQ ID NO: 22) | CLQHWNYPFTF (SEQ ID NO: 38) | GYTFISYY (SEQ ID NO: 51) | IYPGNVNT (SEQ ID NO: 65) | CAMTNSSAMDYW (SEQ ID NO: 81) |
| CTAD 2G7 | QNVRSA (SEQ ID NO: 56) | LAS (SEQ ID NO: 22) | CLQHWNYPFTF (SEQ ID NO: 38) | GYTFISYY (SEQ ID NO: 51) | IYPGNVNT (SEQ ID NO: 65) | CAMTNSSAMDYW (SEQ ID NO: 81) |
| CTAD 3E9 | QNVRSA (SEQ ID NO: 56) | LAS (SEQ ID NO: 22) | CLQHWNYPFTF (SEQ ID NO: 38) | GYTFISYY (SEQ ID NO: 51) | IYPGNVNT (SEQ ID NO: 65) | CAMTNSSAMDYW (SEQ ID NO: 81) |
| CTAD 12C9 | QNVRTA (SEQ ID NO: 11) | LAS (SEQ ID NO: 22) | CLQHWNYPFTF (SEQ ID NO: 38) | GYTFISYY (SEQ ID NO: 52) | IYPGNVNT (SEQ ID NO: 65) | CAMTNSSAMDYW (SEQ ID NO: 81) |
| CTAD 3E8 | HNVRTA (SEQ ID NO: 156) | LAS (SEQ ID NO: 22) | CLQHWNYPFTF (SEQ ID NO: 38) | WLHLHKLL (SEQ ID NO: 203) | IYPGNVNT (SEQ ID NO: 65) | CAMTNSSAMDYW (SEQ ID NO: 81) |

TABLE 3-continued

| Clone | variable Light (VL) chain CDR sequences | | | variable Heavy (VH) chain CDR sequences | | |
|---|---|---|---|---|---|---|
| | CDR1 | CDR | CDR3 | CDR1 | CDR2 | CDR3 |
| CTAD 8E7 | QDISNY (SEQ ID NO: 7) | YTS (SEQ ID NO: 19) | CQQANTLPWTF (SEQ ID NO: 177) | GFSLSSYG (SEQ ID NO: 204) | IWAGKIT (SEQ ID NO: 226) | CARGGDYYGSSWYFDVW (SEQ ID NO: 257) |
| CTAD 12C5 | QGISNY (SEQ ID NO: 145) | YTS (SEQ ID NO: 19) | CQQFSKFPWTF (SEQ ID NO: 178) | GFSLTNYD (SEQ ID NO: 54) | IWAGGIT (SEQ ID NO: 227) | CARDRGSGSYYAMDYW (SEQ ID NO: 258) |
| CTAD 6F3 | ENIYSY (SEQ ID NO: 15) | NVK (SEQ ID NO: 162) | CQHHYGPPPTF (SEQ ID NO: 179) | GYTFTNYG (SEQ ID NO: 46) | INTNTGEP (SEQ ID NO: 228) | CARGGYSGYLYYFDYW (SEQ ID NO: 259) |
| CTAD 8F5 | ENVDRFGHNF (SEQ ID NO: 146) | RAS (SEQ ID NO: 26) | CQQSNEDPPTF (SEQ ID NO: 180) | GYSITDYT (SEQ ID NO: 205) | INPYNGRT (SEQ ID NO: 229) | CARGGDYYGSYYYFDYW (SEQ ID NO: 260) |
| CTAD 7G6 | ESVDSYGNSF (SEQ ID NO: 147) | RAS (SEQ ID NO: 26) | CQQCNEDPWTF (SEQ ID NO: 181) | GYTFTDYN (SEQ ID NO: 206) | IYPYNGGT (SEQ ID NO: 234) | CARSYANPYYAMDYW (SEQ ID NO: 261) |
| CTAD 8D8 | QNVRTA (SEQ ID NO: 11) | LAS (SEQ ID NO: 22) | CLQHWNYPFTF (SEQ ID NO: 38) | GYTFISYF (SEQ ID NO: 207) | IYPGNVNT (SEQ ID NO: 65) | CAVTNSSAMDFW (SEQ ID NO: 262) |
| CTAD 5H2 | KSVSSSGYSY (SEQ ID NO: 148) | LVS (SEQ ID NO: 163) | CQHIRELPWTF (SEQ ID NO: 182) | GFSLSTFGMG (SEQ ID NO: 208) | IYWDDDK (SEQ ID NO: 230) | CARI1ETAMDYW (SEQ ID NO: 263) |
| CTAD 4G7 | QSLLYSSNQKNY (SEQ ID NO: 13) | WAS (SEQ ID NO: 23) | CQQYYSYRTF (SEQ ID NO: 39) | GFSLTNYD (SEQ ID NO: 54) | IWTGGNT (SEQ ID NO: 66) | CVREGFRQGYYAMDYW (SEQ ID NO: 82) |
| CTAD 2G2 | SSLSSSY (SEQ ID NO: 149) | STS (SEQ ID NO: 20) | CHQYHRSPFTF (SEQ ID NO: 100) | GFSFSDYY (SEQ ID NO: 209) | ISDGGDYT (SEQ ID NO: 231) | CARDRHSGTYAMDYW (SEQ ID NO: 264) |
| CTAD 9D1 | ENIYSN (SEQ ID NO: 150) | AAT (SEQ ID NO: 21) | CQHFWGTPYTF (SEQ ID NO: 183) | GYSITSGYY (SEQ ID NO: 112) | ISYDGTN (SEQ ID NO: 232) | CARERGIYSGNYVYYFDYW (SEQ ID NO: 265) |
| CTAD 5H6 | SSVSSSY (SEQ ID NO: 87) | STS (SEQ ID NO: 20) | CHQYHRSPFTF (SEQ ID NO: 100) | GFTFSDYY (SEQ ID NO: 210) | ISDGGNYT (SEQ ID NO: 223) | CARETLPSYYAMDYW (SEQ ID NO: 266) |
| CTAD 1E10 | ESVDSYGNSF (SEQ ID NO: 147) | RAS (SEQ ID NO: 26) | CQQSNEDPLTF (SEQ ID NO: 184) | GYTFTDYN (SEQ ID NO: 206) | IYPYNGGT (SEQ ID NO: 234) | CARNDEGDSLTVYYFVMDYW (SEQ ID NO: 267) |

TABLE 3-continued

| Clone | variable Light (VL) chain CDR sequences | | | variable Heavy (VH) chain CDR sequences | | |
|---|---|---|---|---|---|---|
| | CDR1 | CDR | CDR3 | CDR1 | CDR2 | CDR3 |
| CTAD 12B2 | QSVTTSDYSY (SEQ ID NO: 151) | LAS (SEQ ID NO: 22) | CQNSRECPSWF (SEQ ID NO: 185) | GDSITSGH (SEQ ID NO: 211) | ISYSGST (SEQ ID NO: 235) | CARSRYDGYYPAWLAYW (SEQ ID NO: 268) |
| CTAD 7E6 | ENIYSN (SEQ ID NO: 150) | AAT (SEQ ID NO: 21) | CQHFWGSPYTF (SEQ ID NO: 186) | GYSITSGSY (SEQ ID NO: 212) | ISYDGSN (SEQ ID NO: 120) | CTREREIYSGNYVYFFDYW (SEQ ID NO: 269) |
| CTAD 8B6 | KNIYSN (SEQ ID NO: 152) | AAT (SEQ ID NO: 21) | CQHFWGTPLTF (SEQ ID NO: 187) | GYTFSSYW (SEQ ID NO: 213) | ILPGTGDS (SEQ ID NO: 236) | CTRSKRYGNYYAMDYW (SEQ ID NO: 270) |
| CTAD 1E12 | QSLLDSDGKTY (SEQ ID NO: 153) | LVS (SEQ ID NO: 163) | CWQGTHLYTF (SEQ ID NO: 188) | GFTFSDAW (SEQ ID NO: 214) | IRSKAHNHVT (SEQ ID NO: 237) | CTRTTGYAMDYW (SEQ ID NO: 271) |
| CTAD 6A10 | QGISNY (SEQ ID NO: 145) | YTS (SEQ ID NO: 19) | CQQFSKLPWTF (SEQ ID NO: 189) | GFSLTSYG (SEQ ID NO: 190) | IWAGGNT (SEQ ID NO: 238) | CVRDRGTARAYYAMDYW (SEQ ID NO: 272) |

Although the above Tables discloses the CDRs according to Kabat (Kabat et al., Sequences of Proteins of Immunological Interest, 5th Ed. Public Health Service, National Institutes of Health, Bethesda, Md. (1991)), the antibodies of this disclosure can comprise CDRs according to any CDR definition (e.g., Kabat, Chothia, enhanced Chothia, contact, IMGT, AbM). The CDRs of an antibody according to the different CDR definitions can be determined, e.g., by using the AbYsis database.

In certain embodiments, these antibodies or antigen-binding fragments thereof have at least one, at least two, at least three, at least four, at least five, or all six of the CDRs of as disclosed in Tables 1 and 2 (wherein the CDRs can be according to any CDR definition).

The $V_H$ and or $V_L$ region of the anti-LILRB3 antibodies or antigen-binding fragments thereof described herein can be linked to a constant region (e.g., a wild-type human Fc region or an Fc region that includes one or more alterations). In some embodiments, the antibody has a light chain constant region derived from a human kappa sequence. In some embodiments, the antibody has a light chain constant region derived from a human lambda sequence. In a specific embodiment, the light chain constant region comprises a human subgroup kappa 1 sequence. In certain embodiments, the antibody has an isotype selected from the group consisting of IgG 1, IgG2, IgG3, and IgG4. The heavy chain constant region can be a wild-type human Fc region, or a human Fc region that includes one or more amino acid substitutions. The antibodies can have mutations that stabilize the disulfide bond between the two heavy chains of an immunoglobulin, such as mutations in the hinge region of IgG4, as disclosed in the art (e.g., Angal et al, Mol. Immunol, 30: 105-08 (1993)). See also, e.g., U.S. 2005/0037000. The heavy chain constant region can also have substitutions that modify the properties of the antibody (e.g., decrease one or more of: Fc receptor binding, antibody glycosylation, deamidation, binding to complement, or methionine oxidation). In some instances, the antibodies may have mutations such as those described in U.S. Pat. Nos. 5,624,821 and 5,648,260. In some embodiments, the antibody is modified to reduce or eliminate effector function. In some embodiments, the heavy chain constant region has one or more of the following mutations: S228P; N297Q; and T299A (numbering according to Kabat). The heavy chain constant region can be chimeric, e.g., the Fc region can comprise the CHI and CH2 domains of an IgG antibody of the IgG4 isotype, and the CH3 domain from an IgG antibody of the IgG1 isotype (see, e.g., U.S. Patent Appl. No. 2012/0100140A1 which is incorporated by reference in its entirety herein). In a specific embodiment, the humanized anti-LILRB3 antibodies described herein have a chimeric constant region comprising the CHI and CH2 domains of an IgG antibody of the IgG4 isotype, and the CH3 domain from an IgG antibody of the IgGl isotype and further contain the S228P and N297Q mutations (numbering according to Kabat).

Antigen-binding fragments of the anti-LILRB3 antibodies are also encompassed by this disclosure. In some embodiments, the anti-LILRB3 antibody or antigen-binding molecule thereof comprises or consists of (i) a single chain Fv ("scFv"); (ii) a diabody; (iii) an sc(Fv)2; (iv) a polypeptide chain of an antibody; (v) F(ab')2; or (vi) F(ab). In one embodiment, the antigen-binding fragment is an Fab molecule. The fragment antigen-binding (Fab fragment) is a region on an antibody that binds to antigens. It is composed of one constant and one variable domain of each of the heavy and the light chain. These domains shape the paratope, i.e., the antigen-binding site. The enzyme papain can be used to cleave an immunoglobulin monomer into two Fab fragments and an Fc fragment. Recombinant methods can also be used to make an Fab molecule. In another embodiment, the antigen-binding fragment is a single-chain fragment variable (scFv). An scFv is comprised of the variable regions of the heavy and light chains of an antibody. It is only half the size of the Fab fragment and yet retains the original specificity of the parent immunoglobulin. Methods of making an ScFv are well known in the art (see, e.g., Ahmad et al, Clinical and Developmental Immunology, vol. 2012, Article ID 980250, 15 pages, 2012. doi: 10.1 155/2012/980250).

In certain embodiments, the anti-LILRB3 antibody or antigen-binding molecule thereof can be a targeting moiety. These targeting moieties are useful in ferrying an agent of interest (e.g., a therapeutic agent, a small molecule drug) to a cell.

The present disclosure also provides "chimeric molecules" comprising, for example, at least one of the LILRB3 antibodies or antigen-binding fragments thereof disclosed herein that is linked and/or conjugated and/or otherwise associated with at least one heterologous moiety. In certain embodiments, the heterologous moiety is an agent that to be ferried or delivered to a cell or its local environment. Such an agent can be e.g., a therapeutic agent such as a chemotherapeutic agent. A chimeric molecule disclosed herein encompasses any molecule comprising (i) a LILRB3 antibody or antigen-binding molecule thereof disclosed herein (e.g., an Fab or scFv), and (ii) at least one (e.g., one two, three, four) heterologous moiety (e.g., a therapeutic moiety, a chemotherapeutic agent, a half-life extending moiety) and optionally including one or more linkers. In some embodiments, a chimeric molecule is a chimeric protein, i.e., a chimeric molecule in which all its components (heterologous moieties and/or linkers) are polypeptides. Other chimeric molecules can comprise non-polypeptide heterologous moieties (e.g., PEG, lipids, carbohydrates, nucleic acids, small molecule therapeutic agents, radionuclides, fluorescent probes, etc.) and/or non-polypeptide linkers.

In some embodiments, a chimeric molecule comprises a first amino acid sequence derived from a first source, bonded, covalently or non-covalently, to a second amino acid sequence derived from a second source, wherein the first and second source are not the same. A first source and a second source that are not the same can include two different biological entities, or two different proteins from the same biological entity, or a biological entity and a non-biological entity. A chimeric molecule can include for example, a protein derived from at least two different biological sources. A biological source can include any non-synthetically produced nucleic acid or amino acid sequence (e.g., a genomic or cDNA sequence, a plasmid or viral vector, a native virion or a mutant or analog, as further described herein, of any of the above). A synthetic source can include a protein or nucleic acid sequence produced chemically and not by a biological system (e.g., solid phase synthesis of amino acid sequences). A chimeric molecule can also include a protein derived from at least 2 different synthetic sources or a protein derived from at least one biological source and at least one synthetic source. A chimeric molecule can also comprise a first amino acid sequence derived from a first source, covalently or non-covalently linked to a nucleic acid, derived from any source or a small organic or inorganic molecule derived from any source. The chimeric molecule can also comprise a linker molecule between the first and second amino acid sequence or between the first amino acid sequence and the nucleic acid, or between the first amino acid sequence and the small organic or inorganic molecule.

The heterologous moiety or moieties of the chimeric molecules disclosed herein can comprise, consist of, or consist essentially of, for example, prophylactic and/or therapeutic agents (e.g., chemotherapeutic agent or analgesic), molecules capable of improving a pharmacokinetic (PK) property (e.g., plasma half-life extending moieties), and detectable moieties (e.g., fluorescent molecules or radionuclides). In some embodiments, the heterologous moiety comprises a clotting factor (e.g., a Factor VII). In some embodiments, a heterologous moiety comprises a molecule that can modify a physicochemical property of a chimeric molecule lacking such heterologous moiety. In other embodiments, the incorporation of a heterologous moiety into a chimeric molecule can improve one or more pharmacokinetic properties without significantly affecting its biological activity or function. In other embodiments, a heterologous moiety increases stability of the chimeric molecule of the invention or a fragment thereof.

In some embodiments, the heterologous moiety is a polypeptide comprising, consisting essentially of, or consisting of at least about 10, 100, 200, 300, 400, 500, 600, 700, 800, 900, 1000, 1100, 1200, 1300, 1400, 1500, 1600, 1700, 1800, 1900, 2000, 2500, 3000, or 4000 amino acids. In other embodiments, the heterologous moiety is a polypeptide comprising, consisting essentially of, or consisting of about 100 to about 200 amino acids, about 200 to about 300 amino acids, about 300 to about 400 amino acids, about 400 to about 500 amino acids, about 500 to about 600 amino acids, about 600 to about 700 amino acids, about 700 to about 800 amino acids, about 800 to about 900 amino acids, or about 900 to about 1000 amino acids.

In some embodiments, the chimeric molecule comprises at least one heterologous moiety that is a "half-life extending moiety." Half-life extending moieties can comprise, for example, (i) XTEN polypeptides; (ii) Fc; (iii) albumin, (iv) albumin binding polypeptide or fatty acid, (v) the C-terminal peptide (CTP) of the β subunit of human chorionic gonadotropin, (vi) PAS; (vii) HAP; (viii) transferrin; (ix) polyethylene glycol (PEG); (x) hydroxyethyl starch (HES), (xi) polysialic acids (PSAs); (xii) a clearance receptor or fragment thereof which blocks binding of the chimeric molecule to a clearance receptor; (xiii) low complexity peptides; (xiv) vWF; or (xv) any combinations thereof. In some embodiments, the half-life extending moiety comprises an Fc region. In other embodiments, the half-life extending moiety comprises two Fc regions fused by a linker. Exemplary heterologous moieties also include, e.g., FcRn binding moieties (e.g., complete Fc regions or portions thereof which bind to FcRn), single chain Fc regions (scFc regions, e.g., as described in U.S. Publ. No. 2008-0260738, and Intl. Publ. Nos. WO 2008-012543 and WO 2008-1439545), or processable scFc regions. In some embodiments, a heterologous moiety can include an attachment site for a non-polypeptide moiety such as polyethylene glycol (PEG), hydroxyethyl starch (HES), polysialic acid, or any derivatives, variants, or combinations of these moieties.

In certain embodiments, a chimeric molecule of the disclosure comprises at least one (e.g., one, two, three, or four) half-like extending moiety which increases the in vivo half-life of the chimeric molecule compared with the in vivo half-life of the corresponding chimeric molecule lacking such heterologous moiety. In vivo half-life of a chimeric molecule can be determined by any method known to those of skill in the art, e.g., activity assays (chromogenic assay or one stage clotting aPTT assay), ELISA, etc. In some embodiments, the presence of one or more half-life extending moiety results in the half-life of the chimeric molecule to be increased compared to the half-life of the corresponding chimeric molecule lacking such one or more half-life extending moieties. The half-life of the chimeric molecule comprising a half-life extending moiety is at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the in vivo half-life of the corresponding chimeric molecule lacking such half-life extending moiety.

In one embodiment, the half-life of the chimeric molecule comprising a half-life extending moiety is about 1.5-fold to about 20-fold, about 1.5 fold to about 15 fold, or about 1.5 fold to about 10 fold longer than the in vivo half-life of the corresponding chimeric molecule lacking such half-life extending moiety. In another embodiment, the half-life of chimeric molecule comprising a half-life extending moiety is extended about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 2.5-fold to about 10-fold, about 2.5-fold to about 9-fold, about 2.5-fold to about 8-fold, about 2.5-fold to about 7-fold, about 2.5-fold to about 6-fold, about 2.5-fold to about 5-fold, about 2.5-fold to about 4-fold, about 2.5-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-fold to about 6 fold, about 5-fold to about 7-fold, or about 6-fold to about 8 fold as compared to the in vivo half-life of the corresponding chimeric molecule lacking such half-life extending moiety.

Characterization of Antibodies

The LILRB3 binding properties of the antibodies described herein may be measured by any standard method, e.g., one or more of the following methods: OCTET®, Surface Plasmon Resonance (SPR), BIACORE™ analysis, Enzyme Linked Immunosorbent Assay (ELISA), EIA (enzyme immunoassay), RIA (radioimmunoassay), and Fluorescence Resonance Energy Transfer (FRET).

The binding interaction of a protein of interest (an anti-LILRB3 antibody or functional fragment thereof) and a target (e.g., LILRB3) can be analyzed using the OCTET® systems. In this method, one of several variations of instruments (e.g., OCTET® QKe and QK), made by the ForteBio company are used to determine protein interactions, binding specificity, and epitope mapping. The OCTET® systems provide an easy way to monitor real-time binding by measuring the changes in polarized light that travels down a custom tip and then back to a sensor.

The binding interaction of a protein of interest (an anti-LILRB3 antibody or functional fragment thereof) and a target (e.g., LILRB3) can be analyzed using Surface Plasmon Resonance (SPR). SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which is measured as an indication of real-time reactions between biological molecules. Methods for using SPR are described, for example, in U.S. Pat. No.

5,641,640; Raether (1988) Surface Plasmons Springer Verlag; Sjolander and Urbaniczky (1991) Anal. Chem. 63:2338-2345; Szabo et al. (1995) Curr. Opin. Struct. Biol. 5:699-705 and on-line resources provide by BIAcore International AB (Uppsala, Sweden). Information from SPR can be used to provide an accurate and quantitative measure of the equilibrium dissociation constant (Kd), and kinetic parameters, including Kon and Koff, for the binding of a biomolecule to a target.

Epitopes can also be directly mapped by assessing the ability of different anti-LILRB3 antibody or functional fragment thereof to compete with each other for binding to human LILRB3 using BIACORE chromatographic techniques (Pharmacia BIAtechnology Handbook, "Epitope Mapping", Section 6.3.2, (May 1994); see also Johne et al. (1993) J. Immunol. Methods, 160:191-198).

When employing an enzyme immunoassay, a sample containing an antibody, for example, a culture supernatant of antibody-producing cells or a purified antibody is added to an antigen-coated plate. A secondary antibody labeled with an enzyme such as alkaline phosphatase is added, the plate is incubated, and after washing, an enzyme substrate such as p-nitrophenylphosphate is added, and the absorbance is measured to evaluate the antigen binding activity.

Additional general guidance for evaluating antibodies, e.g., Western blots and immunoprecipation assays, can be found in Antibodies: A Laboratory Manual, ed. by Harlow and Lane, Cold Spring Harbor press (1988)).

Figure 2C:
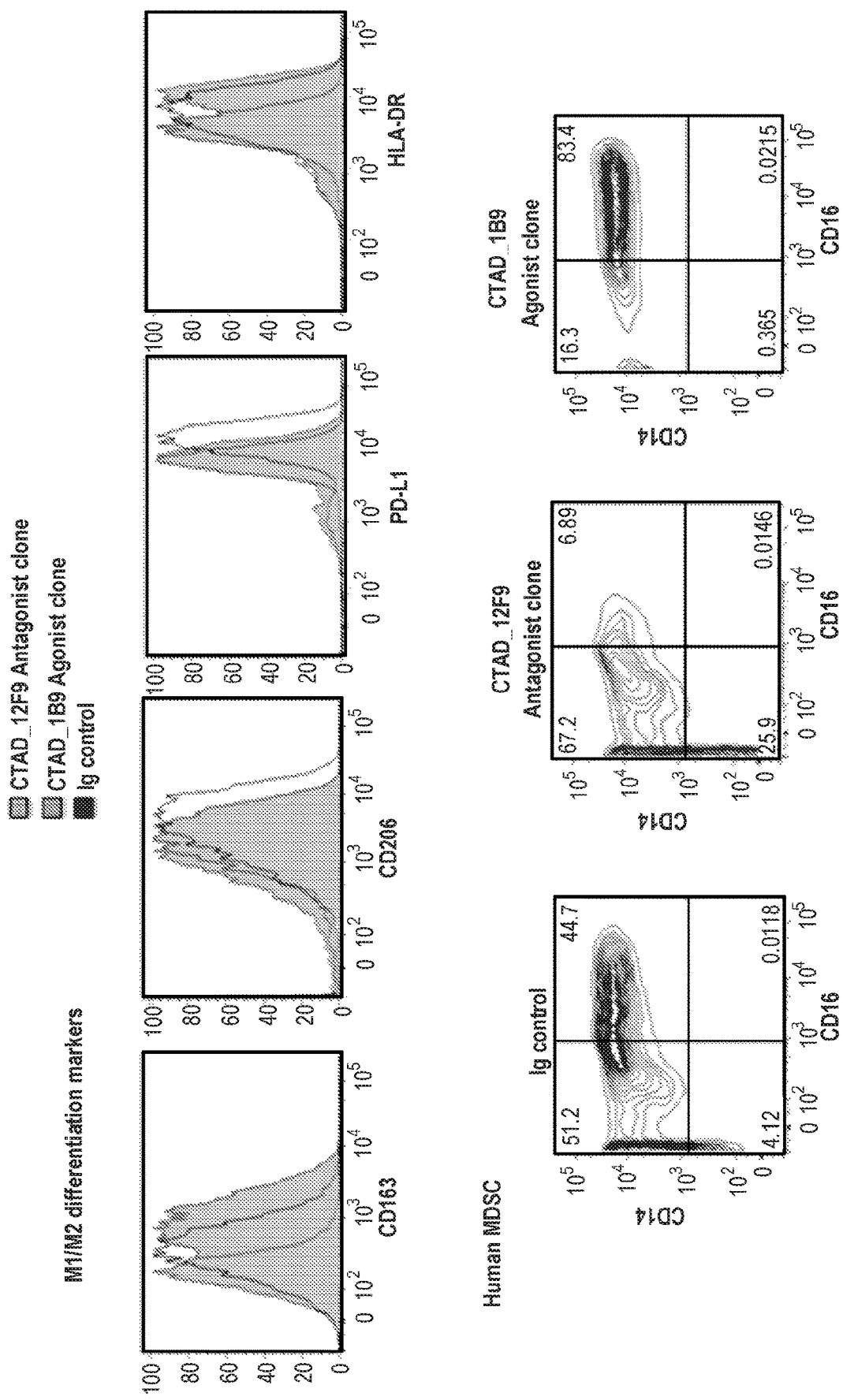
FIG. 2C is the flow cytometric analysis on the human CD33+CD14+CD16+ MDSC population (lower panel) and M1/M2 markers (upper panel) under treatments of antagonistic (CTAD_12F9) or agonistic antibodies (CTAD_1B9). Monocyte-derived macrophages (MDM) were differentiated from CD33+ myeloid cells sorted from healthy donor in the presence of M-CSF 50 ng/ml for 5 days. MDM were then cultured with interferon gamma (50 ng/ml, M1-polarization condition) plus antagonistic and agonistic anti-LILRB3 Ab (5 ug/ml) for 2 days. The test cells were harvested for cytometric analysis.
Figure 3A:
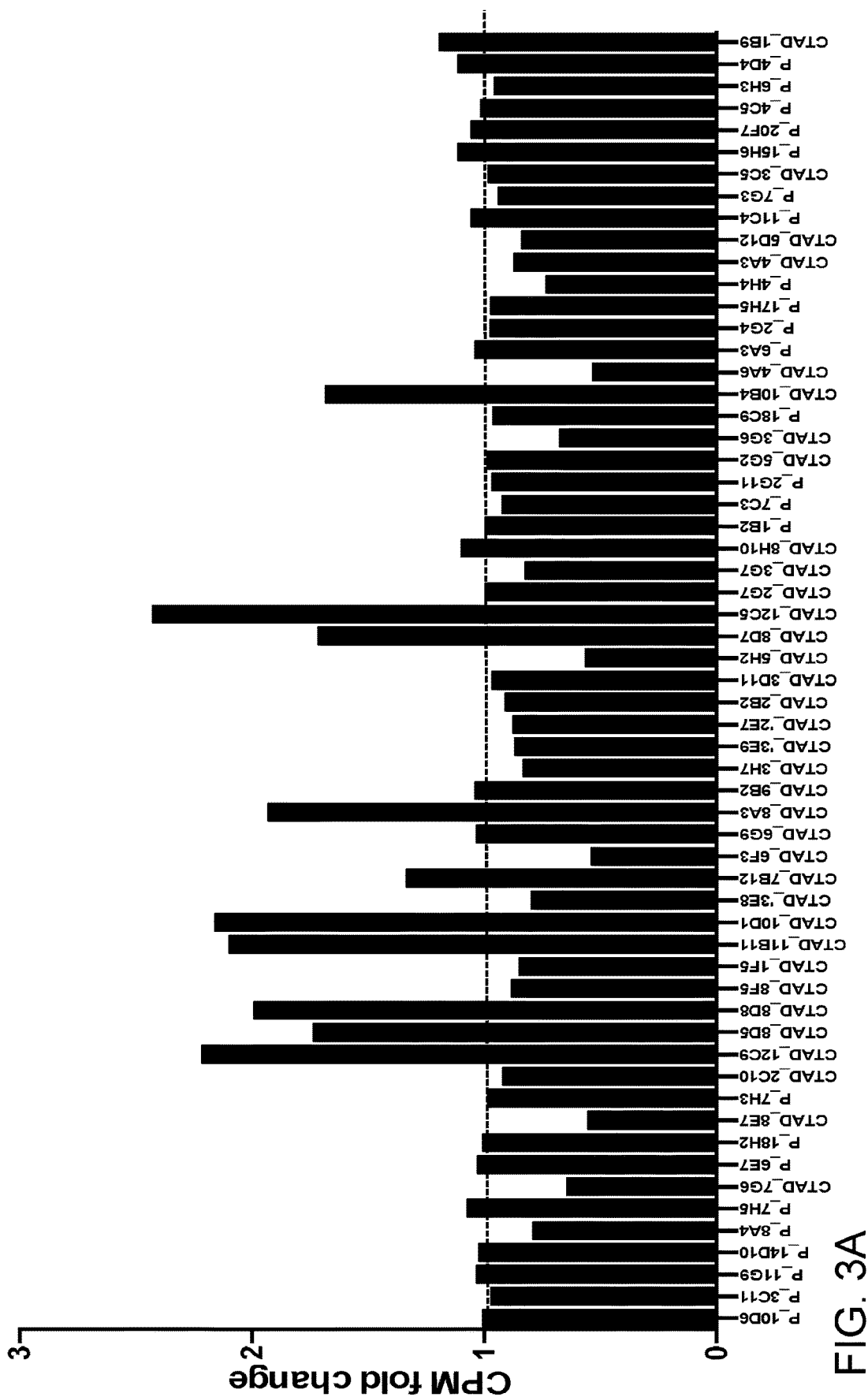
FIG. 3A is a graph showing OKT3-mediated T cell proliferation (CPM) following stimulation of PBMC from healthy donors with a low dose (0.3 µg/ml) anti-CD3 (OKT3) in the presence of anti-LILRB3 mAb supernatants or purified mAbs (5 µg/ml). After 3 day of treatment, T cells proliferation was assessed by [3H]-thymidine incorporation. Thymidine was added for the last 8 hrs of culture followed by measurement on a scintillation counter. Clone ranking based on TNF alpha from FIG. 1 is presented. The relative fold change in T-cell proliferation (CPM) is shown in FIG. 3A.
Figure 3B:
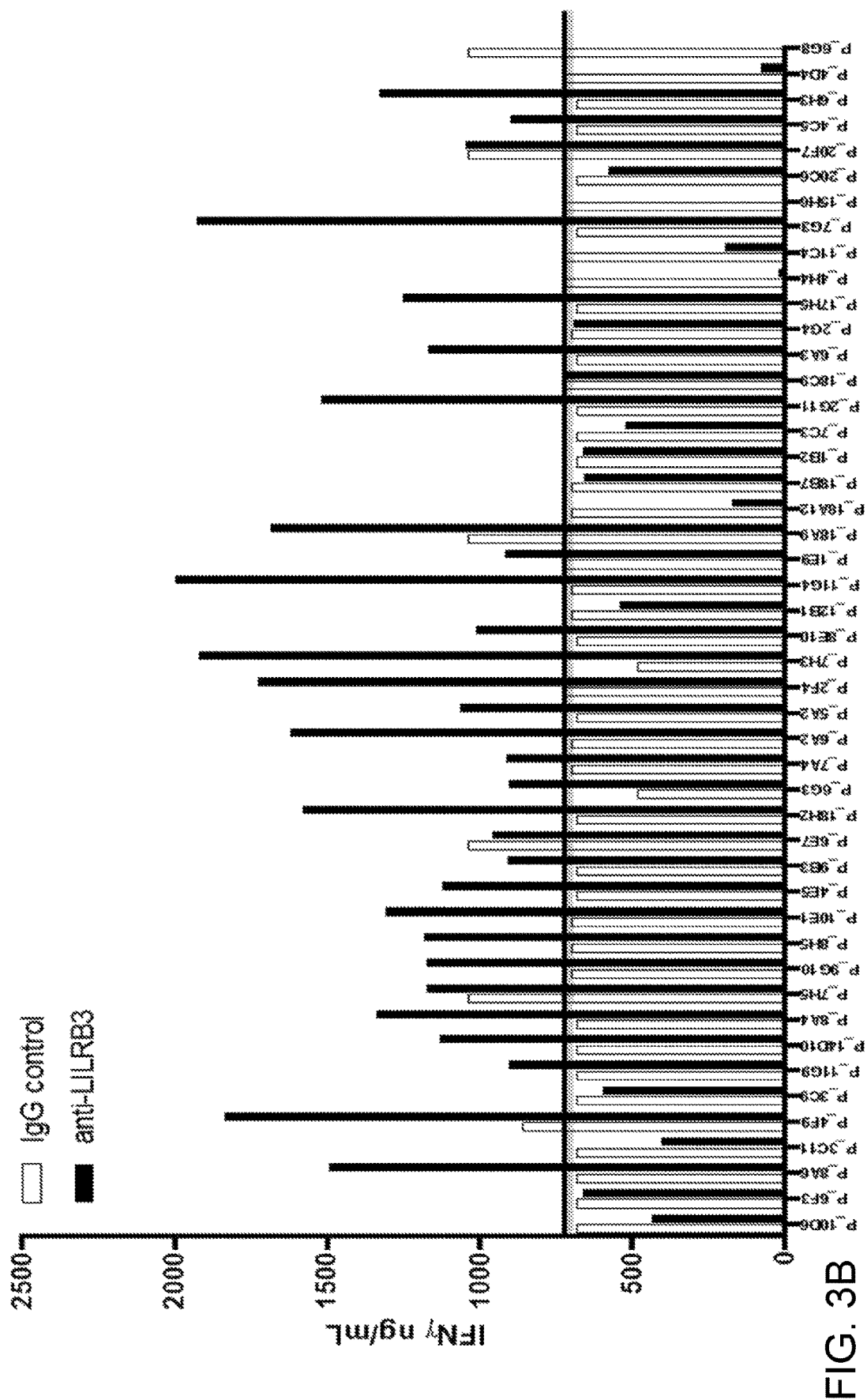
FIG. 3B is a graph showing IFN-γ production from human PBMCs from healthy donors following treatment with anti-LILRB3 hybridoma supernatant or purified antibody (5 µg/ml), or isotype control for 24 hours followed by stimulation with LPS (100 ng/ml) for 6 hours. Supernatants were collected and IFN-γ concentrations were measured by ELISA
Figure 3C:
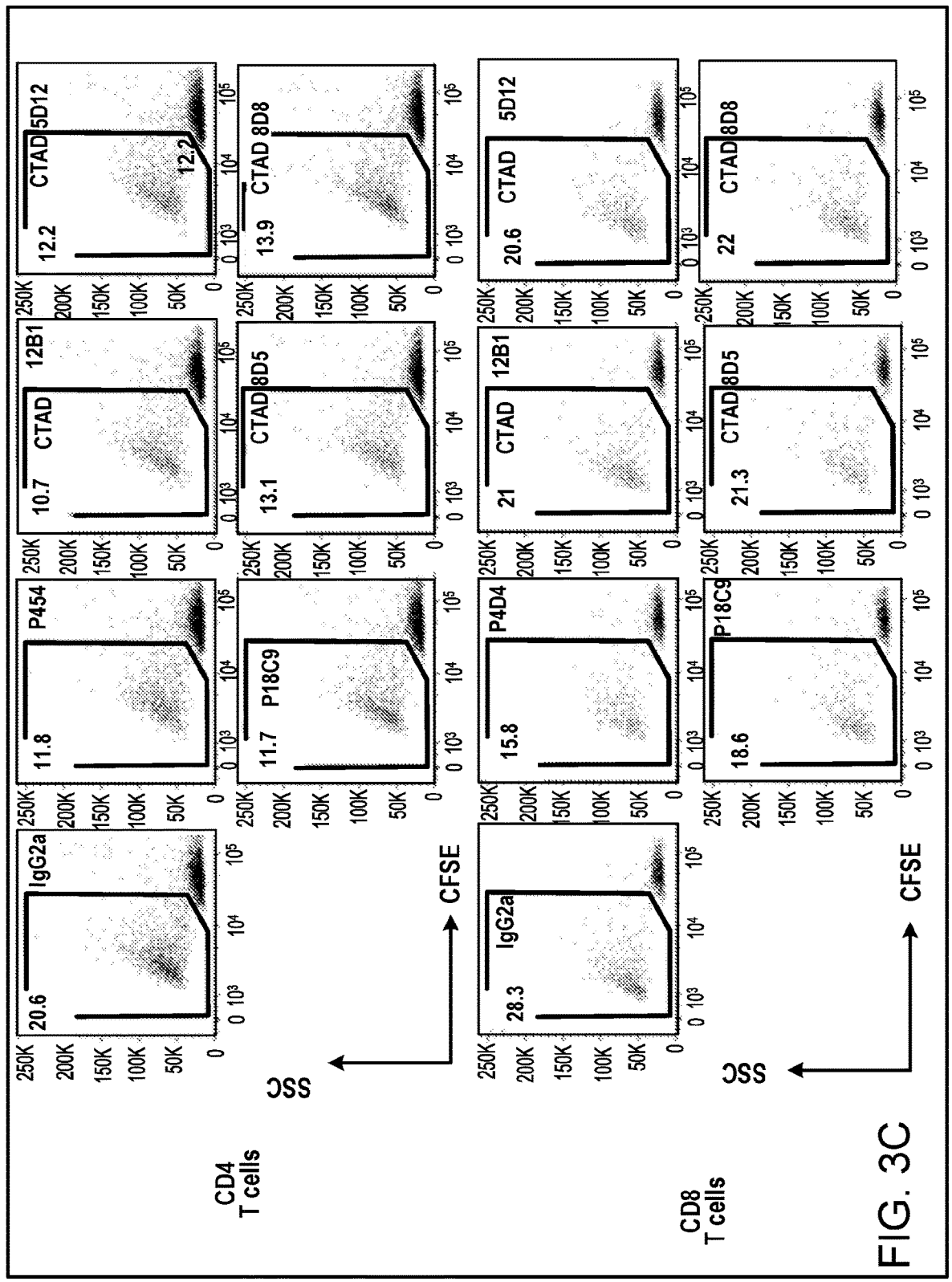
FIG. 3C is a set of flow cytometric data from cultured purified human T cells (responders) labeled with CFSE, and stimulated with irradiated (30 Gy) unrelated donor PBMCs (stimulators) in presence of IgG isotype control or the indicated LILRB3 antibodies (5 µg/ml). The ratio of responder/stimulator is 1/3. After 5 days of co-culture, viable CD4 T cells (upper panel) and CD8 T cells (lower panel) were analyzed by flow cytometry. The representative flow plots were showed as CFSE dilution and percent divided cells.
Figure 8:
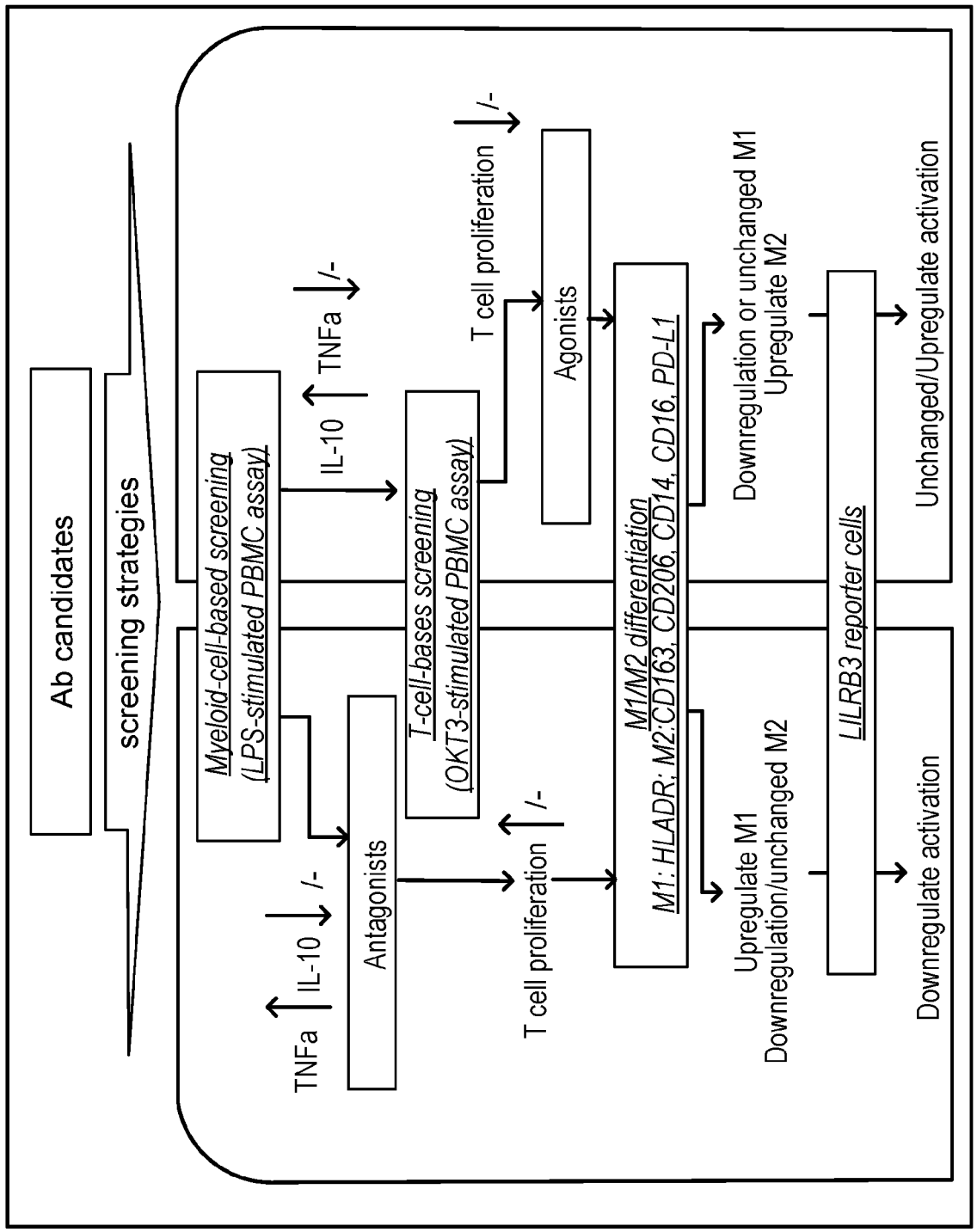
FIG. 8 is a flow chart demonstrating criteria for identifying LLRIB3 antagonists and agonists.

For characterization of antagonistic and agonistic bioactivity of antibodies, the inventors performed the LPS-stimulated PBMC (top priority, majorly targeting to myeloid cells) and OKT3-stimulated PBMC (majorly targeting to T cells) as pilot screening strategies. As shown in FIG. 8, which provides a flow chart with criteria for identifying LLRIB3 antagonists and agonists, the antagonistic Abs can increase TNFa along with decreased/unchanged IL-10 secretion, meanwhile, increased/unchanged T cell proliferation (TNFa>1.5 fold, IL-10<1.1 fold). On the other hand, agonistic Abs can increase IL-10 secretion together with decreased/unchanged TNFa secretion, meanwhile, decreased T cell proliferation (IL-10>1.2 fold, TNFa<1.1 fold and T cell proliferation<0.8 fold). The effects of Ab candidates on LPS- and OKT3-stimulated PBMC were shown in Table 3-6. Noteworthy that antagonistic and agonistic bioactivity of Ab candidates screened from T cell-based assays majority are consistent, but few may not consistent with that from myeloid cell-based assays. Besides, the Ab candidates were subjected to test LILRB3 reporter assay, M1/M2 differentiation/human MDSC markers by CD163, CD206, HLA-DR, PD-L1 and CD14, CD16 (FIG. 2C) as well as mix lymphocytes reaction (FIG. 3C). The antagonists can decrease the M2 differentiation (down-regulated CD163, CD206, PD-L1), increase HLA-DR and decrease human MDSC CD33+CD14+CD16+, in contrast, the agonists can counter-regulate or maintain above parameters. These assay provided very important parameters to decide the activity or compare the efficiency/potency of Ab candidates.

Additional Agents

MDSCs

MDSCs have recently been recognized as one of the central regulators of the immune system. MDSCs represent a heterogeneous population of cells of myeloid origin that include myeloid progenitors, immature macrophages, immature granulocytes, and immature dendritic cells. MDSCs differentiate and polarize into Gr1$^+$CD11b$^+$CD115$^+$Ly6C$^+$ monocytic (M)-cells and Gr1$^+$CD11b$^+$Ly6G$^+$ granulocytic (G)-cells in mice (Gabrilovich et al., *Cancer Res.* 67:425, 2007; Huang et al., *Cancer Res.* 66:1123-1131, 2006; Movahedi et al., *Blood* 111:4233-4244, 2008). Human MDSCs are characterized as CD11b+CD14$^{Low}$CD33$^+$ or Lin$^-$HLA$^-$DR$^{low-}$CD33$^+$ myeloid cells (Ostrand-Rosenberg et al., *J Immunol.* 182:4499-4506, 2009; Raychaudhuri et al., *Neurol. Oncol.* 13:591-599, 2011). Mirroring the nomenclature of type 1 classical activation-like (M1) and type 2 alternative activation-like (M2) macrophages, MDSCs can be differentiated and polarized into M1- and M2-cells (M1-cells expressing iNOS, TNF-α, IFN-gR, MHC class I, and CCR7, and M2-cells expressing arginase, IL-10, CD36, CD206, and CCR2). Tumor-associated MDSCs exhibit predominantly M2-like phenotypes with pro-tumoral and immunosuppressive activities. M2-cells are phenotypically characterized by a number of enhanced signature markers such as IL-10, arginase, IL-10, Tie-2, CD36, CD206, IL-4R and CCR2 (Ma et al., *Immunity* 34:385-395, 2011). M1-cells have an elevation in the expression of iNOS, NO, TNF-α, IFN-γR, MHC I, and CCR7 (Ma et al., *Immunity* 34:385-395, 2011). G2-cells up-regulate the expression of arginase, CCL2, CCL5 and MMP-9. In contrast, G1-cells show elevated expression levels of TNF-α, Fas, and ICAM-1.

MDSCs exert immune suppression through cross-communication with T-cells, NK cells, dendritic cells, macrophages, and other immune cells via multiple mechanisms. The details of how MDSC cross-talk with other immune cells are described in Bunt et al. (*J. Leukoc. Biol.* 85:996-1004, 2009), Ostrand-Rosenberg et al. (*Nat. Rev. Immunol.* 12:253-268, 2012), and Sinha et al. (*J Immunol.* 179:977-983, 2007). As far as T-cells are concerned, MDSCs can induce effector T-cell (Teff) inactivation and apoptosis (see, e.g., Apolloni et al., *J. Immunol.* 165:6723-6730, 2000) and expand regulatory T cells (Treg) (see, e.g., Adeegbe et al., *Cell Transplant.* 20:941-954, 2011). The regulation of T-cell suppression and Treg expansion by MDSC is cell contact-, MHC class II-, NO- and/or arginase-dependent. M2-cells possess an enhanced ability to suppress Teff activation and proliferation compared to their M1-like counterparts in co-cultures of T-cells (Ma et al., *Immunity* 34:385-395, 2011). M2-cells possess higher potency in Treg expansion than M1-cells, both in vitro and in vivo (Ma et al., *Immunity* 34:385-395, 2011). M2-cell-induced increase in Treg cells appears to be IL-10-, IL-4-, and IL-13-mediated and arginase-dependent (Ma et al., *Immunity* 34:385-395, 2011). Akin to the functionalities of M1/M2 cells, G1- and G2-cells possess anti-tumoral and pro-tumoral activities, respectively (Fridlender et al., *Cancer Cell* 16:183-194, 2009).

Polarization of MDSC subsets from one phenotype to the other is accompanied by functional changes. M2-cells accelerate tumor growth mainly by enhanced immune suppression involving an increase in arginase and immunosuppressive cytokines (see, e.g., Ma et al., *Immunity* 34:385-395, 2011). M1-cells have increased direct tumor killing and promote the development of anti-tumoral immunity through the augmentation of free radicals, death ligand, and immunostimulating cytokines (see, e.g., Ma et al., *Immunity* 34:385-395, 2011). The balance of M1/M2 polarization may have a significant influence on disease and health.

Methods of preparing and isolating MDSCs are known in the art. For example, MDSCs can be isolated using fluorescence-assisted cell sorting using antibodies that recognize any of the specific protein markers of the different MDSC subsets described herein. Exemplary methods for preparing and isolating MDSCs are described in U.S. Patent Application Publication No. 2008/0305079 and WO 11/087795 (each of which is herein incorporated by reference).

Mobilizing Agents

In some embodiments, the compositions further contain one or more mobilizing agents. Mobilizing agents stimulate the release of MDSCs from the bone marrow of a mammal. Non-limiting examples of mobilizing agents include, for example, granulocyte colony stimulating factor (G-CSF), cyclophosphamide, AMD3100, Fms-like tyrosine kinase 3 ligand (Flt3-L), GM-CSF, M-CSF, IL-34, TSLP-1, SCF, FK560, S100 A8, and S100 A9.

In some embodiments, the disclosure provides a composition containing a mobilizing agent and at least one LILRB1, LILRB2, LILRB3, LILRB4, and/or LILRB5 agonist. In some embodiments, a composition contains a mobilizing agent, at least one LILRB1, LILRB2, LILRB3, LILRB4, and/or LILRB5 agonist, and at least one JNK inhibitor. In some embodiments, the disclosure provides a composition further containing a mobilizing agent and does not include MDSCs.

JNK Inhibitors

In some embodiments, the compositions further contain at least one JNK inhibitor. Non-limiting examples of JNK inhibitors include, for example, BI-78D3, SP600125, AEG 3482, JIP-1, SU 3327, TCS JNK 5a, and TCS JNK 6o. Additional examples of JNK inhibitors are described in WO 00/35906, WO 00/35909, WO 00/35921, WO 00/64872, WO 01/12609, WO 01/12621, WO 01/23378, WO 01/23379, WO 01/23382, WO 01/47920, WO 01/91749, WO 02/046170, WO 02/062792, WO 02/081475, WO 02/083648, and WO 03/024967, each of which are herein incorporated by reference.

Anti-Inflammatory Agents

In some instances, the composition can also contain one or more anti-inflammatory agents. Anti-inflammatory agents include, for example, corticosteroids, non-steroidal anti-inflammatory drugs (NSAIDs, e.g., cyclooxygenase I (COX I) inhibitors and cyclooxygenase II (COX-II) inhibitors), immune selective anti-inflammatory derivatives (ImSAIDs), and biologics. Any of the exemplary anti-inflammatory agents described herein or known in the art can be included in the compositions described herein.

Non-limiting examples of NSAIDs are salicylates (e.g., aspirin, diflusinal, and salsalate), propionic acid derivatives (e.g., ibuprofen, dexiboprofen, naproxen, fenoprofen, ketoprofen, dexketoprofen, flurbiprofen, oxaprozin, and loxoprofen), acetic acid derivatives (e.g., indomethacin, sulindac, etodolac, ketorolac, diclofenac, and nabumetone), enolic acid derivatives (e.g., piroxicam, meloxicam, tanoxicam, droxicam, lomoxicam, and isoxicam), fenamic acid derivatives (e.g., mefamic acid, meclofenamic acid, flufenamic acid, and tolfenamic acid), sulphonanilides (e.g., nimesulide), licofelone, and lysine clonixinate. In some embodiments, an NSAID is a COX-I inhibitor or a COX-II inhibitor. Non-limiting examples of COX-I inhibitors include aspirin, ibuprofen, and naproxen. Non-limiting examples of COX-II inhibitors include celecoxib, valdecoxib, and rofecoxib.

Non-limiting examples of ImSAIDs include FEG (Phe-Glu-Gly), its D-isomer feG, and SGP-T peptide. Non-limiting examples of corticosteroids include hydrocortisone, cortisone acetate, tixocortol pivalate, prednisolone, methylprednisolone, prednisone, triamcinolone acetonide, triamcinolone alcohol, mometasone, amcinonide, budesonide, desonide, fluocinolone, halcinonide, betamethasone, dexamethasone, and fluocortolone. Non-limiting examples of biologics include tocilizumab, certolizumab, etanercept, adalimumab, anakinra, abatacept, efalizumab, infliximab, rituximab, and golimumab.

Immunosuppressive Agents

The compositions described herein can also contain one or more immunosuppressive agents. Non-limiting examples of immunosuppressive agents include mycophenolate, ciclosporin, cyclosporine, tacrolimus, sirolimus, and pimecrolimus. Additional immunosuppressive agents are known in the art.

Chemotherapeutic Agents In some embodiments, the compositions further contain one or more chemotherapeutic agents. Non-limiting examples of chemotherapeutic agents include alkylating agents (e.g., cyclophosphamide, mechlorethamine, chlorambucil, and melphalan), anthracyclines (e.g., daunorubicin, doxorubicin, epirubicin, idarubicin, mitoxantrone, and valrubicin), taxanes (e.g., paxlitaxel and docetaxel), epothilones, histone deacetylase inhibitors (e.g., vorinostat and romidepsin), topoisomerase II inhibitors (e.g., etoposide, teniposide, and tafluposide), kinase inhibitors (e.g., bortezomib, erlotinib, gefitinib, imatinib, and vismodegib), bevacizumab, cetuximab, ipilimumab, ipilimumab, ofatumumab, ocrelizumab, panitumab, rituximab, vemurafenib, herceptin, nucleotide analogs (e.g., azacitidine, azathioprine, capecitabine, cytarabine, doxifluridine, fluorouracil, gemcitabine, hydroxyurea, mercaptopurine, methotrexate, and thioguanine), peptide antibiotics (e.g., bleomycin and actinomycin), platinum-based agents (e.g., carboplatin, cisplatin, and oxaliplatin), retinoids (e.g., tretinoin, alitretinoin, and bexarotene), and vinca alkaloids (e.g., vinblastine, vincristine, vindesine, and vinorelbine).

Analgesics

In some embodiments, the composition can further contain one or more analgesics. Any of the exemplary analgesics described herein or known in the art can be included in the compositions described herein. Non-limiting examples of analgesics include opioid drugs (e.g., morphine, opium, codeine, oxycodone, hydrocodone, diamorphine, dihydromorphine, pethidine, buprenorphine, fentanyl, methadone, meperidine, pentazocine, dipipanone, and tramadol), acetaminophen, venlafaxine, flupirtine, nefopam, gabapentin, pregabalin, orphenadrine, cyclobenzaprine, trazodone, clonidine, duloxetine and amitriptyline.

Methods of Producing Anti-LILRB3 Antibodies

The anti-LILRB3 antibodies (or antigen binding domain of an antibody or functional fragment thereof) of this disclosure may be produced in bacterial or eukaryotic cells. To produce the polypeptide of interest, a polynucleotide encoding the polypeptide is constructed, introduced into an expression vector, and then expressed in suitable host cells. Standard molecular biology techniques are used to prepare the recombinant expression vector, transfect the host cells, select for transformants, culture the host cells and recover the antibody.

If the antibody is to be expressed in bacterial cells (e.g., E. coli), the expression vector should have characteristics that permit amplification of the vector in the bacterial cells. Additionally, when E. coli such as JM109, DH5α, HB101, or XL1-Blue is used as a host, the vector must have a promoter, for example, a lacZ promoter (Ward et al., 341: 544-546 (1989), araB promoter (Better et al., Science, 240:1041-1043 (1988)), or T7 promoter that can allow efficient expression in E. coli. Examples of such vectors include, for example, M13-series vectors, pUC-series vectors, pBR322, pBluescript, pCR-Script, pGEX-5X-1 (Pharmacia), "QIAexpress system" (QIAGEN), pEGFP, and pET (when this expression vector is used, the host is preferably BL21 expressing T7 RNA polymerase). The expression vector may contain a signal sequence for antibody secretion. For production into the periplasm of E. coli, the pelB signal sequence (Lei et al., J. Bacteriol., 169:4379 (1987)) may be used as the signal sequence for antibody secretion. For bacterial expression, calcium chloride methods or electroporation methods may be used to introduce the expression vector into the bacterial cell.

If the antibody is to be expressed in animal cells such as CHO, COS, 293, 293T, and NIH3T3 cells, the expression vector includes a promoter necessary for expression in these cells, for example, an SV40 promoter (Mulligan et al., Nature, 277:108 (1979)), MMLV-LTR promoter, EF1α promoter (Mizushima et al., Nucleic Acids Res., 18:5322 (1990)), or CMV promoter. In addition to the nucleic acid sequence encoding the immunoglobulin or domain thereof, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin, or methotrexate, on a host cell into which the vector has been introduced. Examples of vectors with selectable markers include pMAM, pDR2, pBK-RSV, pBK-CMV, pOPRSV, and pOP13.

In one embodiment, the antibodies are produced in mammalian cells. Exemplary mammalian host cells for expressing a polypeptide include Chinese Hamster Ovary (CHO cells) (including dhfr-CHO cells, described in Urlaub and Chasin (1980) Proc. Natl. Acad. Sci. USA 77:4216-4220, used with a DHFR selectable marker, e.g., as described in Kaufman and Sharp (1982) Mol. Biol. 159:601 621), human embryonic kidney 293 cells (e.g., 293, 293E, 293T), COS cells, NIH3T3 cells, lymphocytic cell lines, e.g., NS0 myeloma cells and SP2 cells, and a cell from a transgenic animal, e.g., a transgenic mammal. For example, the cell is a mammary epithelial cell.

The antibodies of the present disclosure can be isolated from inside or outside (such as medium) of the host cell and purified as substantially pure and homogenous antibodies. Methods for isolation and purification commonly used for polypeptides may be used for the isolation and purification of antibodies described herein, and are not limited to any particular method. Antibodies may be isolated and purified by appropriately selecting and combining, for example, column chromatography, filtration, ultrafiltration, salting out, solvent precipitation, solvent extraction, distillation, immunoprecipitation, SDS-polyacrylamide gel electrophoresis, isoelectric focusing, dialysis, and recrystallization. Chromatography includes, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., Cold Spring Harbor Laboratory Press, 1996). Chromatography can be carried out using liquid phase chromatography such as HPLC and FPLC. Columns used for affinity chromatography include protein A column and protein G column. Examples of columns using protein A column include Hyper D, POROS, and Sepharose FF (GE Healthcare Biosciences). The present disclosure also includes antibodies that are highly purified using these purification methods.

The present disclosure also provides a nucleic acid molecule or a set of nucleic acid molecules encoding an anti-LILRB3 antibody or antigen binding molecule thereof disclosed herein. In one embodiment, the invention includes a nucleic acid molecule encoding a polypeptide chain, which comprises a light chain of an anti-LILR3 antibody or antigen-binding molecule thereof as described herein. In one embodiment, the invention includes a nucleic acid molecule encoding a polypeptide chain, which comprises a heavy chain of an anti-LILR3 antibody or antigen-binding molecule thereof as described herein.

Also provided are a vector or a set of vectors comprising such nucleic acid molecule or the set of the nucleic acid molecules or a complement thereof, as well as a host cell comprising the vector.

The instant disclosure also provides a method for producing a LILRB3 or antigen-binding molecule thereof or chimeric molecule disclosed herein, such method comprising culturing the host cell disclosed herein and recovering the antibody, antigen-binding molecule thereof, or the chimeric molecule from the culture medium.

A variety of methods are available for recombinantly producing a LILRB3 antibody or antigen-binding molecule thereof disclosed herein, or a chimeric molecule disclosed herein. It will be understood that because of the degeneracy of the code, a variety of nucleic acid sequences will encode the amino acid sequence of the polypeptide. The desired polynucleotide can be produced by de novo solid-phase DNA synthesis or by PCR mutagenesis of an earlier prepared polynucleotide.

For recombinant production, a polynucleotide sequence encoding a polypeptide (e.g., a LILRB3 antibody or antigen-binding molecule thereof disclosed herein, or any of the chimeric molecules disclosed herein) is inserted into an appropriate expression vehicle, i.e., a vector which contains the necessary elements for the transcription and translation of the inserted coding sequence, or in the case of an RNA viral vector, the necessary elements for replication and translation.

The nucleic acid encoding the polypeptide (e.g., a LILRB3 antibody or antigen-binding molecule thereof disclosed herein, or any of the chimeric molecules disclosed herein) is inserted into the vector in proper reading frame. The expression vector is then transfected into a suitable target cell which will express the polypeptide. Transfection techniques known in the art include, but are not limited to, calcium phosphate precipitation (Wigler et al. 1978, Cell 14:725) and electroporation (Neumann et al. 1982, EMBO J. 1:841). A variety of host-expression vector systems can be utilized to express the polypeptides described herein (e.g., a LILRB3 antibody or antigen-binding molecule thereof disclosed herein, or any of the chimeric molecules disclosed herein) in eukaryotic cells. In one embodiment, the eukaryotic cell is an animal cell, including mammalian cells (e.g., 293 cells, PerC6, CHO, BHK, Cos, HeLa cells). When the polypeptide is expressed in a eukaryotic cell, the DNA encoding the polypeptide (e.g., a LILRB3 antibody or antigen-binding molecule thereof disclosed herein, or any of the chimeric molecules disclosed herein) can also code for a signal sequence that will permit the polypeptide to be secreted. One skilled in the art will understand that while the polypeptide is translated, the signal sequence is cleaved by the cell to form the mature chimeric molecule. Various signal sequences are known in the art and familiar to the skilled practitioner. Alternatively, where a signal sequence is not included, the polypeptide (e.g., a LILRB3 antibody or antigen-binding molecule thereof disclosed herein, or any of the chimeric molecules disclosed herein) can be recovered by lysing the cells.

Pharmaceutical Compositions

The present disclosure also provides pharmaceutical compositions comprising one or more of: (i) a LILRB3 antibody or antigen-binding molecule thereof disclosed herein; (ii) a nucleic acid molecule or the set of nucleic acid molecules encoding a LILRB3 antibody or antigen-binding molecule as disclosed herein; or (iii) a vector or set of vectors disclosed herein, and a pharmaceutically acceptable carrier.

An anti-LILRB3 antibodies or fragments thereof described herein can be formulated as a pharmaceutical composition for administration to a subject, e.g., to treat a disorder described herein. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge, S. M., et al. (1977) J. Pharm. Sci. 66:1-19).

Pharmaceutical formulation is a well-established art, and is further described, e.g., in Gennaro (ed.), Remington: The Science and Practice of Pharmacy, 20th ed., Lippincott, Williams & Wilkins (2000) (ISBN: 0683306472); Ansel et al., Pharmaceutical Dosage Forms and Drug Delivery Systems, 7th Ed., Lippincott Williams & Wilkins Publishers (1999) (ISBN: 0683305727); and Kibbe (ed.), Handbook of Pharmaceutical Excipients American Pharmaceutical Association, 3rd ed. (2000) (ISBN: 091733096X).

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form can depend on the intended mode of administration and therapeutic application. Typically compositions for the agents described herein are in the form of injectable or infusible solutions.

In one embodiment, an antibody described herein is formulated with excipient materials, such as sodium citrate, sodium dibasic phosphate heptahydrate, sodium monobasic phosphate, Tween®-80, and a stabilizer. It can be provided, for example, in a buffered solution at a suitable concentration and can be stored at 2-8° C. In some other embodiments, the pH of the composition is between about 5.5 and 7.5 (e.g., 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5).

The pharmaceutical compositions can also include agents that reduce aggregation of the antibody when formulated. Examples of aggregation reducing agents include one or more amino acids selected from the group consisting of methionine, arginine, lysine, aspartic acid, glycine, and glutamic acid. These amino acids may be added to the formulation to a concentration of about 0.5 mM to about 145 mM (e.g., 0.5 mM, 1 mM, 2 mM, 5 mM, 10 mM, 25 mM, 50 mM, 100 mM). The pharmaceutical compositions can also include a sugar (e.g., sucrose, trehalose, mannitol, sorbitol, or xylitol) and/or a tonicity modifier (e.g., sodium chloride, mannitol, or sorbitol) and/or a surfactant (e.g., polysorbate-20 or polysorbate-80).

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the antibodies may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., Marcel Dekker, Inc., New York (1978).

In one embodiment, the pharmaceutical formulation comprises an antibody at a concentration of about 0.005 mg/mL to 500 mg/mL (e.g., 0.005 mg/ml, 0.01 mg/ml, 0.05 mg/ml, 0.1 mg/ml, 0.5 mg/mL, 1 mg/mL, 5 mg/mL, 10 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 125 mg/mL, 150 mg/mL, 175 mg/mL, 200 mg/mL, 250 mg/mL, 300 mg/mL, 350 mg/mL, 400 mg/mL, 450 mg/mL, 500 mg/mL), formulated with a pharmaceutically acceptable carrier. In some embodiments, the antibody is formulated in sterile distilled water or phosphate buffered saline. The pH of the pharmaceutical formulation may be between 5.5 and 7.5 (e.g., 5.5, 5.6, 5.7, 5.8, 5.9, 6.0, 6.1, 6.2 6.3, 6.4 6.5, 6.6 6.7, 6.8, 6.9 7.0, 7.1, 7.3, 7.4, 7.5).

A pharmaceutical composition may include a "therapeutically effective amount" of an agent described herein. Such effective amounts can be determined based on the effect of the administered agent, or the combinatorial effect of agents if more than one agent is used. A therapeutically effective amount of an agent may also vary according to factors such as the disease state, age, sex, and weight of the individual, and the ability of the compound to elicit a desired response in the individual, e.g., amelioration of at least one disorder parameter or amelioration of at least one symptom of the disorder. A therapeutically effective amount is also one in which any toxic or detrimental effects of the composition are outweighed by the therapeutically beneficial effects.

Administration

The antibodies or antigen-binding fragment thereof, or nucleic acids encoding same of the disclosure can be administered to a subject, e.g., a subject in need thereof, for example, a human or animal subject, by a variety of methods. For many applications, the route of administration is one of: intravenous injection or parenteral, infusion (IV), subcutaneous injection (SC), intraperitoneally (IP), or intramuscular injection, intratumor (IT). Other modes of parenteral administration can also be used. Examples of such modes include: intraarterial, intrathecal, intracapsular, intraorbital, intracardiac, intradermal, transtracheal, subcuticular, intraarticular, subcapsular, subarachnoid, intraspinal, and epidural and intrasternal injection.

In one embodiment, the route of administration of the antibodies of the invention is parenteral. The term parenteral as used herein includes intravenous, intraarterial, intraperitoneal, intramuscular, subcutaneous, rectal or vaginal administration. The intravenous form of parenteral administration is preferred. While all these forms of administration are clearly contemplated as being within the scope of the invention, a form for administration would be a solution for injection, in particular for intravenous or intraarterial injection or drip. Usually, a suitable pharmaceutical composition for injection can comprise a buffer (e.g., acetate, phosphate or citrate buffer), a surfactant (e.g. polysorbate), optionally a stabilizer agent (e.g., human albumin), etc. However, in other methods compatible with the teachings herein, the polypeptides can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as for example, antimicrobials, anti-oxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations can be packaged and sold in the form of a kit. Such articles of manufacture will preferably have labels or package inserts indicating that the associated compositions are useful for treating a subject suffering from, or predisposed to clotting disorders.

Effective doses of the compositions of the present disclosure, for the treatment of conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages can be titrated using routine methods known to those of skill in the art to optimize safety and efficacy.

The route and/or mode of administration of the anti-LILRB3 antibody or fragment thereof can also be tailored for the individual case, e.g., by monitoring the subject.

The antibody or fragment thereof can be administered as a fixed dose, or in a mg/kg dose. The dose can also be chosen to reduce or avoid production of antibodies against the anti-LILRB3 antibody or fragment thereof. Dosage regimens are adjusted to provide the desired response, e.g., a therapeutic response or a combinatorial therapeutic effect. Generally, doses of the antibody or fragment thereof (and optionally a second agent) can be used in order to provide a subject with the agent in bioavailable quantities. For example, doses in the range of 0.1-100 mg/kg, 0.5-100 mg/kg, 1 mg/kg-100 mg/kg, 0.5-20 mg/kg, 0.1-10 mg/kg, or 1-10 mg/kg can be administered. Other doses can also be used. In certain embodiments, a subject in need of treatment with an antibody or fragment thereof is administered the antibody or fragment thereof at a dose of between about 1 mg/kg to about 30 mg/kg. In some embodiments, a subject in need of treatment with anti-LILRB3 antibody or fragment thereof is administered the antibody or fragment thereof at a dose of 1 mg/kg, 2 mg/kg, 4 mg/kg, 5 mg/kg, 7 mg/kg 10 mg/kg, 12 mg/kg, 15 mg/kg, 20 mg/kg, 25 mg/kg, 28 mg/kg, 30 mg/kg, 35 mg/kg, 40 mg/kg, or 50 mg/kg. In a specific embodiment, the antibody or fragment thereof is administered subcutaneously at a dose of 1 mg/kg to 3 mg/kg. In another embodiment, the antibody or fragment thereof is administered intravenously at a dose of between 4 mg/kg and 30 mg/kg.

A composition may comprise about 1 mg/mL to 100 mg/ml or about 10 mg/mL to 100 mg/ml or about 50 to 250 mg/mL or about 100 to 150 mg/ml or about 100 to 250 mg/ml of the antibody or fragment thereof.

Dosage unit form or "fixed dose" as used herein refers to physically discrete units suited as unitary dosages for the subjects to be treated; each unit contains a predetermined quantity of antibody or fragment thereof calculated to produce the desired therapeutic effect in association with the required pharmaceutical carrier and optionally in association with the other agent. Single or multiple dosages may be given. Alternatively, or in addition, the antibody or fragment thereof may be administered via continuous infusion.

An antibody or fragment thereof dose can be administered, e.g., at a periodic interval over a period of time (a course of treatment) sufficient to encompass at least 2 doses, 3 doses, 5 doses, 10 doses, or more, e.g., once or twice daily, or about one to four times per week, or preferably weekly, biweekly (every two weeks), every three weeks, monthly, e.g., for between about 1 to 12 weeks, preferably between 2 to 8 weeks, more preferably between about 3 to 7 weeks, and even more preferably for about 4, 5, or 6 weeks. Factors that may influence the dosage and timing required to effectively treat a subject, include, e.g., the stage or severity of the disease or disorder, formulation, route of delivery, previous treatments, the general health and/or age of the subject, and other diseases present. Moreover, treatment of a subject with a therapeutically effective amount of a compound can include a single treatment or, preferably, can include a series of treatments.

If a subject is at risk for developing a disorder described herein, the antibody or fragment thereof can be administered before the full onset of the disorder, e.g., as a preventative measure. The duration of such preventative treatment can be a single dosage of the antibody or fragment thereof or the treatment may continue (e.g., multiple dosages). For example, a subject at risk for the disorder or who has a predisposition for the disorder may be treated with the antibody or fragment thereof for days, weeks, months, or even years so as to prevent the disorder from occurring or fulminating.

In certain embodiments, the antibody or fragment thereof is administered subcutaneously at a concentration of about 1 mg/mL to about 500 mg/mL (e.g., 1 mg/mL, 2 mg/mL, 3 mg/mL, 4 mg/mL, 5 mg/mL, 10 mg/mL, 15 mg/mL, 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 125 mg/mL, 150 mg/mL, 175 mg/mL, 200 mg/mL, 225 mg/mL, 250 mg/mL, 275 mg/mL, 300 mg/mL, 325 mg/mL, 350 mg/mL, 400 mg/mL, 450 mg/mL). In one embodiment, the anti-LILRB3 antibody or fragment thereof is administered subcutaneously at a concentration of 50 mg/mL. In another embodiment, the antibody or fragment thereof is administered intravenously at a concentration of about 1 mg/mL to about 500 mg/mL. In one embodiment, the antibody or fragment thereof is administered intravenously at a concentration of 50 mg/mL.

The anti-LILRB3 antibody or fragment thereof can be administered to a patient in need thereof alone or in combination with (i.e., by co-administration or sequential administration) other therapeutic agents useful for treating a cancer or immunological disorder as described herein may be desirable. Such therapeutic agents can be chemical or biologic in nature. The term "biologic" or "biologic agent" refers to any pharmaceutically active agent made from living organisms and/or their products which is intended for use as a therapeutic. In one embodiment, the additional therapeutic proteins are included in the pharmaceutical composition of the present invention.

Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. In some methods, two or more polypeptides can be administered simultaneously, in which case the dosage of each polypeptide administered falls within the ranges indicated.

Polypeptides of the invention can be administered on multiple occasions. Intervals between single dosages can be daily, weekly, monthly or yearly. Intervals can also be irregular as indicated by measuring blood levels of modified polypeptide or antigen in the patient. Alternatively, polypeptides can be administered as a sustained release formulation, in which case less frequent administration is required. Dosage and frequency vary depending on the half-life of the polypeptide in the patient.

The dosage and frequency of administration can vary depending on whether the treatment is prophylactic or therapeutic. In prophylactic applications, compositions containing the polypeptides of the invention or a cocktail thereof are administered to a patient not already in the disease state to enhance the patient's resistance or minimize effects of disease. Such an amount is defined to be a "prophylactic effective dose." A relatively low dosage is administered at relatively infrequent intervals over a long period of time. Some patients continue to receive treatment for the rest of their lives.

Methods of Use

The antibodies, or antigen-binding fragments thereof of the disclosure can be useful in methods of treating a subject with a disease or condition. The disease or condition can include, but is not limited to, cancer.

For example, the present invention includes the use of anti-LILRB3, including antagonists or agonists having anti-LILRB3 activity. The invention includes administering to a subject the anti-LILRB3 antibodies or a fragment thereof and contemplates both human and veterinary therapeutic uses. Illustrative veterinary subjects include mammalian subjects, such as farm animals and domestic animals.

Provided herein are methods of stimulating a pro-inflammatory immune response in a mammal that include administering to a mammal a therapeutically effective amount of an anti-LILRB3 antibody or fragment thereof as described herein.

In some embodiments, an increase in pro-inflammatory immune response in a mammal can be detected as an increase in the levels of one or more pro-inflammatory proteins in the mammal (e.g., an increase in one or more of C-reactive protein, IL-1α, IL-1β, TNF-α, IL-6, IL-8, IL-23, IL-17, and matrix metalloproteases) or an increase in the number of effector T-cells (Teff) in the mammal (e.g., as compared to the levels of the one or more pro-inflammatory proteins in the mammal and/or the levels of effector T-cells in the mammal prior to treatment or compared to the levels of the one or more pro-inflammatory proteins and/or the levels of effector T-cells present in a control, healthy mammal).

Provided herein are methods of treating in a mammal that include administering to a mammal a therapeutically effective amount of an anti-LILRB3 antibody or fragment thereof as described herein.

In some embodiments, the mammal (e.g., human) has been previously diagnosed as having a cancer (e.g., any of the different types of cancer described herein). Non-limiting examples of cancer include: bladder cancer, breast cancer, colon cancer, colorectal cancer, endometrial cancer, kidney cancer, lung cancer, melanoma, pancreatic cancer, prostate cancer, thyroid cancer, bile duct cancer, bone cancer, brain cancer, cervical cancer, cardiac tumors, esophageal cancer, eye cancer, gallbladder cancer, gastric cancer, head and neck cancer, heart cancer, liver cancer, laryngeal cancer, leukemia, lip and oral cavity cancer, lymphoma, melanoma, mesothelioma, mouth cancer, nasal cavity and paranasal sinus cancer, nasopharyngeal cancer, non-Hodgkin lymphoma, ovarian cancer, penile cancer, pituitary tumor, retinoblastoma, sarcoma, skin cancer, testicular cancer, throat cancer, thyroid cancer, urethral cancer, uterine cancer, vaginal cancer, and vulvar cancer. A mammal having cancer can present with one or more of the following symptoms: fatigue, lump or thickening that can be felt under the skin, weight changes, skin changes (e.g., yellowing, darkening or redness of the skin, sores that won't heal, or changes in existing moles), changes in bowel or bladder habits, persistent cough, difficulty swallowing, hoarseness, persistent indigestion or discomfort after eating, persistent, unexplained muscle or joint pain, and unexplained and persistent fevers or night sweats. The particular symptoms experienced by a mammal will depend on the particular type of cancer. A mammal can be diagnosed as having a cancer based on the observation of one or more symptoms of cancer in the mammal (e.g., any of the symptoms of cancer described herein or known in the art). A mammal can also be diagnosed as having a cancer based on imaging (e.g., magnetic resonance imaging, computed tomography, and/or X-ray) and/or tissue biopsy results. A mammal can also be diagnosed as having a cancer based using molecular diagnostic tests (e.g., based on the detection of prostate specific antigen, or mutations in breast cancer susceptibility 2 protein, breast cancer susceptibility 1 protein, or a tumor suppressor protein (e.g., p53)). Additional methods for diagnosing a mammal as having cancer are known in the art. Efficacy of treatment of a cancer can be detected by a decrease the number of symptoms of a cancer in a mammal (e.g., any of the symptoms of cancer described herein or known in the art) and/or a decrease in the frequency and/or severity of one or more symptoms of cancer in a mammal (e.g., any of the symptoms described herein or known in the art). An effective treatment of cancer in a mammal can also be assessed by a decrease in the rate of growth of a tumor in a mammal (e.g., compared to the rate of tumor growth in the mammal prior to administration of treatment or compared to a control mammal having the same type of cancer not administered a treatment or administered a different treatment). An effective treatment of cancer in a mammal can also be observed by an increase in the length of remission of cancer in the mammal (e.g., compared to a control mammal having the same type of cancer not administered a treatment or administered a different treatment).

The mammal may be female or male, and may be an adult or juvenile (e.g., an infant). The mammal may have been previously treated with a chemotherapeutic agent and/or analgesic and/or responded poorly to the chemotherapeutic agent and/or analgesic. The mammal may have non-metastatic cancer. In some embodiments, the mammal can have metastatic cancer. Where the mammal is an adult, the mammal may be, e.g., between 18 to 20 years old or at least or about 20, 25, 30, 35, 40, 45, 50, 55, 60, 65, 70, 75, 80, 85, 90, 95, or at least or about 100 years old.

Also provided are methods of treating cancer in a mammal that include administering to the mammal a therapeutically effective amount of an anti-LILRB3 antibody or fragment thereof as described herein.

Devices and Kits for Therapy

Pharmaceutical compositions that include the anti-LILRB3 antibody or fragment thereof described herein can be administered with a medical device. The device can be designed with features such as portability, room temperature storage, and ease of use so that it can be used in emergency situations, e.g., by an untrained subject or by emergency personnel in the field, removed from medical facilities and other medical equipment. The device can include, e.g., one or more housings for storing pharmaceutical preparations that include an anti-LILRB3 antibody or fragment thereof, and can be configured to deliver one or more unit doses of the antibody or fragment thereof. The device can be further configured to administer a second agent, e.g., a chemotherapeutic agent, either as a single pharmaceutical composition that also includes the anti-LILRB3 antibody or fragment thereof or as two separate pharmaceutical compositions.

An anti-LILRB3 antibody or fragment thereof can be provided in a kit. In one embodiment, the kit includes (a) a container that contains a composition that includes an anti-LILRB3 antibody or fragment thereof as described herein, and optionally (b) informational material. The informational material can be descriptive, instructional, marketing or other material that relates to the methods described herein and/or the use of the agents for therapeutic benefit.

In an embodiment, the kit also includes a second agent for treating a disorder described herein. For example, the kit includes a first container that contains a composition that includes the anti-LILRB3 antibody or fragment thereof, and a second container that includes the second agent.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the anti-LILRB3 antibody or fragment thereof, e.g., in a suitable dose, dosage form, or mode of administration (e.g., a dose, dosage form, or mode of administration described herein), to treat a subject who has had or who is at risk for a disease as described herein. The information can be provided in a variety of formats, include printed text, computer readable material, video recording, or audio recording, or information that provides a link or address to substantive material, e.g., on the internet.

In addition to the anti-LILRB3 antibody or fragment thereof, the composition in the kit can include other ingredients, such as a solvent or buffer, a stabilizer, or a preservative. The anti-LILRB3 antibody or fragment thereof can be provided in any form, e.g., liquid, dried or lyophilized form, preferably substantially pure and/or sterile. When the agents are provided in a liquid solution, the liquid solution preferably is an aqueous solution. In certain embodiments, the anti-LILRB3 antibody or fragment thereof in the liquid solution is at a concentration of about 25 mg/mL to about 250 mg/mL (e.g., 40 mg/mL, 50 mg/mL, 60 mg/mL, 75 mg/mL, 85 mg/mL, 100 mg/mL, 125 mg/mL, 150 mg/mL, and 200 mg/mL). When the anti-LILRB3 antibody or fragment thereof is provided as a lyophilized product, the anti-LILRB3 antibody or fragment thereof is at about 75 mg/vial to about 200 mg/vial (e.g., 100 mg/vial, 108.5 mg/vial, 125 mg/vial, 150 mg/vial). The lyophilized powder is generally reconstituted by the addition of a suitable solvent. The solvent, e.g., sterile water or buffer (e.g., PBS), can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the anti-LILRB3 antibody or fragment thereof and the second agent, e.g., in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

EXAMPLES

The invention is further described in the following examples, which do not limit the scope of the invention described in the claims.
Antibody Purification Clonal hybridoma cells were cultured in ClonaCell-HY Medium A (StemCell Technologies) followed by adaptation to serum-free conditions using Hybridoma-SFM (ThermoFisher Scientific). Hybridoma cells were expanded in 50 mL of Hybridoma SFM for 2 weeks or until medium was exhausted. Antibody-containing supernatant was harvested by centrifugation followed by sterile 0.22 micron filtration. Antibodies were concentrated using Amicon Ultra-15 centrifugal filter concentrator with nominal molecular weight limit of 100 kDa (Millipore). Concentrated antibodies were then purified using Nab Protein A/G Spin Kit (Thermo Fisher Scientific) according to manufacturer's instructions. Purified antibodies were desalted using Zeba Spin Columns (Thermo Fisher Scientific).
Hybridoma IgL and IgH Chain Sequencing RNA from hybridoma clones was extracted using Trizol extraction. cDNA was synthesized from purified RNA using OneStep RT-PCR Kit (Qiagen) according to manufacturer's instructions. PCR of Ig heavy and light chains was performed using degenerate primers. Amplified PCR products were subsequently sequenced (GeneWiz) and validated using IMGT/V-QUEST from The International Immunogenetics Information System.
Sequence of Hybridoma Using degenerate primers flanking the mouse kappa and heavy chain Ig genes, the heavy and light chain genes and complementarity determining regions (CDRs) sequences were determined for the indicated clones. Total RNA isolated from early passage hybridomas was converted to cDNA using RT-PCR followed by PCR amplification of the heavy and light chain genes. PCR products were sequenced by Sanger sequencing followed by Ig-BLAST comparison to known allele framework from databases. Productive antibody sequences are listed Table 3 showing the closest aligning mouse alleles and CDRs1-3.

Anti-LILRB3 antagonists promote TNF alpha secretion whereas anti-LILRB3 agonist promotes IL-10 secretion from total peripheral blood mononuclear cells (PBMC) in the presence of low-dose LPS stimulation. The inventors screened several monoclonal antibodies (mAbs) for biological function with total PBMC under the inflammatory condition. The mAbs with antagonistic functional characteristics can further promote the TNF alpha production from total PBMC under the low dose of LPS stimulation, but do not affect the IL-10 secretion. On the other hand, the agonistic clones can increase the IL-10 production (FIG. 1). Those clones that can induce TNF alpha secretion were considered as antagonists whereas those induce IL-10 are considered as agonists.

Example 1: Anti-LILRB3 Antibodies Modulate TNF Alpha Secretion In Vitro

Figure 1B:
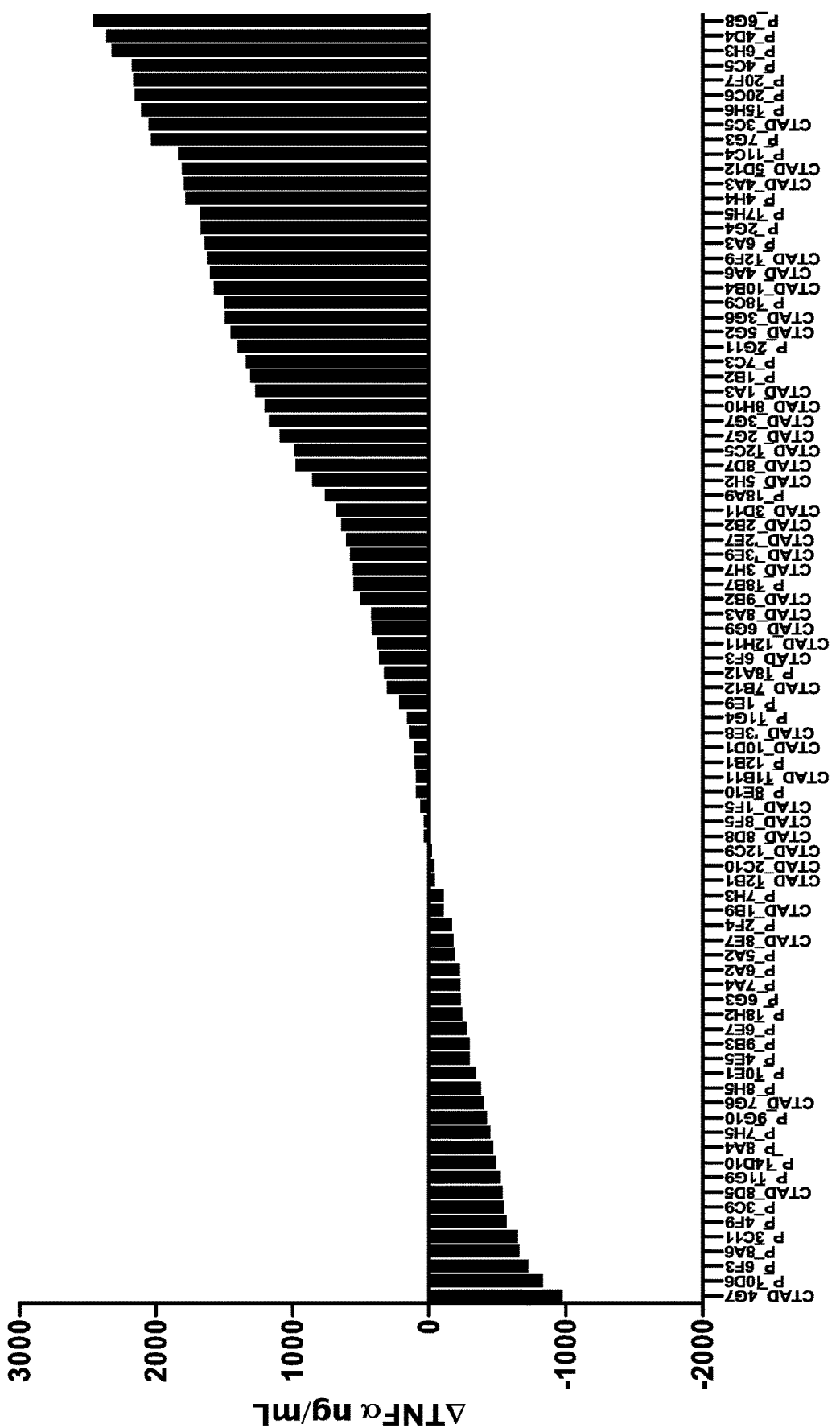
Figure 1C:
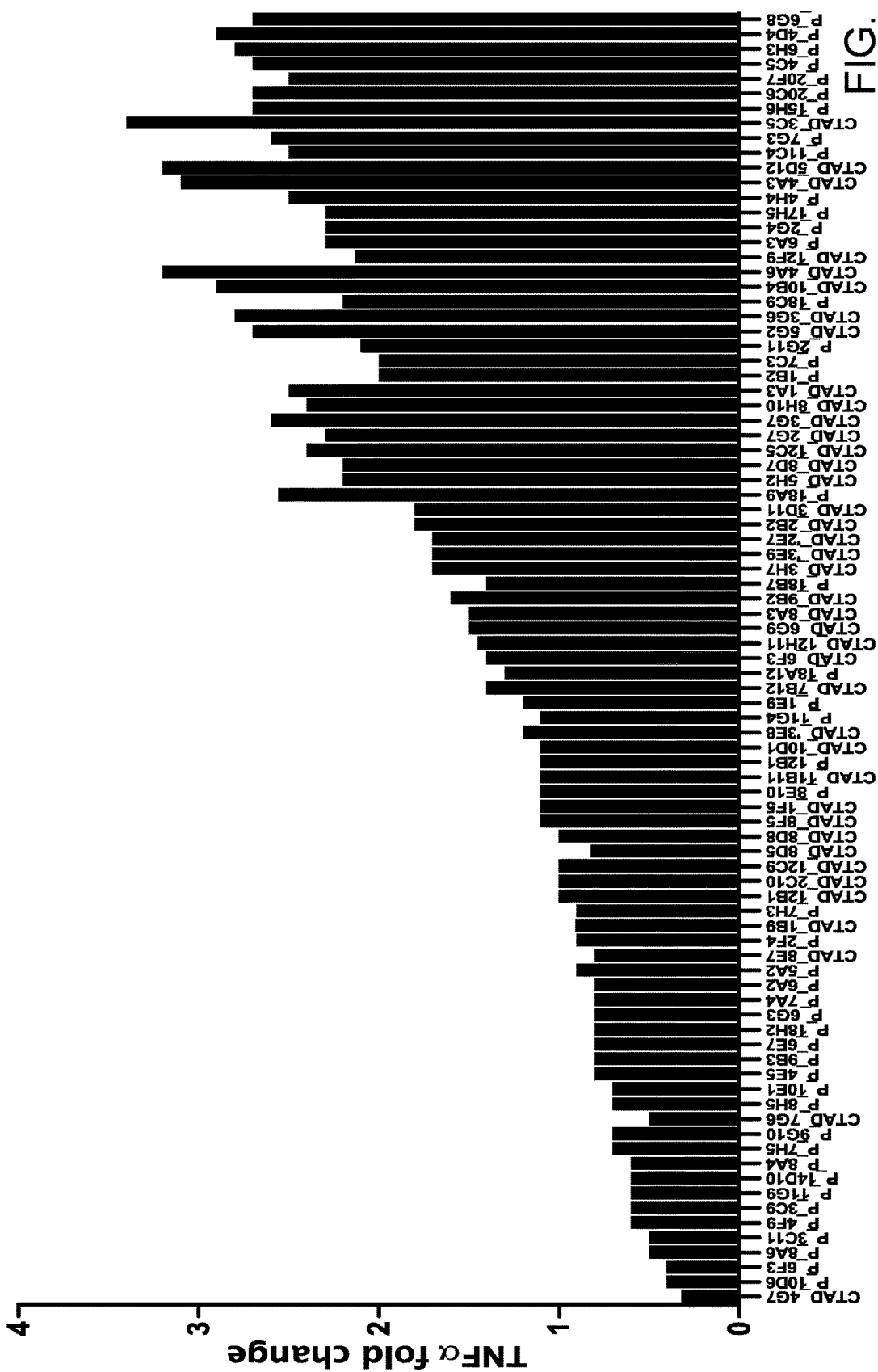

Total PBMC from healthy donors were treated with anti-LILRB3 hybridoma supernatants or purified antibodies (5 microgram/ml) for 24 hours followed by stimulation with LPS (100 ng/ml) for 6 hours. Supernatants were collected and TNF alpha concentrations were measured by ELISA. Isotype treatment was used as a control. Anti-LILRB mAbs were ranked in order of clones that suppress TNF alpha release to those that enhance TNF alpha secretion. Clone ranking based on production of TNF-α from FIG. 1A. The overall difference in TNF alpha levels from FIG. 1A is presented in FIG. 1B (i.e., with background TNF-α subtracted), while the relative fold change in TNF alpha release is shown in FIG. 1C.

Example 2

Anti-LILRB3 Antibodies Modulate IL-10 Production In Vitro.

Figure 2A:
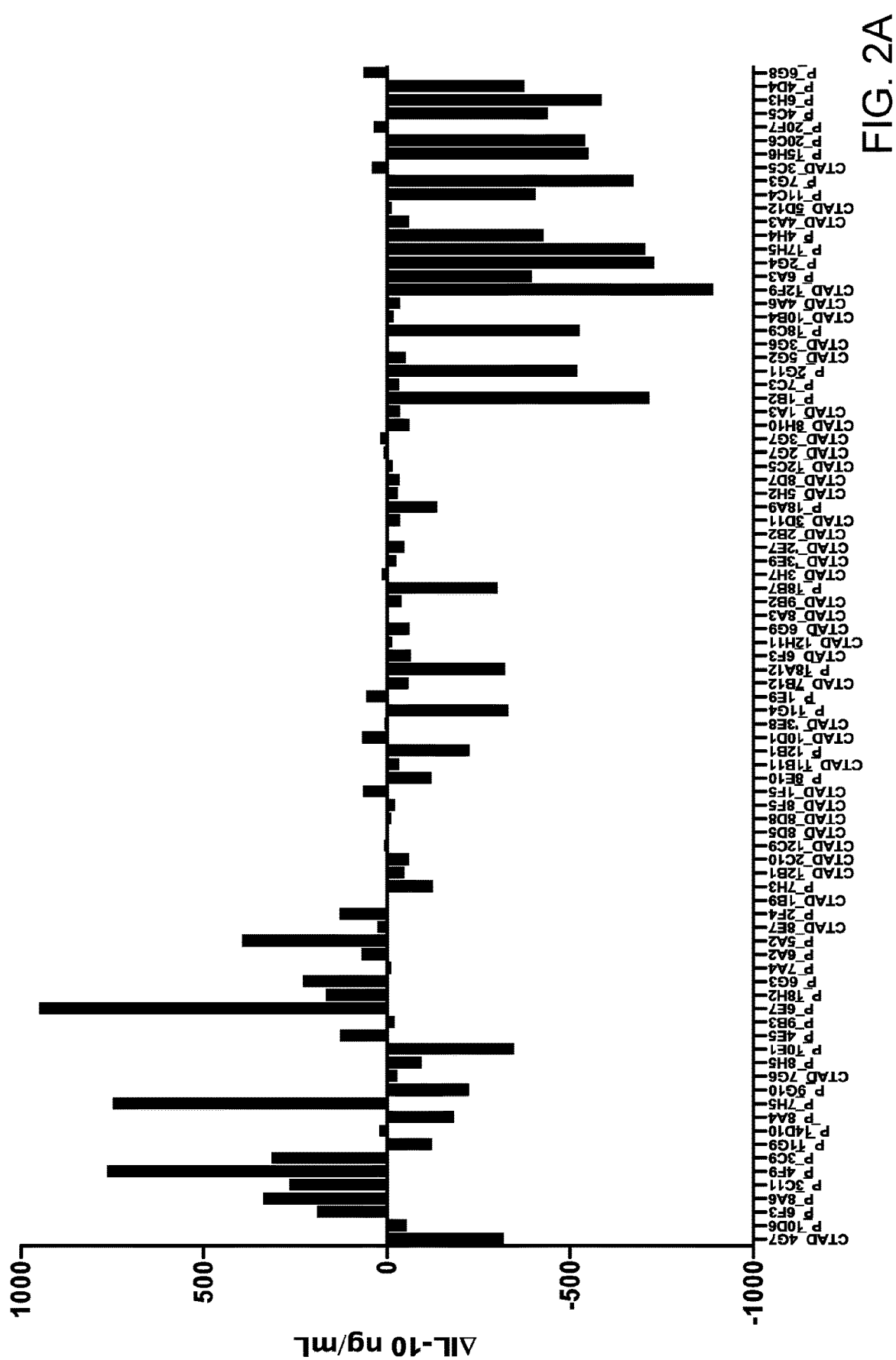

Total PBMC from healthy donors were treated with anti-LILRB3 hybridoma supernatants or purified antibodies (5 microgram/ml) for 24 hours followed by stimulation with LPS (100 ng/ml) for 6 hours. Supernatants were collected and IL-10 concentrations were measured by ELISA. Isotype treatment was used as a control. The overall difference in IL-10 concentrations is presented in FIG. 2A, subtracting background IL-10 production as determined by control samples, while the relative fold change is shown in FIG. 2B. For each of FIG. 2A and FIG. 2B, the clones are ordered according to the clonal ranking presented in FIG. 1A.
The Effect on the Anti-LILRB3 on M1/M2 Differentiation.

CD33+ myeloid cells were sorted from healthy PBMC and differentiated as monocyte-derived macrophages (MDM) by M-CSF 50 ng/ml for 5 days. MDM were then treated with anti-LILRB3 Ab with antagonistic and agonistic activity (5 ug/ml) under M1-polarization condition in the presence of interferon gamma (50 ng/ml) for 2 days. Several surface markers involved M1/M2 differentiation (CD163, CD206, PD-L1, HLA-DR) and human CD33+CD14+CD16+ MDSC population were shown in (FIG. 2C).

Example 3

Anti-LILRB3 Antibodies Modulate T Cell Proliferation and IFN Gamma Secretion In Vitro.

PBMC from healthy donors were stimulated with a low dose (0.3 microgram/ml) anti-CD3 (OKT3) in the presence of anti-LILRB3 mAb supernatants or purified mAbs (5 microgram/ml). After 3 days of treatment, T cells proliferation was assessed by [$^3$H]-thymidine incorporation. Thymidine was added for the last 8 hrs of culture followed by measurement on a scintillation counter. Clone order based on TNF alpha ranking from FIG. 1 is presented. The relative fold change in T cell proliferation (CPM) is shown in FIG. 3A.

Anti-LILRB3 Antibodies Modulate IFN Gamma Release In Vitro.

Total PBMC from healthy donors were treated with anti-LILRB3 hybridoma supernatant or purified antibody (5 microgram/ml) for 24 hours followed by stimulation with LPS (100 ng/ml) for 6 hours. Supernatants were collected and IFN gamma concentrations were measured by ELISA (FIG. 3B). Isotype treatment was used as a control.

Anti-LILRB3 Antibodies Inhibited Allogeneic T Cell Proliferation In Vitro.

Purified human T cells (responders) were labeled with CFSE, and stimulated with irradiated (30 Gy) unrelated donor PBMCs (stimulators) in present of IgG isotype control or the indicated LILRB3 antibodies (5 microgram/ml). The ratio of responder/stimulator is 1/3. After 5 days of co-culture, viable CD4 T cells (upper panel) and CD8 T cells (lower panel) were analyzed by flow cytometry. The representative flow plots were showed as CFSE dilution and percent divided cells.

OKT3-mediated T cell proliferation and IFN gamma secretion was augmented by antagonistic clones, whereas agonistic clones suppress proliferation and INF gamma production or exert no effect on different healthy donors (FIGS. 3A and 3B). The antibodies mediated suppression of mixed lymphocyte reactions (MLR) were presented (FIG. 3C).

Example 4

Proliferation of Leukemia Cells was Suppressed by Anti-LILRB3.

The inventors further tested the effect of anti-LILRB3 mAbs on myeloid leukemia cell proliferation. As shown in FIG. 4, the proliferative activity of U937 and HL60 cells was inhibited by antagonist clones.

Figure 4A:
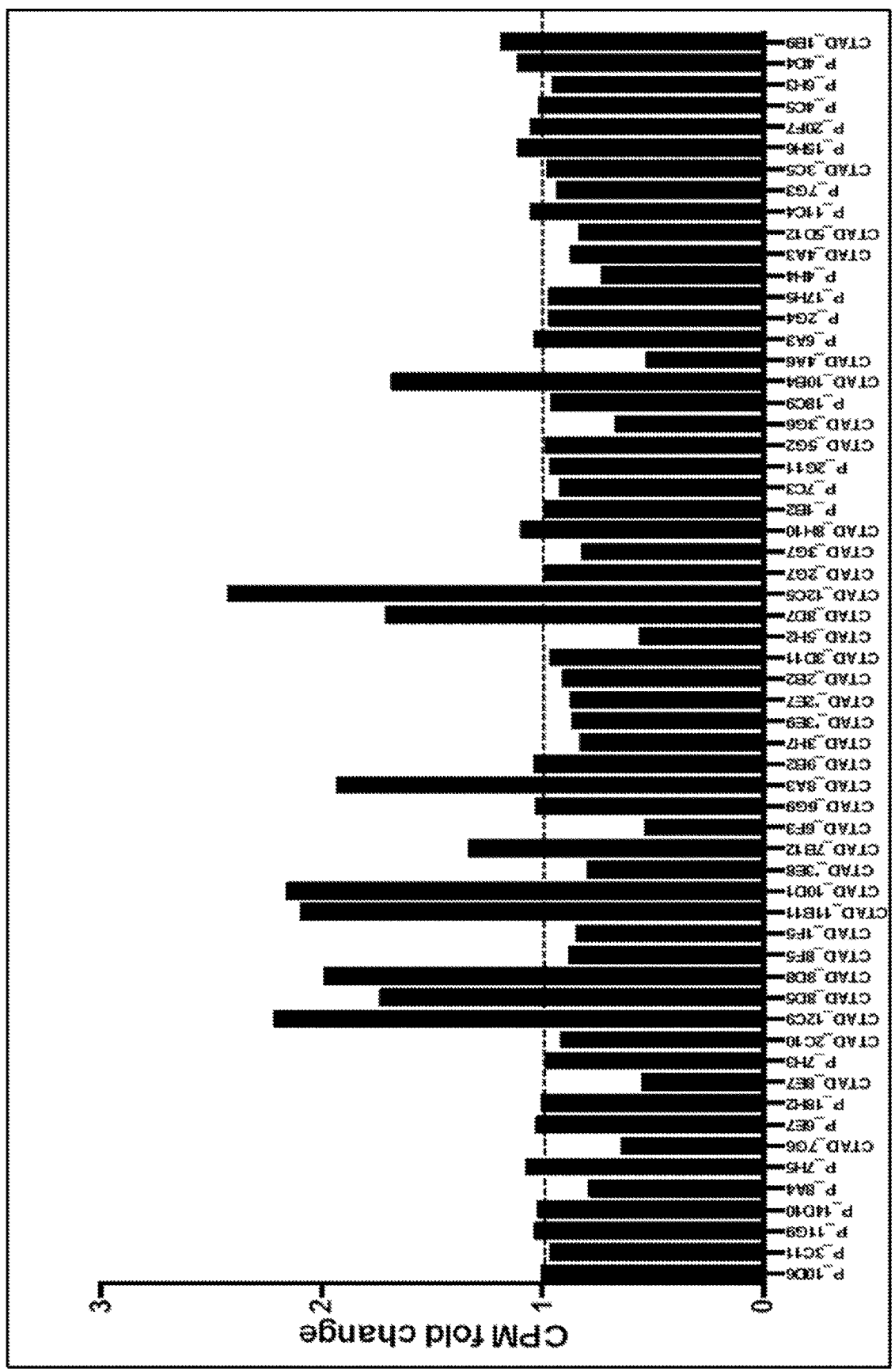
FIG. 4A is a graph showing human myeloid leukemia cells (U937) proliferation (CPM) following treatment with anti-LILRB3 antibody (5 µg/ml), or isotype control for 4 days. U937 cell proliferation was assessed by [3H]-thymidine incorporation. Cells were pulsed with [3H]-thymidine for the last 8 hrs of culture. The relative fold change to control Ig is shown in FIG. 4A.
Figure 4B:
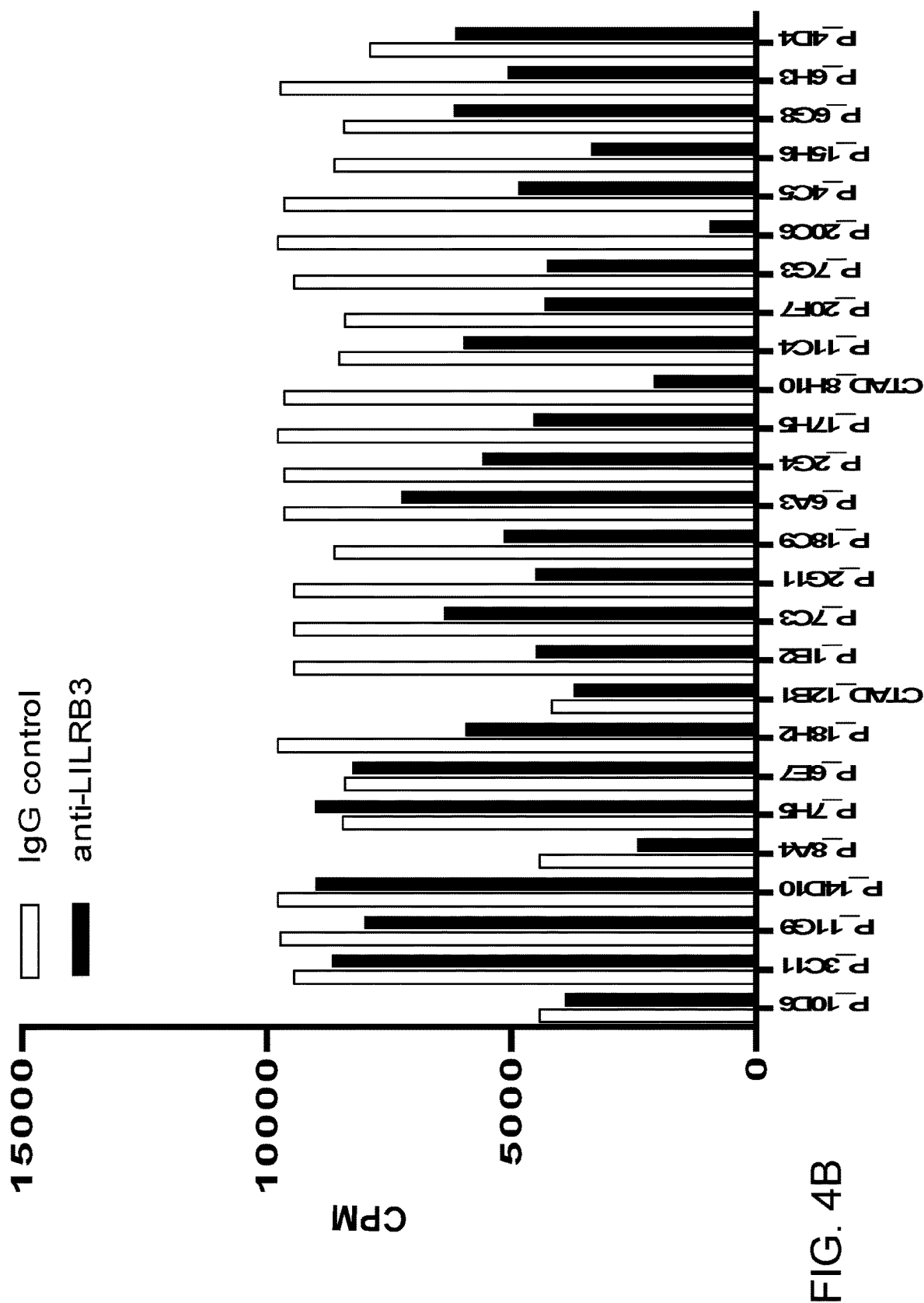
FIGS. 4B-4C are graphs showing human myeloid leukemia cells (HL-60) proliferation (CPM) following treatment with anti-LILRB3 antibody (5 µg/ml), or isotype control for 4 days. HL60 cells were pretreated with INF-γ for 3 days, followed by further treatment with antibody (anti-LILRB3 antibody or isotype control) for 2-5 days. HL60 cell proliferation was measured by [3H]-thymidine incorporation. Cells were pulsed with [3H]-thymidine for the last 8 hrs of culture. Raw data is presented in FIG. 4B, while the relative fold change in cell proliferation (CPM) is shown in FIG. 4C.

LILRB3$^{hi}$U937 leukemia cells were treated with control Ig or mAbs (5 microgram) for 4 days. U937 cell proliferation was assessed by [$^3$H]-thymidine incorporation. Cells were pulsed with [$^3$H]-thymidine for the last 8 hrs of culture. The relative fold change to control Ig is shown in (FIG. 4A).

Figure 4C:
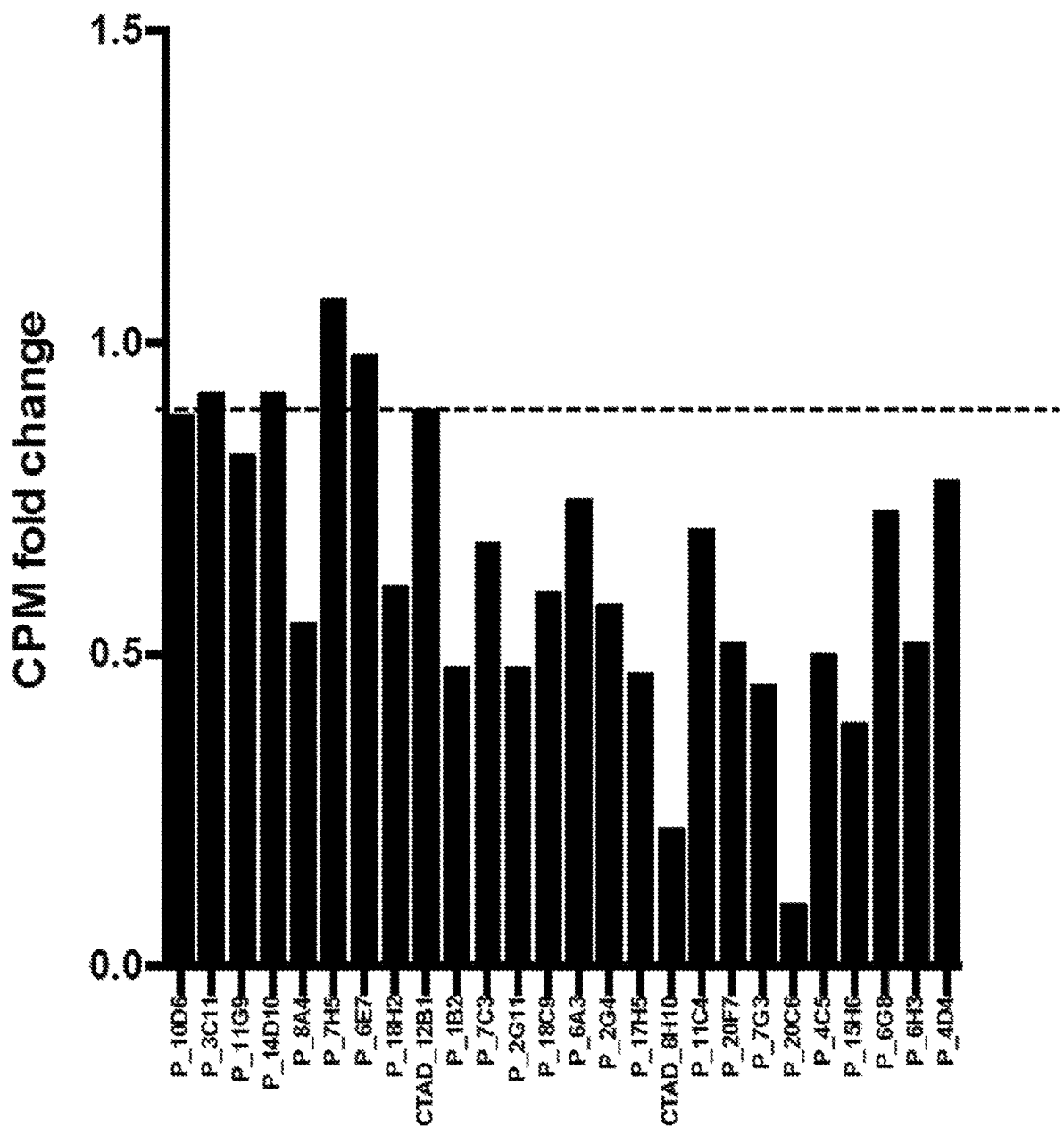

HL60 cells were pretreated with INF gamma for 3 days, followed by further treatment with control Ig or mAbs (5 microgram/ml) for 2-5 days. HL60 cell proliferation was measured by [$^3$H]-thymidine incorporation. Cells were pulsed with [$^3$H]-thymidine for the last 8 hrs of culture. Raw data is presented in (FIG. 4B), while the relative fold change in cell proliferation (CPM) is shown in (FIG. 4C).

Example 5

LILRB3 Antagonists Inhibit the Migratory Ability of LILRB3$^+$ MDAMB231 Breast Cancer Cells.

LILRB3+ breast cancer cells exhibited increased invasive abilities and activated RhoA, indicating that this population may have higher migratory and invasive activities. From the results of transwell invasion assay (FIG. 5A), the trans migration of LILRB3+ MDAMB231 cells was substantially inhibited by antagonistic clone 8H10 and agonistic clone 8D5, but not others at 5 microgram/ml concentrations. Furthermore, activated RhoA was also decreased in antagonistic clone 8H10-treated LILRB3+ MDAMB231 breast cancer cells. In contrast, 12C5, 6F3 and 12B1 clones had little effects on RhoA activation of LILRB3+ MDAMB231 (FIG. 5B). The data supports our hypothesis that blockade of LIRB3 may inhibit the outgrowth, invasion, and metastases of the LILRB3+ cancer cell population.

Figure 5:
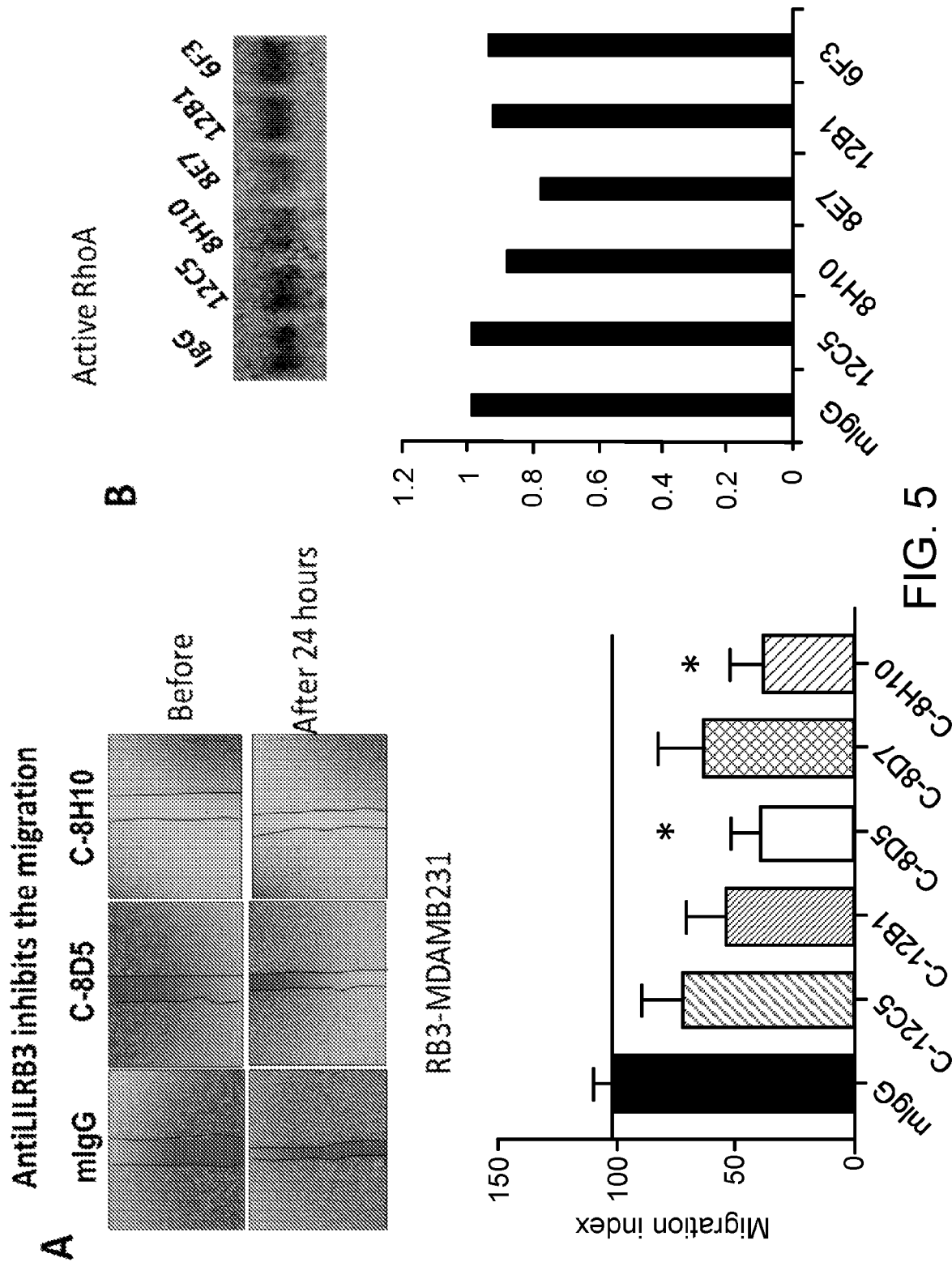
FIG. 5 are graphs showing migration/invasive activity of LILRB3+ MDAMB231 breast cancer cells. (A) The transwell invasion assay was performed to evaluate the migration/invasive activity of LILRB3+ MDAMB231. $3 \times 10^5$ cells were seeded in the upper chamber in the presence of anti-LILRB3 mAbs or control Ig (5 g/ml). After 24 hours, the transwell membrane were stained with Crystal Violet and cells per field were counted. Photos were shown to indicate the migrated cells at the lower bottom panel (20×). (B) The expression of activated RhoA was compared among various anti-LILRB3 mAbs treated LILRB3+ MDAMB231 cells.

The transwell invasion assay was performed to evaluate the migration/invasive activity of LILRB3$^+$ MDAMB231. 3×10$^5$ cells were seeded in the upper chamber in the presence of anti-LILRB3 mAbs or control Ig (5 microgram/ml). After 24 hours, the transwell membrane were stained with Crystal Violet and cells per field were counted. Photos were shown to indicate the migrated cells at the lower bottom panel (20×) (FIG. 5, panel A). The expression of activated RhoA was compared among various anti-LILRB3 mAbs treated LILRB3$^+$ MDAMB231 cells (FIG. 5, panel B).

The LILRB3 Antagonist Inhibits the Growth of Myeloid Leukemia In Vivo.

Figure 6:
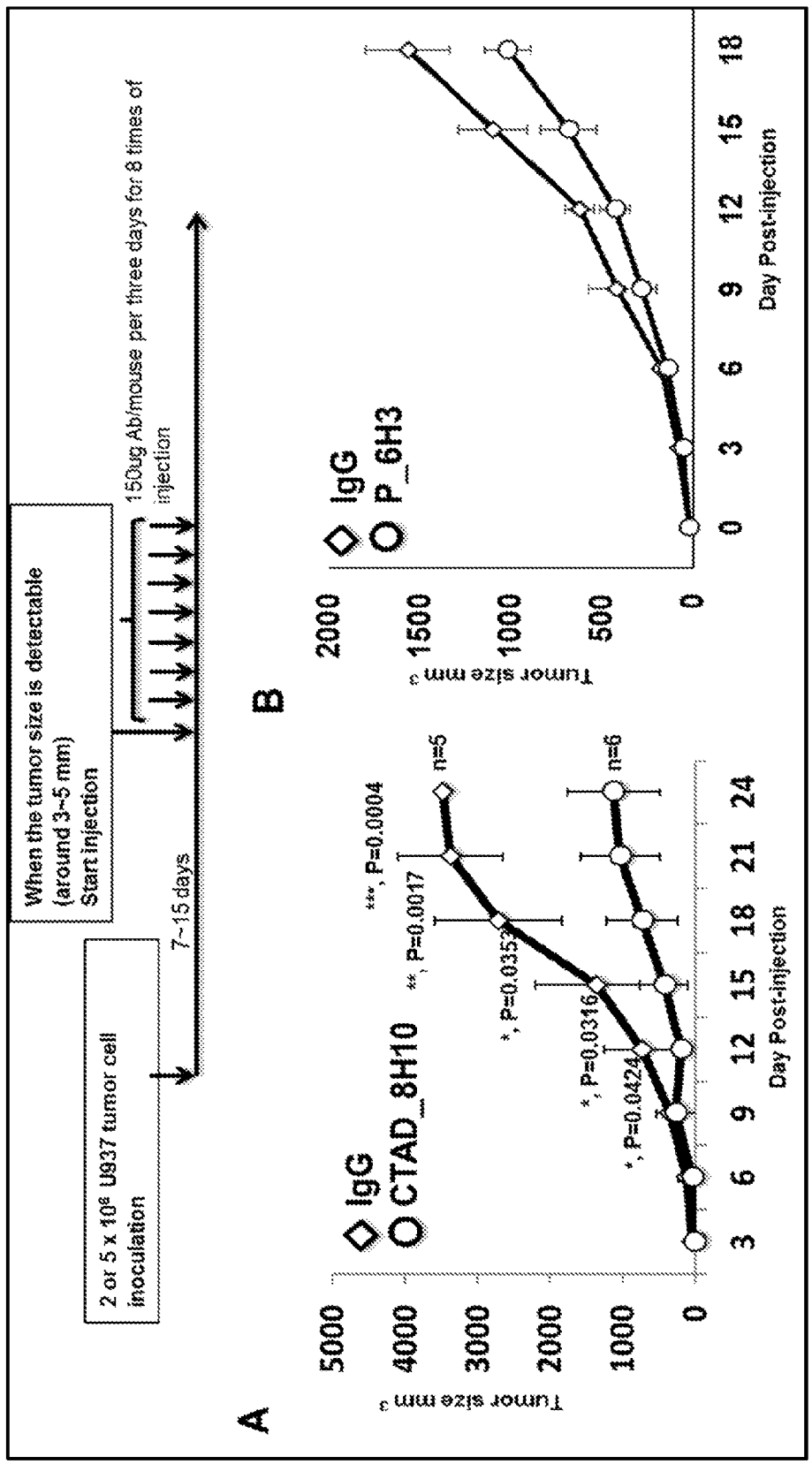
FIG. 6 is a graph showing tumor growth of U937 cells were suppressed by antagonistic clones in xenograft models. NOD/SCID mice were subcutaneously implanted with $2 \times 10^6$ U937 cells. (A) When the tumor size reached 3-5 mm$^2$, anti-LILRB3 mAb, clone CTAD_8H10 (circle line) or control IgG1 (diamond line) (150 microgram/mice, every three days) were infused through I.V. injection. (B) The anti-tumor effect of another clone-anti-LILRB3 mAb, clone P_6H3 (circle line) or control IgG1 (diamond line) (150 microgram/mice, every three days) were presented.

The inventors further evaluated the anti-tumor effect of anti-LILRB3 mAb on U937 leukemia cells in xenograft mouse models. We tested the anti-tumor effect of anti-LILRB3 mAb (clone 8H10, engineered IgG1) and found that the antagonistic clone 8H10 also exerted a strong anti-tumor effect on U937 cells in vivo (FIG. 6). These data suggest that LILRB3 antagonistic antibodies can inhibit the tumor growth.

NOD/SCID mice were subcutaneously implanted with 2×10$^6$ U937 cells. When the tumor size reached 3-5 mm$^2$, anti-LILRB3 mAb, clone 8H10 (circle line) or control IgG1 (diamond line) (150 microgram/mice, every three days) were infused through I.V. injection. The size of tumor was assessed and presented.

Example 6

The Co-Stimulatory Effect of Anti-LILRB3 on Human PBMC Proliferation

Figure 7:
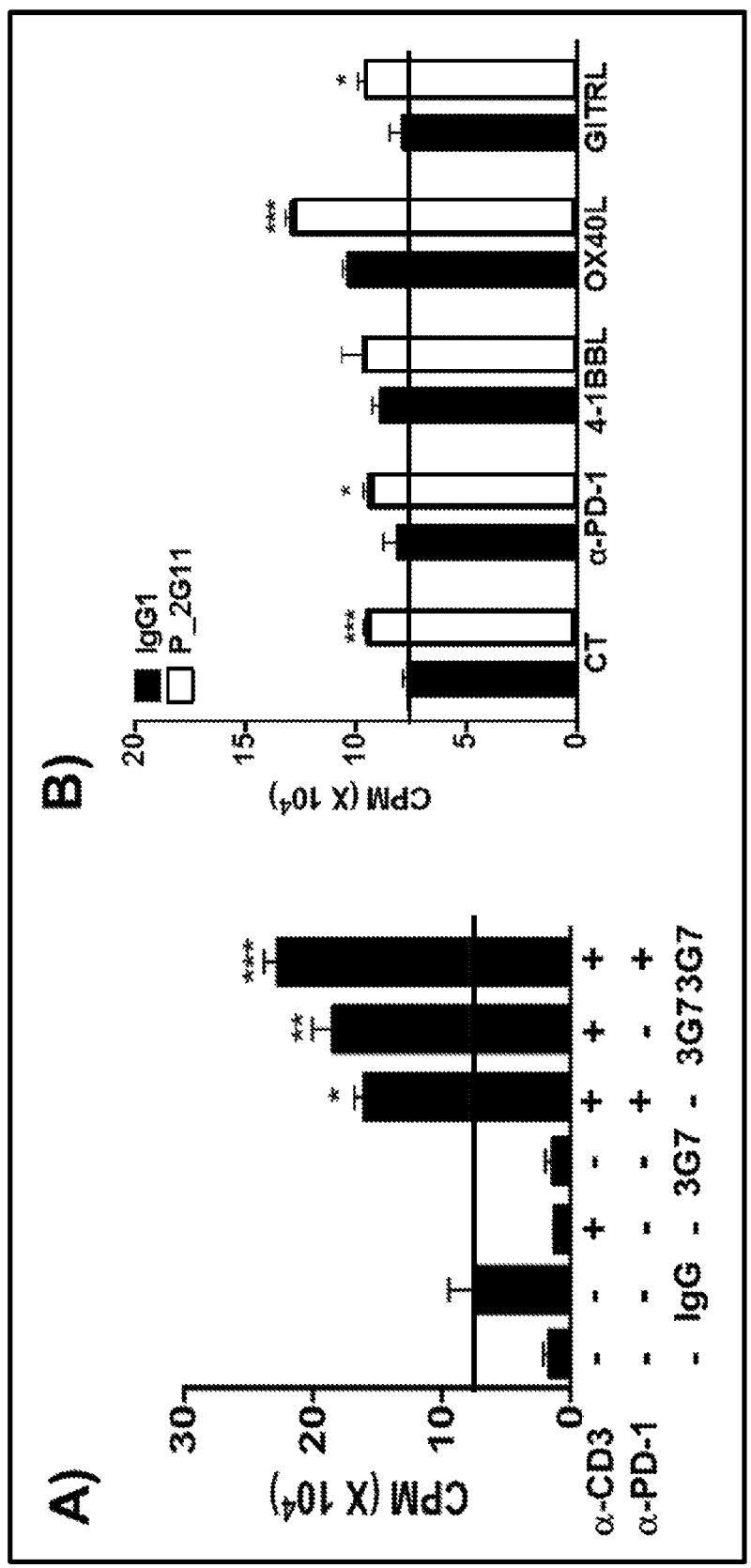
FIG. 7 are graphs showing the co-stimulatory effect of anti-LILRB3 on human PBMC proliferation. $1 \times 10^5$ total PBMC from healthy donors were stimulated with a low dose of anti-CD3 (OKT3, 0.3 microgram/ml) plus anti-LILRB3 Abs (5 microgram/ml) in the presence of 1 ug/ml a-PD-1, 1 ug/ml 4-1BBL, 100 ng/ml OX40L or 1 ug/ml GITRL for 3 days. After 3 day of treatment, T cells proliferation was assessed by [$^3$H]-thymidine incorporation. Thymidine was added for the last 18 hrs of culture followed by measurement on a scintillation counter. The effect of CTAD_3G7 (7A) and P_2G11 (7B) on T cell proliferation (CPM) is shown.

1×10$^5$ total PBMC from healthy donors were stimulated with a low dose (0.3 microgram/ml) anti-CD3 (OKT3) in the presence of anti-LILRB3 mAb supernatants or purified mAbs (5 microgram/ml) 1 ug/ml a-PD-1, 1 ug/ml 4-1BBL, 100 ng/ml OX40L or 1 ug/ml GITRL for 3 days. 3H-Thymidine incorporation assay was performed. After 3 day of treatment, T cells proliferation was assessed by [$^3$H]-thymidine incorporation. Thymidine was added for the last 18 hrs of culture followed by measurement on a scintillation counter. The effect of CTAD_3G7 (FIG. 7 (A)) and P_2G11 (FIG. 7 (B)) on T cell proliferation (CPM) is shown in FIG. 7.

Raw data for Examples 1-6 is provided in Tables 4-7.

Table 7 shows the closest aligning mouse alleles and CDRs1-3 for the selected anti-LILRB3 antibodies (murine).

TABLE 4

| | Clone | Isotype | cyno PBMC MFI | FACS binding | | | | | Myeloid cell-TNFa | | | Myeloid cell-IL-10 | | |
|---|---|---|---|---|---|---|---|---|---|---|---|---|---|---|
| | | | | B1 | B2 | B3 | B4 | A1 | IgG | Avg | Δ | IgG | Avg | Δ |
| P | 6H3 | IgG1 | 1871 | X | X | X | – | X | 1281.0 | 3603.0 | 2.8 | 1608.7 | 1024.0 | 0.6 |
| P | 4H4 | IgG2a | 3199 | X | X | X | – | X | 1225.3 | 3004.8 | 2.5 | 1429.4 | 1004.1 | 0.7 |
| P | 4D4 | IgG2a | 2492 | X | X | X | – | X | 1225.3 | 3587.2 | 2.9 | 1429.4 | 1055.4 | 0.7 |
| P | 15H6 | IgG2a | 226 | X | X | X | – | X | 1225.3 | 3330.6 | 2.7 | 1429.4 | 881.4 | 0.6 |

TABLE 4-continued

| Clone | | Isotype | cyno PBMC MFI | FACS binding | | | | | Myeloid cell-TNFa | | | Myeloid cell-IL-10 | | |
|---|---|---|---|---|---|---|---|---|---|---|---|---|---|---|
| | | | | B1 | B2 | B3 | B4 | A1 | IgG | Avg | Δ | IgG | Avg | Δ |
| P | 11C4 | IgG2a | 336 | X | X | X | – | X | 1225.3 | 3059.2 | 2.5 | 1429.4 | 1025.8 | 0.7 |
| P | 18C9 | IgG2a | 788 | X | X | X | – | X | 1225.3 | 2723.1 | 2.2 | 1429.4 | 905.0 | 0.6 |
| P | 2G11 | IgG1 | 1461 | X | X | X | – | X | 1281.0 | 2684.6 | 2.1 | 1608.7 | 1090.5 | 0.7 |
| P | 2G4 | IgG1 | 1653 | X | X | X | – | X | 1281.0 | 2952.4 | 2.3 | 1608.7 | 882.5 | 0.5 |
| P | 6A3 | IgG1 | 1821 | X | X | X | – | X | 1281.0 | 2920.5 | 2.3 | 1608.7 | 1216.6 | 0.8 |
| P | 4C5 | IgG1 | 1928 | X | X | X | – | X | 1281.0 | 3457.0 | 2.7 | 1608.7 | 1171.9 | 0.7 |
| P | 1B2 | IgG1 | 1542 | X | X | X | – | X | 1281.0 | 2588.1 | 2.0 | 1608.7 | 894.8 | 0.6 |
| P | 17H5 | IgG1 | 1059 | X | X | X | – | X | 1281.0 | 2958.9 | 2.3 | 1608.7 | 906.4 | 0.6 |
| P | 7G3 | IgG1 | 2911 | X | X | X | – | X | 1281.0 | 3314.9 | 2.6 | 1608.7 | 936.9 | 0.6 |
| P | 20F7 | IgG2b | 481 | X | X | X | – | X | 1420.3 | 3583.0 | 2.5 | 691.0 | 726.4 | 1.1 |
| P | 1E9 | IgG2a | 1173 | X | – | X | – | – | 1225.3 | 1441.7 | 1.2 | 1429.4 | 1485.3 | 1.0 |
| P | 2F4 | IgG2a | 857 | X | – | X | – | – | 1225.3 | 1066.2 | 0.9 | 1429.4 | 1558.2 | 1.1 |
| P | 3C9 | IgG1 | 326 | X | – | X | – | – | 1281.0 | 743.1 | 0.6 | 1608.7 | 1923.7 | 1.2 |
| P | 6F3 | IgG1 | 582 | X | – | X | – | – | 1281.0 | 558.0 | 0.4 | 1608.7 | 1799.2 | 1.1 |
| P | 14D10 | IgG1 | 300 | X | – | X | – | – | 1281.0 | 798.3 | 0.6 | 1608.7 | 1629.5 | 1.0 |
| P | 4F9 | IgG2b | 1008 | X | – | X | – | – | 1420.3 | 862.3 | 0.6 | 691.0 | 1453.1 | 2.1 |
| P | 6A2 | IgG1 | 816 | X | – | X | – | – | 1281.0 | 1065.5 | 0.8 | 1608.7 | 1677.4 | 1.0 |
| P | 9G10 | IgG1 | 533 | X | – | X | – | – | 1281.0 | 863.5 | 0.7 | 1608.7 | 1387.6 | 0.9 |
| P | 3C11 | IgG1 | 1259 | X | – | X | – | – | 1281.0 | 640.3 | 0.5 | 1608.7 | 1875.3 | 1.2 |
| P | 5A2 | IgG1 | 3892 | X | – | X | – | – | 1281.0 | 1097.6 | 0.9 | 1608.7 | 2003.5 | 1.2 |
| P | 10E1 | IgG1 | 2055 | X | – | X | – | – | 1281.0 | 941.8 | 0.7 | 1608.7 | 1264.9 | 0.8 |
| P | 8E10 | IgG1 | 875 | X | – | X | – | – | 1281.0 | 1375.8 | 1.1 | 1608.7 | 1489.4 | 0.9 |
| P | 10D6 | IgG1 | 2544 | – | – | X | X | – | 1281.0 | 452.9 | 0.4 | 1608.7 | 1555.9 | 1.0 |
| P | 6G8 | IgG2b | 3840 | X | – | X | – | X | 1420.3 | 3878.0 | 2.7 | 691.0 | 754.0 | 1.1 |
| P | 7C3 | IgG1 | 1190 | X | – | X | – | X | 1281.0 | 2625.5 | 2.0 | 1608.7 | 1576.6 | 1.0 |
| P | 7A4 | IgG1 | 1710 | X | – | X | – | X | 1281.0 | 1060.5 | 0.8 | 1608.7 | 1598.2 | 1.0 |
| P | 9B3 | IgG1 | 384 | X | – | X | – | X | 1281.0 | 992.6 | 0.8 | 1608.7 | 1590.1 | 1.0 |
| P | 8A6 | IgG1 | 2080 | – | – | X | X | – | 1281.0 | 624.7 | 0.5 | 1608.7 | 1946.5 | 1.2 |
| P | 20C6 | IgG1 | 304 | – | – | X | X | X | 1281.0 | 3434.2 | 2.7 | 1608.7 | 1069.9 | 0.7 |
| P | 18H2 | IgG1 | 2419 | – | – | X | – | – | 1281.0 | 1047.3 | 0.8 | 1608.7 | 1774.8 | 1.1 |
| P | 6G3 | IgG2a | 3191 | – | – | X | – | – | 1225.3 | 1000.5 | 0.8 | 1429.4 | 1658.2 | 1.2 |
| P | 18B7 | IgG2b | 1023 | – | – | X | – | – | 1281.0 | 1831.7 | 1.4 | 1608.7 | 1308.7 | 0.8 |
| P | 8H5 | IgG1 | 737 | – | – | X | – | – | 1281.0 | 907.8 | 0.7 | 1608.7 | 1514.9 | 0.9 |
| P | 11G9 | IgG1 | 2239 | – | – | X | – | – | 1281.0 | 764.6 | 0.6 | 1608.7 | 1488.8 | 0.9 |
| P | 18A9 | IgG2b | 551 | – | – | X | – | – | 486 | 1245.8 | 2.6 | 148.2 | 14.5 | 0.1 |
| P | 12B1 | IgG1 | 318 | – | – | X | – | – | 1281.0 | 1385.9 | 1.1 | 1608.7 | 1385.2 | 0.9 |
| P | 8A4 | IgG1 | 1912 | – | – | X | – | – | 1281.0 | 819.2 | 0.6 | 1608.7 | 1428.7 | 0.9 |
| P | 7H5 | IgG2b | 1057 | – | – | X | – | – | 1420.3 | 981.0 | 0.7 | 691.0 | 1438.5 | 2.1 |
| P | 6E7 | IgG2b | 2803 | – | – | X | – | – | 1420.3 | 1150.5 | 0.8 | 691.0 | 1640.2 | 2.4 |
| P | 11G4 | IgG1 | 302 | – | – | X | – | – | 1281.0 | 1437.5 | 1.1 | 1608.7 | 1278.8 | 0.8 |
| P | 4E5 | IgG1 | 1060 | – | – | X | – | – | 1281.0 | 992.5 | 0.8 | 1608.7 | 1736.2 | 1.1 |
| P | 7H3 | IgG2a | 6844 | – | – | X | – | – | 1225.3 | 1123.5 | 0.9 | 1429.4 | 1306.6 | 0.9 |
| P | 18A12 | IgG1 | 578 | – | – | X | – | +/– | 1281.0 | 1608.9 | 1.3 | 1608.7 | 1288.9 | 0.8 |

TABLE 5

| Clone | | T cell proliferation | | | T cell-IFNgamma | | | T cell-IL-10 | | |
|---|---|---|---|---|---|---|---|---|---|---|
| | | IgG | Avg | Δ | IgG | Avg | Δ | IgG | Avg | Δ |
| P | P6H3 | 134294.0 | 143095.0 | 1.1 | 684.0 | 1332.4 | 1.9 | 305.1 | 254.0 | 0.8 |
| P | 4H4 | 114603.0 | 24389.0 | 0.2 | 482.0 | −602.2 | −1.2 | 404.8 | 17.8 | 0.0 |
| P | 4D4 | 114603.0 | 33059.5 | 0.3 | 482.0 | −418.0 | −0.9 | 404.8 | 0.4 | 0.0 |
| P | 15H6 | 114603.0 | 30651.5 | 0.3 | 482.0 | −283.5 | −0.6 | 404.8 | −3.9 | 0.0 |
| P | 11C4 | 114603.0 | 41728.5 | 0.4 | 482.0 | −243.7 | −0.5 | 404.8 | 7.3 | 0.0 |
| P | 18C9 | 114603.0 | 27600.0 | 0.2 | 482.0 | −238.0 | −0.5 | 404.8 | −3.3 | 0.0 |
| P | 2G11 | 134294.0 | 159359.0 | 1.2 | 684.0 | 1520.2 | 2.2 | 305.1 | 317.6 | 1.0 |
| P | 2G4 | 134294.0 | 136140.5 | 1.0 | 699.3 | 694.8 | 1 | 150.2 | 96.6 | 0.6 |
| P | 6A3 | 134294.0 | 147466.0 | 1.1 | 684.0 | 1169.4 | 1.7 | 305.1 | 175.5 | 0.6 |
| P | 4C5 | 134294.0 | 141415.0 | 1.1 | 684.0 | 900.1 | 1.3 | 305.1 | 255.9 | 0.8 |
| P | 1B2 | 134294.0 | 117295.0 | 0.9 | 684.0 | 662.7 | 1.0 | 305.1 | 270.2 | 0.9 |
| P | 17H5 | 134294.0 | 120340.5 | 0.9 | 684.0 | 1252.2 | 1.8 | 305.1 | 324.2 | 1.1 |
| P | 7G3 | 134294.0 | 147412.5 | 1.1 | 684.0 | 1930.5 | 2.8 | 305.1 | 332.3 | 1.1 |
| P | 20F7 | 135183.5 | 160087.0 | 1.2 | 1039.3 | 1050.6 | 1.0 | 288.8 | 215.5 | 0.7 |
| P | 1E9 | 114603.0 | 120914.5 | 1.1 | 717.5 | 917 | 1.3 | 166 | 74.4 | 0.4 |
| P | 2F4 | 114603.0 | 124527.0 | 1.1 | 717.5 | 1728.8 | 2.4 | 166 | 136.3 | 0.8 |
| P | 3C9 | 134294.0 | 94214.0 | 0.7 | 684.0 | 595.4 | 0.9 | 305.1 | 288.3 | 0.9 |
| P | 6F3 | 134294.0 | 101570.0 | 0.8 | 684.0 | 662.7 | 1.0 | 305.1 | 316.9 | 1.0 |
| P | 14D10 | 134294.0 | 120656.5 | 0.9 | 684.0 | 1130.1 | 1.7 | 305.1 | 202.4 | 0.7 |
| P | 4F9 | 135183.5 | 150759.5 | 1.1 | 858.0 | 1837.6 | 2.1 | 167.5 | 107.1 | 0.6 |
| P | 6A2 | 134294.0 | 105176.5 | 0.8 | 699.3 | 1620.0 | 2.3 | 150.2 | 196.9 | 1.3 |

TABLE 5-continued

| | Clone | T cell proliferation | | | T cell-IFNgamma | | | T cell-IL-10 | | |
|---|---|---|---|---|---|---|---|---|---|---|
| | | IgG | Avg | Δ | IgG | Avg | Δ | IgG | Avg | Δ |
| P | 9G10 | 134294.0 | 161861.5 | 1.2 | 699.3 | 1175.5 | 1.7 | 150.2 | 49.0 | 0.3 |
| P | 3C11 | 134294.0 | 111068.5 | 0.8 | 684.0 | 407.6 | 0.6 | 305.1 | 318.8 | 1.0 |
| P | 5A2 | 134294.0 | 131687.0 | 1.0 | 684.0 | 1066.6 | 1.6 | 305.1 | 181.1 | 0.6 |
| P | 10E1 | 134294.0 | 131290.5 | 1.0 | 699.3 | 1307.0 | 1.9 | 150.2 | 18.7 | 0.1 |
| P | 8E10 | 134294.0 | 140365.5 | 1.0 | 684.0 | 1010.9 | 1.5 | 305.1 | 339.8 | 1.1 |
| P | 10D6 | 134294.0 | 103327.5 | 0.8 | 684.0 | 434.7 | 0.6 | 305.1 | 398.2 | 1.3 |
| P | 6G8 | 135183.5 | 142972.0 | 1.1 | 1039.3 | 1488.3 | 1.4 | 288.8 | 278.9 | 1.0 |
| P | 7C3 | 134294.0 | 140439.0 | 1.0 | 684.0 | 524.5 | 0.8 | 305.1 | 205.4 | 0.7 |
| P | 7A4 | 134294.0 | 111613.0 | 0.8 | 699.3 | 912.3 | 1.3 | 150.2 | 89.4 | 0.6 |
| P | 9B3 | 134294.0 | 123247.5 | 0.9 | 684.0 | 911.5 | 1.3 | 305.1 | 255.9 | 0.8 |
| P | 8A6 | 134294.0 | 98695.0 | 0.7 | 684.0 | 1496.3 | 2.2 | 305.1 | 400.0 | 1.3 |
| P | 20C6 | 134294.0 | 161137.5 | 1.2 | 684.0 | 579.5 | 0.8 | 305.1 | 191.9 | 0.6 |
| P | 18H2 | 134294.0 | 105604.5 | 0.8 | 684.0 | 1581.4 | 2.3 | 305.1 | 258.3 | 0.8 |
| P | 6G3 | 114603.0 | 101129.5 | 0.9 | 482.0 | 907.2 | 1.9 | 404.8 | 211.6 | 0.5 |
| P | 18B7 | 134294.0 | 142354.5 | 1.1 | 699.3 | 658.5 | 0.9 | 150.2 | 192.9 | 1.3 |
| P | 8H5 | 134294.0 | 115021.5 | 0.9 | 699.3 | 1184.6 | 1.7 | 150.2 | 223.4 | 1.5 |
| P | 11G9 | 134294.0 | 114304.5 | 0.9 | 684.0 | 905.9 | 1.3 | 305.1 | 268.3 | 0.9 |
| P | 18A9 | 121205 | 84546 | 0.7 | 1039.3 | 1686.4 | 1.6 | 288.8 | 338.5 | 1.2 |
| P | 12B1 | 134294.0 | 144703.5 | 1.1 | 699.3 | 540.6 | 0.8 | 150.2 | 141.2 | 0.9 |
| P | 8A4 | 134294.0 | 149100.5 | 1.1 | 684.0 | 1340.1 | 2.0 | 305.1 | 243.4 | 0.8 |
| P | 7H5 | 135183.5 | 141979.0 | 1.1 | 1039.3 | 1172.7 | 1.1 | 288.8 | 374.6 | 1.3 |
| P | 6E7 | 135183.5 | 108909.0 | 0.8 | 1039.3 | 960.4 | 0.9 | 288.8 | 388.0 | 1.3 |
| P | 11G4 | 134294.0 | 116722.0 | 0.9 | 699.3 | 2000.9 | 2.9 | 150.2 | 177.1 | 1.2 |
| P | 4E5 | 134294.0 | 139216.5 | 1.0 | 684.0 | 1123.3 | 1.6 | 305.1 | 286.4 | 0.9 |
| P | 7H3 | 114603.0 | 151723.0 | 1.3 | 482.0 | 1919.2 | 4.0 | 404.8 | 393.8 | 1.0 |
| P | 18A12 | 134294.0 | 129924.0 | 1.0 | 699.3 | 173.2 | 0.2 | 150.2 | 112.4 | 0.7 |

TABLE 6

| | | cyno PBMC | FACS binding | | | | | Myeloid cell-TNFa | | | Myeloid cell-IL-10 | | |
|---|---|---|---|---|---|---|---|---|---|---|---|---|---|
| Clone | | Isotype | MFI | B1 | B2 | B3 | B4 | A1 | IgG | Avg | Δ | IgG | Avg | Δ |
| CTAD | 7B12 | IgG2a, k | + | − | − | X | − | − | 837.6 | 1145.2 | 1.4 | 240.5 | 183.1 | 0.8 |
| CTAD | 8D5 | IgG2a, k | + | − | − | X | − | X | 3028.1 | 2498.1 | 0.8 | 1552 | 1552 | 1 |
| CTAD | 6G9 | IgG2a, k | + | − | − | X | − | − | 837.6 | 1254.2 | 1.5 | 240.5 | 180.6 | 0.8 |
| CTAD | 3C5 | IgG2a, k | + | − | − | X | − | ND | 2886.8 | 3.4 | | 240.5 | 280.6 | 1.2 |
| CTAD | 9B2 | IgG2a, k | + | − | − | X | − | X | 837.6 | 1334.5 | 1.6 | 240.5 | 202.6 | 0.8 |
| CTAD | 12H11 | IgG2a, k | + | − | − | X | − | − | 837.6 | 1216.4 | 1.5 | 240.5 | 228.0 | 0.9 |
| CTAD | 4A3 | IgG2a, k | + | − | − | X | − | ND | 837.6 | 2630.0 | 3.1 | 240.5 | 181.1 | 0.8 |
| CTAD | 5D12 | IgG2a, k | + | − | − | X | − | − | 837.6 | 2643.6 | 3.2 | 240.5 | 228.7 | 0.9 |
| CTAD | 2E7 | IgG2a, k | + | − | − | X | − | − | 837.6 | 1443.6 | 1.7 | 240.5 | 194.3 | 0.8 |
| CTAD | 1F5 | IgG2a, k | + | − | − | X | − | − | 837.6 | 899.7 | 1.1 | 240.5 | 304.1 | 1.3 |
| CTAD | 8H10 | IgG2a, k | + | − | − | X | − | X | 837.6 | 2041.4 | 2.4 | 240.5 | 180.7 | 0.8 |
| CTAD | 8D7 | IgG2a, k | + | − | − | X | − | − | 837.6 | 1814.1 | 2.2 | 240.5 | 207.3 | 0.9 |
| CTAD | 2C10 | IgG2a, k | + | − | − | X | − | − | 837.6 | 802.7 | 1.0 | 240.5 | 180.8 | 0.8 |
| CTAD | 5G2 | IgG2a, k | + | − | − | X | − | − | 837.6 | 2288.3 | 2.7 | 240.5 | 190.9 | 0.8 |
| CTAD | 11B11 | IgG2a, k | + | − | − | X | − | − | 837.6 | 933.8 | 1.1 | 240.5 | 208.6 | 0.9 |
| CTAD | 3D11 | IgG2a, k | + | − | − | X | − | − | 837.6 | 1520.2 | 1.8 | 240.5 | 205.7 | 0.9 |
| CTAD | 3H7 | IgG2a, k | + | − | − | X | − | − | 837.6 | 1392.1 | 1.7 | 240.5 | 253.1 | 1.1 |
| CTAD | 12F9 | IgG2a, k | + | − | − | X | − | X | 1427.0 | 3049 | 2.1 | 983.4 | 95.1 | 0.1 |
| CTAD | 2B2 | IgG2a, k | + | − | − | X | − | ND | 837.6 | 1480.8 | 1.8 | 240.5 | 237.8 | 1.0 |
| CTAD | 2G7 | IgG2a, k | + | − | − | X | − | − | 837.6 | 1929.2 | 2.3 | 240.5 | 248.5 | 1.0 |
| CTAD | 3E9 | IgG2a, k | + | − | − | X | − | − | 837.6 | 1414.8 | 1.7 | 240.5 | 217.5 | 0.9 |
| CTAD | 10D1 | IgG2a, k | + | − | − | X | − | − | 837.6 | 948.9 | 1.1 | 240.5 | 307.3 | 1.3 |
| CTAD | 12C9 | IgG2a, k | + | − | − | X | − | − | 837.6 | 821.7 | 1.0 | 240.5 | 247.6 | 1.0 |
| CTAD | 10B4 | IgG2a, k | + | − | − | X | − | − | 837.6 | 2408.8 | 2.9 | 240.5 | 224.1 | 0.9 |
| CTAD | 3E8 | IgG2a, k | + | − | − | X | − | − | 837.6 | 981.5 | 1.2 | 240.5 | 246.4 | 1.0 |
| CTAD | 8A3 | IgG2a, k | + | − | − | X | − | − | 837.6 | 1256.5 | 1.5 | 240.5 | 243.0 | 1.0 |
| CTAD | 8E7 | IgG1, k | + | − | − | X | − | − | 720.9 | 551.2 | 0.8 | 227.1 | 252.2 | 1.1 |
| CTAD | 12C5 | IgG2a, k | + | X | − | X | − | X | 720.9 | 1709.5 | 2.4 | 227.1 | 213.6 | 0.9 |
| CTAD | 3G7 | IgG1, k | + | − | − | X | − | − | 720.9 | 1892.1 | 2.6 | 227.1 | 244.6 | 1.1 |
| CTAD | 4A6 | IgG1, k | + | − | − | X | − | − | 720.9 | 2320.9 | 3.2 | 227.1 | 192.7 | 0.8 |
| CTAD | 6F3 | IgG1, k | + | − | X | X | − | X | 837.6 | 1199.7 | 1.4 | 240.5 | 177.0 | 0.7 |
| CTAD | 8F5 | IgG1, k | + | − | − | X | − | − | 720.9 | 759.5 | 1.1 | 227.1 | 207.3 | 0.9 |
| CTAD | 3G6 | IgG2a, k | + | X | − | X | − | − | 837.6 | 2334.5 | 2.8 | 240.5 | 238.7 | 1.0 |
| CTAD | 7G6 | IgG2a, k | + | − | − | X | − | X | 837.6 | 445.2 | 0.5 | 240.5 | 213.4 | 0.9 |
| CTAD | 8D8 | IgG2a, k | + | − | − | X | − | − | 837.6 | 875.5 | 1.0 | 240.5 | 230.1 | 1.0 |
| CTAD | 5H2 | IgG1, k | + | − | − | X | − | − | 720.9 | 1575.5 | 2.2 | 227.1 | 199.3 | 0.9 |
| CTAD | 1B9 | IgG2a, k | + | − | − | X | − | − | 1248 | 1143 | 0.9 | 175.8 | 177.5 | 1.0 |
| CTAD | 1A3 | IgG2a, k | − | − | − | X | − | − | 837.6 | 2109.5 | 2.5 | 240.5 | 207.0 | 0.9 |

TABLE 6-continued

| Clone | | Isotype | cyno PBMC MFI | FACS binding B1 | B2 | B3 | B4 | A1 | Myeloid cell-TNFa IgG | Avg | Δ | Myeloid cell-IL-10 IgG | Avg | Δ |
|---|---|---|---|---|---|---|---|---|---|---|---|---|---|---|
| CTAD | 4G7 | IgG2a, k | – | – | – | – | X | – | – | 1427.0 | 457 | 0.3 | 983.4 | 666.5 | 0.7 |
| CTAD | 12B1 | IgG2a, k | – | – | – | – | X | – | – | 837.6 | 798.2 | 1.0 | 240.5 | 195.2 | 0.8 |

TABLE 7

| Clone | | T cell proliferation IgG | Avg | Δ | T cell-IFNgamma IgG | Avg | Δ | T cell-IL-10 IgG | Avg | Δ |
|---|---|---|---|---|---|---|---|---|---|---|
| CTAD | 7B12 | 147570.0 | 152671 | 1.0 | 35582.0 | 34111.0 | 1.0 | 3143.9 | 2563.2 | 0.8 |
| CTAD | 8D5 | 142300 | 114900 | 0.8 | 5894.4 | 1886.4 | 0.3 | 1224.1 | 1010.8 | 0.8 |
| CTAD | 6G9 | 134036.0 | 130646 | 1.0 | 38806.0 | 30105.0 | 0.8 | 3143.9 | 1969.7 | 0.6 |
| CTAD | 3C5 | 142233.0 | 137079 | 1.0 | 39851.0 | 32803.0 | 0.8 | 3143.9 | 1880.0 | 0.6 |
| CTAD | 9B2 | 147570.0 | 130263.0 | 0.9 | 35582.0 | 28053.0 | 0.8 | 3143.9 | 2403.7 | 0.8 |
| CTAD | 12H11 | 53430.0 | 32063 | 0.6 | 29374.5 | 24624.2 | 0.8 | 3143.9 | 1675.6 | 0.5 |
| CTAD | 4A3 | 142233.0 | 151449 | 1.1 | 39851.0 | 28939.0 | 0.7 | 3143.9 | 1731.0 | 0.6 |
| CTAD | 5D12 | 53430.0 | 46723 | 0.9 | 3377.0 | 3161.0 | 0.9 | 3143.9 | 1784.7 | 0.6 |
| CTAD | 2E7 | 53430.0 | 41863 | 0.8 | 3377.0 | 2745.0 | 0.8 | 3143.9 | 1723.6 | 0.5 |
| CTAD | 1F5 | 142233.0 | 155306 | 1.1 | 39851.0 | 36500.0 | 0.9 | 3143.9 | 2318.9 | 0.7 |
| CTAD | 8H10 | 147570.0 | 140077 | 0.9 | 35582.0 | 29288.0 | 0.8 | 3143.9 | 2202.7 | 0.7 |
| CTAD | 8D7 | 134036.0 | 127937 | 1.0 | 38806.0 | 32530.0 | 0.8 | 3143.9 | 2574.8 | 0.8 |
| CTAD | 2C10 | 142233.0 | 152767 | 1.1 | 39851.0 | 32440.0 | 0.8 | 3143.9 | 1899.1 | 0.6 |
| CTAD | 5G2 | 142233.0 | 150690 | 1.1 | 39851.0 | 27399.0 | 0.7 | 3143.9 | 1985.6 | 0.6 |
| CTAD | 11B11 | 134036.0 | 117943 | 0.9 | 38806.0 | 33784.0 | 0.9 | 3143.9 | 1568.9 | 0.5 |
| CTAD | 3D11 | 142233.0 | 147938 | 1.0 | 39851.0 | 27208.0 | 0.7 | 3143.9 | 1927.9 | 0.6 |
| CTAD | 3H7 | 142233.0 | 155607 | 1.1 | 39851.0 | 28480.0 | 0.7 | 3143.9 | 1839.9 | 0.6 |
| CTAD | 12F9 | 69047.5 | 91777 | 1.3 | 684 | 1332.4 | 1.9 | 305.1 | 254.0 | 0.8 |
| CTAD | 2B2 | 142233.0 | 144980 | 1.0 | 39851.0 | 33979.0 | 0.9 | 3143.9 | 2490.3 | 0.8 |
| CTAD | 2G7 | 142233.0 | 149156 | 1.0 | 39851.0 | 26718.0 | 0.7 | 3143.9 | 2321.2 | 0.7 |
| CTAD | 3E9 | 142233.0 | 158235 | 1.1 | 39851.0 | 30914.0 | 0.8 | 3143.9 | 1750.0 | 0.6 |
| CTAD | 10D1 | 122580.0 | 30799 | 0.3 | 38806.0 | 33121.0 | 0.9 | 3143.9 | 1385.7 | 0.4 |
| CTAD | 12C9 | 134036.0 | 134453 | 1.0 | 38806.0 | 30959.0 | 0.8 | 3143.9 | 1728.3 | 0.5 |
| CTAD | 10B4 | 134036.0 | 124943 | 0.9 | 38806.0 | 31677.0 | 0.8 | 3143.9 | 1913.4 | 0.6 |
| CTAD | 3E8 | 142233.0 | 144935 | 1.0 | 39851.0 | 32481.0 | 0.8 | 3143.9 | 2325.4 | 0.7 |
| CTAD | 8A3 | 134036.0 | 129001 | 1.0 | 38806.0 | 34919.0 | 0.9 | 3143.9 | 1922.2 | 0.6 |
| CTAD | 8E7 | 43225.0 | 38045 | 0.9 | 22029.3 | 17217.4 | 0.8 | 3058.0 | 2140.1 | 0.7 |
| CTAD | 12C5 | 136704.0 | 135857 | 1.0 | 32267.0 | 28253.0 | 0.9 | 3058.0 | 1448.3 | 0.5 |
| CTAD | 3G7 | 133475.0 | 127132 | 1.0 | 31994.0 | 27045.0 | 0.8 | 3058.0 | 1563.8 | 0.5 |
| CTAD | 4A6 | 147320.0 | 135817 | 0.9 | 37208.0 | 29924.0 | 0.8 | 3143.9 | 2254.0 | 0.7 |
| CTAD | 6F3 | 134036.0 | 117635 | 0.9 | 37208.0 | 29124.0 | 0.8 | 3143.9 | 1704.3 | 0.5 |
| CTAD | 8F5 | 136704.0 | 134440 | 1.0 | 32267.0 | 32603.0 | 1.0 | 3058.0 | 2535.2 | 0.8 |
| CTAD | 3G6 | 147570.0 | 127253 | 0.9 | 35582.0 | 32639.0 | 0.9 | 3143.9 | 2156.3 | 0.7 |
| CTAD | 7G6 | 134036.0 | 133441 | 1.0 | 38806.0 | 27372.0 | 0.7 | 3143.9 | 2898.5 | 0.9 |
| CTAD | 8D8 | 134036.0 | 120193 | 0.9 | 38806.0 | 31867.0 | 0.8 | 3143.9 | 2146.5 | 0.7 |
| CTAD | 5H2 | 133475.0 | 125114 | 0.9 | 31994.0 | 25773.0 | 0.8 | 3058.0 | 2138.7 | 0.7 |
| CTAD | 1B9 | 53430.0 | 31819 | 0.6 | 29374.5 | 16197.2 | 0.6 | 3143.9 | 1368.0 | 0.4 |
| CTAD | 1A3 | 142233.0 | 144507 | 1.0 | 39851.0 | 36481.0 | 0.9 | 3143.9 | 3439.5 | 1.1 |
| CTAD | 4G7 | 69047.5 | 69629 | 1.0 | 12283.2 | 15641 | 1.3 | 836.4 | 1079 | 1.3 |
| CTAD | 12B1 | 134036.0 | 111211 | 0.8 | 38806.0 | 31613.0 | 0.8 | 3143.9 | 1632.2 | 0.5 |

TABLE 8

| Clone | | Isotype | cyno PBMC MFI | Kappa VJ alleles | | heavy chain VJD alleles | | |
|---|---|---|---|---|---|---|---|---|
| P | 6H3 | IgG1 | 1871 | IGKV8-24*01 F | IGKJ1*01 F | IGHV9-3*01 F | IGHJ4*01 F | IGHD4-1*01 F |
| P | 4H4 | IgG2a | 3199 | IGKV8-24*01 F | IGKJ1*01 F | IGHV9-3*01 F | IGHJ4*01 F | IGHD2-12*01 F |
| P | 4D4 | IgG2a | 2492 | IGKV8-24*01 F | IGKJ1*01 F | IGHV9-3*01 F | IGHJ4*01 F | IGHD2-12*01 F |
| P | 15H6 | IgG2a | 226 | IGKV8-24*01 F | IGKJ1*01 F | IGHV9-3*01 F | IGHJ4*01 F | IGHD2-12*01 F |
| P | 11C4 | IgG2a | 336 | IGKV8-24*01 F | IGKJ1*01 F | IGHV9-3*01 F | IGHJ4*01 F | IGHD2-12*01 F |
| P | 18C9 | IgG2a | 788 | IGKV8-24*01 F | IGKJ1*01 F | IGHV9-3*01 F | IGHJ4*01 F | IGHD2-12*01 F |
| P | 2G11 | IgG1 | 1461 | IGKV8-24*01 F | IGKJ5*01 F | IGHV9-3*01 F | IGHJ2*01 F | IGHD5-7*01 ORF |
| P | 2G4 | IgG1 | 1653 | IGKV8-24*01 F | IGKJ5*01 F | IGHV9-3*01 F | IGHJ2*01 F | IGHD5-7*01 ORF |
| P | 6A3 | IgG1 | 1821 | IGKV8-24*01 F | IGKJ5*01 F | IGHV9-3*01 F | IGHJ2*01 F | IGHD5-7*01 ORF |
| P | 4C5 | IgG1 | 1928 | IGKV8-24*01 F | IGKJ1*01 F | IGHV9-3*01 F | IGHJ4*01 F | IGHD2-5*01 F |
| P | 1B2 | IgG1 | 1542 | IGKV8-24*01 F | IGKJ1*01 F | IGHV9-3*01 F | IGHJ4*01 F | IGHD2-5*01 F |
| P | 17H5 | IgG1 | 1059 | IGKV8-24*01 F | IGKJ1*01 F | IGHV9-3*01 F | IGHJ4*01 F | IGHD2-5*01 F |

TABLE 8-continued

| Clone | | Isotype | cyno PBMC MFI | Kappa VJ alleles | | heavy chain VJD alleles | | |
|---|---|---|---|---|---|---|---|---|
| P | 7G3 | IgG1 | 2911 | IGKV8-24*01 F | IGKJ1*02 F | IGHV9-3*01 F | IGHJ4*01 F | IGHD2-5*01 F |
| P | 20F7 | IgG2b | 481 | IGKV10-96*01 F | IGKJ2*01 F | IGHV3-6*01 F | IGHJ4*01 F | IGHD1-1*01 F |
| P | 1E9 | IgG2a | 1173 | IGKV3-9*01 F | IGKJ1*01 F | IGHV9-3*01 F | IGHJ2*01 F | IGHD1-1*01 F |
| P | 2F4 | IgG2a | 857 | IGKV3-9*01 F | IGKJ1*01 F | IGHV9-3*01 F | IGHJ2*01 F | IGHD1-1*01 F |
| P | 3C9 | IgG1 | 326 | IGKV14-111*01 F | IGKJ5*01 F | IGHV1-64*01 F | IGHJ3*01 F | IGHD4-1*01 F |
| P | 6F3 | IgG1 | 582 | IGKV14-111*01 F | IGKJ5*01 F | IGHV2-3*01 F | IGHJ4*01 F | IGHD4-1*01 F |
| P | 14D10 | IgG1 | 300 | IGKV14-111*01 F | IGKJ5*01 F | IGHV1-78*01 F | IGHJ2*01 F | IGHD4-1*01 F |
| P | 4F9 | IgG2b | 1008 | IGKV4-74*01 F | IGKJ4*01 F | IGHV1-9*01 F | IGHJ2*01 F | IGHD1-3*01 F |
| P | 6A2 | IgG1 | 816 | IGKV4-72*01 F | IGKJ2*01 F | IGHV9-3*01 F | IGHJ2*01 F | IGHD1-1*01 F |
| P | 9G10 | IgG1 | 533 | IGKV6-13*01 (F) | IGKJ5*01 F | IGHV1-55*01 F | IGHJ1*03 F | IGHD3-3*01 F |
| P | 3C11 | IgG1 | 1259 | IGKV4-63*01 F | IGKJ4*01 F | IGHV8-8*01 F | IGHJ2*01 F | IGHD2-1*01 F |
| P | 5A2 | IgG1 | 3892 | IGKV4-55*01 F | IGKJ5*01 F | IGHV1-64*01 F | IGHJ2*01 F | IGHD2-13*01 F |
| P | 10E1 | IgG1 | 2055 | IGKV4-57-1*01 F | IGKJ2*01 F | IGHV4-82*01 F | IGHJ2*01 F | IGHD1-1*01 F |
| P | 8E10 | IgG1 | 875 | IGKV1-110*01 F | IGKJ1*01 F | IGHV5-17*01 F | IGHJ4*01 F | IGHD1-1*01 F |
| P | 10D6 | IgG1 | 2544 | IGKV1-110*01 F | IGKJ2*01 F | IGHV5-17*01 F | IGHJ4*01 F | IGHD2-4*01 F |
| P | 6G8 | IgG2b | 3840 | IGKV10-96*01 F | IGKJ2*01 F | IGHV3-6*01 F | IGHJ4*01 F | IGHD1-1*01 F |
| P | 7C3 | IgG1 | 1190 | IGKV6-15*01 F | IGKJ4*01 F | IGHV5-17*01 F | IGHJ1*03 F | IGHD2-10*02 F |
| P | 7A4 | IgG1 | 1710 | IGKV4-57*01 F | IGKJ1*01 F | IGHV14-4*01 F | IGHJ2*01 F | IGHD4-1*01 F |
| P | 9B3 | IgG1 | 384 | IGKV6-13*01 (F) | IGKJ2*01 F | IGHV1-47*01 F | IGHJ3*01 F | IGHD1-1*02 F |
| P | 8A6 | IgG1 | 2080 | IGKV15-103*01 | IGKJ1*01 F | IGHV1-42*01 F | IGHJ2*01 F | IGHD1-1*01 F |
| P | 20C6 | IgG1 | 304 | IGKV12-98*01 F | IGKJ4*01 F | IGHV5-17*01 F | IGHJ3*01 F | IGHD1-1*01 F |
| P | 18H2 | IgG1 | 2419 | IGKV14-111*01 F | IGKJ5*01 F | IGHV1-64*01 F | IGHJ3*01 F | IGHD4-1*01 F |
| P | 6G3 | IgG2a | 3191 | IGKV8-27*01 F | IGKJ4*01 F | IGHV2-2*01 F | IGHJ4*01 F | IGHD1-1*01 F |
| P | 18B7 | IgG2b | 1023 | IGKV4-74*01 F | IGKJ4*01 F | IGHV1-9*01 F | IGHJ4*01 F | IGHD1-2*01 F |
| P | 8H5 | IgG1 | 737 | IGKV4-74*01 F | IGKJ4*01 F | IGHV1-9*01 F | IGHJ4*01 F | IGHD1-2*01 F |
| P | 11G9 | IgG1 | 2239 | IGKV4-74*01 F | IGKJ2*01 F | IGHV1-9*01 F | IGHJ2*01 F | IGHD1-1*01 F |
| P | 18A9 | IgG2b | 551 | IGKV6-15*01 F | IGKJ2*01 F | IGHV1-26*01 F | IGHJ4*01 F | IGHD4-1*01 F |
| P | 12B1 | IgG1 | 318 | IGKV6-15*01 F | IGKJ2*01 F | IGHV14-2*01 F | IGHJ2*01 F | IGHD1-1*01 F |
| P | 8A4 | IgG1 | 1912 | IGKV4-57-1*01 F | IGKJ2*01 F | IGHV4-82*01 F | IGHJ2*01 F | IGHD1-1*01 F |
| P | 7H5 | IgG2b | 1057 | IGKV6-25*01 F | IGKJ1*01 F | IGHV2-2*01 F | IGHJ4*01 F | IGHD1-1*01 F |
| P | 6E7 | IgG2b | 2803 | IGKV1-88*01 F | IGKJ1*01 F | IGHV1-19*01 F | IGHJ4*01 F | IGHD2-1*01 F |
| P | 11G4 | IgG1 | 302 | IGKV1-110*01 F | IGKJ2*01 F | IGHV2-3*01 F | IGHJ4*01 F | IGHD4-1*01 F |
| P | 4E5 | IgG1 | 1060 | IGKV8-30*01 F | IGKJ1*01 F | IGHV5-17*01 F | IGHJ4*01 F | IGHD2-3*01 F |
| P | 7H3 | IgG2a | 6844 | IGKV10-94*01 F | IGKJ1*01 F | IGHV5-17*01 F | IGHJ4*01 F | IGHD2-4*01 F |
| P | 18A12 | IgG1 | 578 | IGKV10-96*01 F | IGKJ1*01 F | IGHV5-9-1*02 F | IGHJ4*01 F | IGHD1-1*01 F |
| CTAD | 7B12 | IgG2a, k | + | IGKV8-24*01 F | IGKJ5*01 F | IGHV1S56*01 F | IGHJ4*01 F | |
| CTAD | 8D5 | IgG2a, k | + | IGKV6-14*01 F | IGKJ4*01 F | IGHV1S56*01 F | IGHJ4*01 F | |
| CTAD | 6G9 | IgG2a, k | + | IGKV6-14*01 F | IGKJ4*01 F | IGHV1S56*01 F | IGHJ4*01 F | |
| CTAD | 3C5 | IgG2a, k | + | IGKV6-14*01 F | IGKJ4*01 F | IGHV1S56*01 F | IGHJ4*01 F | |
| CTAD | 9B2 | IgG2a, k | + | IGKV6-14*01 F | IGKJ4*01 F | IGHV1S56*01 F | IGHJ4*01 F | |
| CTAD | 12H11 | IgG2a, k | + | IGKV6-14*01 F | IGKJ4*01 F | IGHV1S56*01 F | IGHJ4*01 F | |
| CTAD | 4A3 | IgG2a, k | + | IGKV6-14*01 F | IGKJ4*01 F | IGHV1S56*01 F | IGHJ4*01 F | |
| CTAD | 5D12 | IgG2a, k | + | IGKV6-14*01 F | IGKJ4*01 F | IGHV1S56*01 F | IGHJ4*01 F | |
| CTAD | 2E7 | IgG2a, k | + | IGKV6-14*01 F | IGKJ4*01 F | IGHV1S56*01 F | IGHJ4*01 F | |
| CTAD | 1F5 | IgG2a, k | + | IGKV6-14*01 F | IGKJ4*01 F | IGHV1S56*01 F | IGHJ4*01 F | |
| CTAD | 8H10 | IgG2a, k | + | IGKV6-14*01 F | IGKJ4*01 F | IGHV1S56*01 F | IGHJ4*01 F | |
| CTAD | 8D7 | IgG2a, k | + | IGKV6-14*01 F | IGKJ4*01 F | IGHV1S56*01 F | IGHJ4*01 F | |
| CTAD | 2C10 | IgG2a, k | + | IGKV6-14*01 F | IGKJ4*01 F | IGHV1S56*01 F | IGHJ4*01 F | |
| CTAD | 5G2 | IgG2a, k | + | IGKV6-14*01 F | IGKJ4*01 F | IGHV1S56*01 F | IGHJ4*01 F | |
| CTAD | 11B11 | IgG2a, k | + | IGKV6-14*01 F | IGKJ4*01 F | IGHV1S56*01 F | IGHJ4*01 F | |
| CTAD | 3D11 | IgG2a, k | + | IGKV6-14*01 F | IGKJ4*01 F | IGHV1S56*01 F | IGHJ4*01 F | |
| CTAD | 3H7 | IgG2a, k | + | IGKV6-14*01 F | IGKJ4*01 F | IGHV1S56*01 F | IGHJ4*01 F | |
| CTAD | 12F9 | IgG2a, k | + | IGKV6-14*01 F | IGKJ4*01 F | IGHV1S56*01 F | IGHJ4*01 F | |
| CTAD | 2B2 | IgG2a, k | + | IGKV6-14*01 F | IGKJ4*01 F | IGHV1S56*01 F | IGHJ4*01 F | |
| CTAD | 2G7 | IgG2a, k | + | IGKV6-14*01 F | IGKJ4*01 F | IGHV1S56*01 F | IGHJ4*01 F | |
| CTAD | 3E9 | IgG2a, k | + | IGKV6-14*01 F | IGKJ4*01 F | IGHV1S56*01 F | IGHJ4*01 F | |
| CTAD | 10D1 | IgG2a, k | + | IGKV6-14*01 F | IGKJ4*01 F | IGHV1S56*01 F | IGHJ4*01 F | |
| CTAD | 12C9 | IgG2a, k | + | IGKV6-14*01 F | IGKJ4*01 F | IGHV1S56*01 F | IGHJ4*01 F | |
| CTAD | 10B4 | IgG2a, k | + | IGKV6-14*01 F | IGKJ4*01 F | IGHV1S56*01 F | IGHJ4*01 F | |
| CTAD | 3E8 | IgG2a, k | + | IGKV6-14*01 F | IGKJ4*01 F | IGHV1S56*01 F | IGHJ4*01 F | |
| CTAD | 8A3 | IgG2a, k | + | IGKV8-30*01 F | IGKJ1*01 F | IGHV2-9-2*01 F | IGHJ4*01 F | IGHD2-4*01 F |
| CTAD | 8E7 | IgG1, k | + | IGKV10-96*01 F | IGKJ1*01 F | IGHV2-9*02 F | IGHJ1*01 F | IGHD1-1*01 F |
| CTAD | 12C5 | IgG1, k | + | IGKV10-94*01 F | IGKJ1*01 F | IGHV2-9*02 F | IGHJ3*01 F | IGHD3-3*01 F |
| CTAD | 3G7 | IgG1, k | + | IGKV12-44*01 F | IGKJ2*01 F | IGHV9-3-1*01 F | IGHJ4*01 F | IGHD2-14*01 F |
| CTAD | 4A6 | IgG1, k | + | IGKV12-44*01 F | IGKJ2*01 F | IGHV9-3-1*01 F | IGHJ4*01 F | IGHD2-14*01 F |
| CTAD | 6F3 | IgG1, k | + | IGKV12-44*01 F | IGKJ1*02 F | IGHV9-3*03 F | IGHJ2*01 F | IGHD2-2*01 F |
| CTAD | 8F5 | IgG1, k | + | IGKV3-5*01 F | IGKJ2*01 F | IGHV1-18*01 F | IGHJ2*01 F | IGHD1-1*02 F |
| CTAD | 3G6 | IgG2a, k | + | IGKV3-5*01 F | IGKJ4*01 F | IGHV1-18*01 F | IGHJ3*01 F | IGHD1-1*01 F |
| CTAD | 7G6 | IgG2a, k | + | IGKV3-5*01 F | IGKJ1*01 F | IGHV1S29*02 F | IGHJ4*01 F | |
| CTAD | 8D8 | IgG2a, k | + | IGKV6-14*01 F | IGKJ4*01 F | IGHV1S56*01 F | IGHJ4*01 F | IGHD4-1*01 F |
| CTAD | 5H2 | IgG1, k | + | IGKV3-12*01 F | IGKJ4*01 F | IGHV8-13*01 P | IGHJ4*01 F | |
| CTAD | 1B9 | IgG2a, k | + | IGKV6-14*01 F | IGKJ4*01 F | IGHV1S56*01 F | IGHJ4*01 F | |
| CTAD | 1A3 | IgG2a, k | − | | | IGHV9-3-1*01 F | IGHJ3*01 F | IGHD1-1*01 F |
| CTAD | 4G7 | IgG2a, k | − | IGKV8-30*01 F | IGKJ1*01 F | IGHV2-9-2*01 F | IGHJ4*01 F | IGHD2-4*01 F |
| CTAD | 12B1 | IgG2a, k | − | IGKV4-50*01 F | IGKJ2*01 F | IGHV3-6*02 F | IGHJ3*01 F | IGHD1-1*02 F |
| CTAD | 2G2 | untested | − | IGKV4-74*01 F | IGKJ4*01 F | IGHV5-4*02 F | IGHJ4*01 F | IGHD1-1*01 F |

TABLE 8-continued

| Clone | | Isotype | cyno PBMC MFI | Kappa VJ alleles | | heavy chain VJD alleles | | |
|---|---|---|---|---|---|---|---|---|
| CTAD | 9D1 | untested | – | IGKV12-46*01 F | IGKJ2*01 F | IGHV3-6*02 F | IGHJ2*01 F | IGHD2-1*01 F |
| CTAD | 5H6 | untested | – | IGKV4-74*01 F | IGKJ4*01 F | IGHV5-4*02 F | IGHJ4*01 F | IGHD5-5*01 ORF |
| CTAD | 1E10 | untested | – | IGKV3-5*01 F | IGKJ5*01 F | IGHV1S29*02 F | IGHJ4*01 F | |
| CTAD | 12B2 | untested | – | IGKV3-12*01 F | IGKJ2*01 F | IGHV3-8*02 F | IGHJ3*01 F | IGHD2-3*01 F |
| CTAD | 7E6 | untested | – | IGKV12-46*01 F | IGKJ2*01 F | IGHV3-6*02 F | IGHJ2*01 F | IGHD2-1*01 F |
| CTAD | 8B6 | untested | – | IGKV12-46*01 F | IGKJ5*01 F | IGHV1-9*01 F | IGHJ4*01 F | IGHD2-10*02 F |
| CTAD | 1E12 | untested | – | IGKV1-135*01 F | IGKJ2*01 F | IGHV6-6*01 F | IGHJ4*01 F | IGHD1-1*01 F |
| CTAD | 6A10 | untested | – | IGKV10-94*01 F | IGKJ1*01 F | IGHV2-9*02 F | IGHJ4*01 F IGHD3-1*01 F | IGHD3-1*01 F |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An antibody or antigen-binding fragment thereof that specifically binds to leukocyte immunoglobulin-like receptor B3 (LILRB3), wherein the antibody or antigen-binding fragment thereof comprises a heavy chain variable region (VH) and a light chain variable region (VL), wherein:

the VH comprises VH CDR1, CDR2, and CDR3 comprising the amino acid sequences GYTFINYY (SEQ ID NO: 50), IYPGNINS (SEQ ID NO: 64) and CAMTNSSAMDYW (SEQ ID NO: 81), respectively, and the VL comprises VL CDR1, CDR2, and CDR3 comprising the amino acid sequences QNIRTA (SEQ ID NO: 10), LAS (SEQ ID NO: 22) and CLQHWNYPFTF (SEQ ID NO: 38), respectively.

2. An isolated nucleic acid molecule encoding the antibody or antigen-binding fragment thereof of claim 1.

3. A vector comprising the nucleic acid molecule of claim 2.

4. An isolated host cell comprising the vector of claim 3.

5. A method for producing an anti-LILRB3 antibody or antigen-binding fragment thereof comprising the steps of (a) culturing the isolated host cell of claim 4 under conditions suitable for expression of the antibody or antigen-binding fragment thereof by the isolated host cell; and (b) recovering the antibody or antigen-binding fragment thereof.

6. A composition comprising the antibody or antigen-binding fragment thereof of claim 1 and a suitable pharmaceutical carrier.

7. A method of treating cancer in a mammal, the method comprising administering to the mammal a therapeutically effective amount of the antibody or antigen-binding fragment thereof of claim 1.

8. A method of decreasing a pro-inflammatory immune response in a mammal, the method comprising administering to the mammal a therapeutically effective amount of the antibody or antigen-binding fragment thereof of claim 1.

9. A method of treating inflammation, an autoimmune disease, or transplant rejection in a mammal, the method comprising administering to the mammal a therapeutically effective amount of the antibody or antigen-binding fragment thereof of claim 1.

* * * * *

```
                        SEQUENCE LISTING

<160> NUMBER OF SEQ ID NOS: 272

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Ser Leu Leu Ile Ser Thr Asn Gln Lys Asn Tyr
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gln Ser Leu Phe Ile Ser Thr Asn Gln Lys Asn Tyr
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ser Leu Leu Ile Ser Thr Asn Gln Ile Asn Tyr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4
```

Gln Asn Leu Leu Asn Ser Ser Asn Gln Lys Asn Tyr
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Ser Leu Leu Asn Ser Ser Asn Gln Lys Asn Tyr
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Ser Leu Leu Ile Ser Ser Asn Gln Asn Asn Tyr
1               5                   10

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Asp Ile Ser Asn Tyr
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Asn Val Gly Thr Asn
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Thr Ile Gly Thr Trp
1               5

<210> SEQ ID NO 10
<211> LENGTH: 6
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 10

Gln Asn Ile Arg Thr Ala
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Asn Val Arg Thr Ala
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Asn Val Arg Thr Ala
1               5

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Ser Leu Leu Tyr Ser Ser Asn Gln Lys Asn Tyr
1               5                   10

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Asn Val Tyr Thr Thr
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Asn Ile Tyr Ser Tyr
1               5
```

```
<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Glu Thr Val Asp Thr Tyr Gly Asn Arg Phe
1               5                   10

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Asp Val Ser Asn Ala
1               5

<210> SEQ ID NO 18
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Ala Ser
1

<210> SEQ ID NO 19
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Tyr Thr Ser
1

<210> SEQ ID NO 20
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Thr Ser
1

<210> SEQ ID NO 21
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 21

Ala Ala Thr
1

<210> SEQ ID NO 22
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Ala Ser
1

<210> SEQ ID NO 23
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Trp Ala Ser
1

<210> SEQ ID NO 24
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Ala Ser
1

<210> SEQ ID NO 25
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Ala Lys
1

<210> SEQ ID NO 26
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ala Ser
1

<210> SEQ ID NO 27
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 27

Cys Gln Gln His Tyr Ser Ile Pro Pro Thr Phe
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Cys Gln Gln His Tyr Ser Ser Pro Pro Thr Phe
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Cys Gln Gln His Tyr Asp Pro Pro Leu Thr Phe
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Gln His His Tyr Asp Pro Pro Leu Thr Phe
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Gln Gln His Tyr Asn Thr Pro Pro Thr Phe
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Cys Gln Gln His Tyr Ser Pro Pro Pro Thr Phe
1               5                   10
```

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Cys Gln Gln His Tyr Ser Thr Pro Pro Thr Phe
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Cys Gln Gln Gly His Thr Leu Pro Tyr Thr Phe
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Cys Gln Gln Gly Asn Thr Leu Pro Tyr Thr Phe
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Cys Gln Gln Tyr Asn Ser Tyr Pro Phe Thr Phe
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Cys Gln Gln Leu Tyr Ser Thr Pro Leu Thr Phe
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 38

Cys Leu Gln His Trp Asn Tyr Pro Phe Thr Phe
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Cys Gln Gln Tyr Tyr Ser Tyr Arg Thr Phe
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Gln Gln Tyr Asn Ser Tyr Pro Tyr Thr Phe
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Cys Gln His His Tyr Gly Phe Pro Tyr Thr Phe
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Cys Gln Gln Ser Asn Glu Asp Pro Phe Thr Phe
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Cys Pro Gln His Tyr Ser Thr Leu Cys Thr Phe
1               5                   10

<210> SEQ ID NO 44
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Tyr Thr Phe Thr Thr Tyr Gly
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Tyr Met Phe Thr Thr Tyr Gly
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Tyr Thr Phe Thr Asn Tyr Gly
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Tyr Ser Ile Thr Ser Gly His Tyr
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Phe Ser Phe Ser Asp Tyr Gly
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Phe Thr Phe Ser Asp Tyr Gly
```

```
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Tyr Thr Phe Ile Asn Tyr Tyr
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Tyr Thr Phe Ile Ser Tyr Tyr
1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Tyr Thr Phe Thr Ser Tyr Tyr
1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Tyr Thr Phe Thr Ser Tyr Trp
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Phe Ser Leu Thr Asn Tyr Asp
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 55

Gly Tyr Thr Phe Thr Asp Tyr Tyr
1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Asn Val Arg Ser Ala
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Tyr Ser Phe Thr Gly Tyr Thr
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Tyr Thr Phe Thr His Tyr Gly
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Met Asn Thr Tyr Ser Gly Val Pro
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ile Asn Thr Tyr Ser Gly Val Pro
1               5

<210> SEQ ID NO 61

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ile Ser Tyr Asp Gly Asn Asn
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ile Ser Tyr Asp Gly Asn Asp
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ile Ser Ser Gly Ser Ser Thr Ile
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ile Tyr Pro Gly Asn Ile Asn Ser
1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ile Tyr Pro Gly Asn Val Asn Thr
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66
```

```
Ile Trp Thr Gly Gly Asn Thr
1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ile Asp Thr Lys Asn Gly Gly Thr
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Asn Thr Tyr Thr Gly Glu Pro
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ile Asn Pro Tyr Asn Asp Asn Thr
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ile Asn Thr Ser Thr Gly Glu Thr
1               5

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Cys Ala Arg Met Gly Arg Gly Ser Leu Tyr Gly Met Asp Tyr Trp
1               5                   10                  15

<210> SEQ ID NO 72
<211> LENGTH: 16
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 72

Cys Ala Arg Ser Gly His Ser Tyr Ser Leu Tyr Val Met Gly Tyr Trp
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Cys Ala Arg Ser Gly His Asn Tyr Ser Leu Tyr Val Met Gly Tyr Trp
1               5                   10                  15

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Cys Ala Arg Gly Ala Leu Tyr Tyr Phe Asp Asn Trp
1               5                   10

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Cys Ala Arg Ile Gly Asn Thr Asn Ser Leu Tyr Thr Val His Tyr Trp
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Cys Thr Arg Ile Gly Asn Thr Asn Ser Leu Tyr Thr Val His Tyr Trp
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Cys Val Arg Gly Tyr Tyr Tyr Tyr Gly Ser Arg Ala Met Asp Tyr Trp
1               5                   10                  15

```
<210> SEQ ID NO 78
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Cys Val Arg Gly Tyr Tyr Tyr Gly Ser Arg Ala Met Asp Cys Trp
1               5                   10                  15

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Cys Gly Pro Ser Asp Tyr Trp Tyr Phe Asp Val Trp
1               5                   10

<210> SEQ ID NO 80
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Cys Ala Arg Asp Tyr Phe Tyr Gly Asn Asn Tyr Gly Phe Pro Tyr Trp
1               5                   10                  15

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Cys Ala Met Thr Asn Ser Ser Ala Met Asp Tyr Trp
1               5                   10

<210> SEQ ID NO 82
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Cys Val Arg Glu Gly Phe Arg Gln Gly Tyr Tyr Ala Met Asp Tyr Trp
1               5                   10                  15

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83
```

Cys Ala Ser Gly Gly Arg Gly Tyr Trp
1               5

<210> SEQ ID NO 84
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Cys Thr Arg Asn Tyr Tyr Arg Pro Tyr Tyr Ala Met Asp Tyr Trp
1               5                   10                  15

<210> SEQ ID NO 85
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Cys Ala Arg Glu Gly Asn Tyr Tyr Gly Ala Ser Pro Trp Phe Ala Tyr
1               5                   10                  15

Trp

<210> SEQ ID NO 86
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Cys Ala Arg Tyr Tyr Tyr Gly Ser Ser Arg Trp Arg Asp Tyr Trp Phe
1               5                   10                  15

Ala Tyr Trp

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Ser Val Ser Ser Tyr
1               5

<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Ser Val Ser Tyr
1               5

```
<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Ser Val Leu Tyr Ser Ser Asp Gln Lys Asn Tyr
1               5                   10

<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Asp Val Asn Thr Ala
1               5

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gln Ser Leu Val Asn Ser Tyr Gly Ile Thr Tyr
1               5                   10

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ser Ser Val Asn Tyr
1               5

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Asn Ile Asn Val Trp
1               5

<210> SEQ ID NO 94
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94
```

```
Gln Asp Ile Asn Ser Tyr
1               5

<210> SEQ ID NO 95
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Thr Ser
1

<210> SEQ ID NO 96
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asp Thr Ser
1

<210> SEQ ID NO 97
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Ile Ser
1

<210> SEQ ID NO 98
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Lys Ala Ser
1

<210> SEQ ID NO 99
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Ala Asn
1

<210> SEQ ID NO 100
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 100

Cys His Gln Tyr His Arg Ser Pro Phe Thr Phe
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Cys Phe Gln Gly Ser Gly Tyr Pro Phe Thr Phe
1               5                   10

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Cys His Gln Tyr Leu Ser His Thr Phe
1               5

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Cys Gln Gln Leu Tyr Lys Leu Pro Arg Thr Phe
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Cys Leu Gln Gly Thr His Gln Pro Trp Thr Phe
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Cys Gln Gln Phe Ser Ser Ser Pro Tyr Thr Phe
1               5                   10
```

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Cys Gln Gln Trp Arg Ser Tyr Gln Leu Thr Phe
1               5                   10

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Cys Gln Gln Gly Gln Ser Tyr Pro Leu Thr Phe
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Cys Leu Gln Tyr Asp Glu Phe Leu Leu Thr Phe
1               5                   10

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Phe Thr Phe Thr Gly Tyr Trp
1               5

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Phe Ser Leu Asn Thr Phe Asp Met Gly
1               5                   10

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 111

Gly Phe Ser Leu Thr Arg Tyr Gly
1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Tyr Ser Ile Thr Ser Gly Tyr Tyr
1               5

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Tyr Thr Phe Thr Asn Phe Trp
1               5

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Tyr Ser Phe Thr Gly Tyr Phe
1               5

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ile Leu Pro Val Ser Gly Ile Thr
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ile Trp Trp Asp Asp Asp Lys
1               5

<210> SEQ ID NO 117
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 117

Ile Trp Ser Gly Gly Ser Thr
1               5

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Leu Asn Pro Tyr Asn Gly Gly Thr
1               5

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ile Tyr Pro Gly Asn Val Asn Ser
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ile Ser Tyr Asp Gly Ser Asn
1               5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ile His Pro Asn Ser Gly Ser Thr
1               5

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ile Asn Pro Ser Thr Gly Asp Thr
1               5
```

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ile His Pro Asn Gly Gly Ser Thr
1               5

<210> SEQ ID NO 124
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Cys Ala Arg Arg Gly Ser Pro Tyr Phe Asp Tyr Trp
1               5                   10

<210> SEQ ID NO 125
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Cys Gly Arg Lys Pro Gly Gly Tyr Gly Asn Tyr Val Leu
1               5                   10

<210> SEQ ID NO 126
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Cys Ala Arg Asp Gly Arg Val Tyr Ala Met Asp Tyr Trp
1               5                   10

<210> SEQ ID NO 127
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Cys Ala Arg Gly Ser Gly Asn Ser Phe Tyr Ala Met Asp Tyr Trp
1               5                   10                  15

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 128

Cys Thr Ser Ile Tyr Gly Arg Phe Val Tyr Trp
1               5                   10

<210> SEQ ID NO 129
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Cys Ala Arg Asn Ser Gly Asp Tyr Leu Val Tyr Phe Asp Ser Trp
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Cys Ala Arg Gly Ala Thr Val Val Asp Tyr Pro Phe Asp Tyr Trp
1               5                   10                  15

<210> SEQ ID NO 131
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Cys Thr Arg Gly Leu Thr Gly Leu Phe Ala Tyr Trp
1               5                   10

<210> SEQ ID NO 132
<211> LENGTH: 631
<212> TYPE: PRT
<213> ORGANISM: Homo sapiens

<400> SEQUENCE: 132

Met Thr Pro Ala Leu Thr Ala Leu Leu Cys Leu Gly Leu Ser Leu Gly
1               5                   10                  15

Pro Arg Thr Arg Val Gln Ala Gly Pro Phe Pro Lys Pro Thr Leu Trp
                20                  25                  30

Ala Glu Pro Gly Ser Val Ile Ser Trp Gly Ser Pro Val Thr Ile Trp
            35                  40                  45

Cys Gln Gly Ser Leu Glu Ala Gln Glu Tyr Arg Leu Asp Lys Glu Gly
        50                  55                  60

Ser Pro Glu Pro Leu Asp Arg Asn Asn Pro Leu Glu Pro Lys Asn Lys
65                  70                  75                  80

Ala Arg Phe Ser Ile Pro Ser Met Thr Glu His His Ala Gly Arg Tyr
                85                  90                  95

Arg Cys His Tyr Tyr Ser Ser Ala Gly Trp Ser Glu Pro Ser Asp Pro
            100                 105                 110

Leu Glu Leu Val Met Thr Gly Phe Tyr Asn Lys Pro Thr Leu Ser Ala
        115                 120                 125
```

-continued

```
Leu Pro Ser Pro Val Val Ala Ser Gly Gly Asn Met Thr Leu Arg Cys
        130                 135                 140

Gly Ser Gln Lys Gly Tyr His His Phe Val Leu Met Lys Glu Gly Glu
145                 150                 155                 160

His Gln Leu Pro Arg Thr Leu Asp Ser Gln Gln Leu His Ser Gly Gly
                165                 170                 175

Phe Gln Ala Leu Phe Pro Val Gly Pro Val Asn Pro Ser His Arg Trp
                180                 185                 190

Arg Phe Thr Cys Tyr Tyr Tyr Met Asn Thr Pro Gln Val Trp Ser
        195                 200                 205

His Pro Ser Asp Pro Leu Glu Ile Leu Pro Ser Gly Val Ser Arg Lys
    210                 215                 220

Pro Ser Leu Leu Thr Leu Gln Gly Pro Val Leu Ala Pro Gly Gln Ser
225                 230                 235                 240

Leu Thr Leu Gln Cys Gly Ser Asp Val Gly Tyr Asp Arg Phe Val Leu
                245                 250                 255

Tyr Lys Glu Gly Glu Arg Asp Phe Leu Gln Arg Pro Gly Gln Gln Pro
                260                 265                 270

Gln Ala Gly Leu Ser Gln Ala Asn Phe Thr Leu Gly Pro Val Ser Arg
            275                 280                 285

Ser His Gly Gly Gln Tyr Arg Cys Tyr Gly Ala His Asn Leu Ser Ser
    290                 295                 300

Glu Trp Ser Ala Pro Ser Asp Pro Leu Asn Ile Leu Met Ala Gly Gln
305                 310                 315                 320

Ile Tyr Asp Thr Val Ser Leu Ser Ala Gln Pro Gly Pro Thr Val Ala
                325                 330                 335

Ser Gly Glu Asn Val Thr Leu Leu Cys Gln Ser Trp Trp Gln Phe Asp
                340                 345                 350

Thr Phe Leu Leu Thr Lys Glu Gly Ala Ala His Pro Pro Leu Arg Leu
            355                 360                 365

Arg Ser Met Tyr Gly Ala His Lys Tyr Gln Ala Glu Phe Pro Met Ser
    370                 375                 380

Pro Val Thr Ser Ala His Ala Gly Thr Tyr Arg Cys Tyr Gly Ser Tyr
385                 390                 395                 400

Ser Ser Asn Pro His Leu Leu Ser Phe Pro Ser Glu Pro Leu Glu Leu
                405                 410                 415

Met Val Ser Gly His Ser Gly Gly Ser Ser Leu Pro Pro Thr Gly Pro
            420                 425                 430

Pro Ser Thr Pro Gly Leu Gly Arg Tyr Leu Glu Val Leu Ile Gly Val
        435                 440                 445

Ser Val Ala Phe Val Leu Leu Leu Phe Leu Leu Leu Phe Leu Leu Leu
    450                 455                 460

Arg Arg Gln Arg His Ser Lys His Arg Thr Ser Asp Gln Arg Lys Thr
465                 470                 475                 480

Asp Phe Gln Arg Pro Ala Gly Ala Ala Glu Thr Glu Pro Lys Asp Arg
                485                 490                 495

Gly Leu Leu Arg Arg Ser Ser Pro Ala Ala Asp Val Gln Glu Glu Asn
            500                 505                 510

Leu Tyr Ala Ala Val Lys Asp Thr Gln Ser Glu Asp Arg Val Glu Leu
        515                 520                 525

Asp Ser Gln Ser Pro His Asp Glu Asp Pro Gln Ala Val Thr Tyr Ala
530                 535                 540
```

-continued

```
Pro Val Lys His Ser Ser Pro Arg Arg Glu Met Ala Ser Pro Pro Ser
545                 550                 555                 560

Ser Leu Ser Gly Glu Phe Leu Asp Thr Lys Asp Arg Gln Val Glu Glu
            565                 570                 575

Asp Arg Gln Met Asp Thr Glu Ala Ala Ala Ser Glu Ala Ser Gln Asp
        580                 585                 590

Val Thr Tyr Ala Gln Leu His Ser Leu Thr Leu Arg Arg Lys Ala Thr
    595                 600                 605

Glu Pro Pro Ser Gln Glu Gly Glu Pro Pro Ala Glu Pro Ser Ile
610                 615                 620

Tyr Ala Thr Leu Ala Ile His
625                 630

<210> SEQ ID NO 133
<211> LENGTH: 708
<212> TYPE: PRT
<213> ORGANISM: Homo sapiens

<400> SEQUENCE: 133

Met Thr Pro Ala Leu Thr Ala Leu Leu Cys Leu Gly Leu Ser Leu Gly
1               5                   10                  15

Pro Arg Thr Arg Met Gln Ala Gly Pro Phe Pro Lys Pro Thr Leu Trp
            20                  25                  30

Ala Glu Pro Gly Ser Val Ile Ser Trp Gly Ser Pro Val Thr Ile Trp
        35                  40                  45

Cys Gln Gly Ser Leu Glu Ala Gln Glu Tyr Gln Leu Asp Lys Glu Gly
    50                  55                  60

Ser Pro Glu Pro Trp Asp Arg Asn Asn Pro Leu Glu Pro Lys Asn Lys
65                  70                  75                  80

Ala Arg Phe Ser Ile Pro Ser Met Thr Gln His His Ala Gly Arg Tyr
                85                  90                  95

Arg Cys His Tyr Tyr Ser Ser Ala Gly Trp Ser Glu Pro Ser Asp Pro
            100                 105                 110

Leu Glu Leu Val Met Thr Gly Phe Tyr Asn Lys Pro Thr Leu Ser Ala
        115                 120                 125

Leu Pro Ser Pro Val Val Ala Ser Gly Gly Asn Met Thr Leu Arg Cys
    130                 135                 140

Gly Ser Gln Lys Gly Tyr His His Phe Val Leu Met Lys Glu Gly Glu
145                 150                 155                 160

His Gln Leu Pro Arg Thr Leu Asp Ser Gln Gln Leu His Ser Gly Gly
                165                 170                 175

Phe Gln Ala Leu Phe Pro Val Gly Pro Val Thr Pro Ser His Arg Trp
            180                 185                 190

Arg Phe Thr Cys Tyr Tyr Tyr Thr Asn Thr Pro Trp Val Trp Ser
        195                 200                 205

His Pro Ser Asp Pro Leu Glu Ile Leu Pro Ser Gly Val Ser Arg Lys
    210                 215                 220

Pro Ser Leu Leu Thr Leu Gln Gly Pro Val Leu Ala Pro Gly Gln Ser
225                 230                 235                 240

Leu Thr Leu Gln Cys Gly Ser Asp Val Gly Tyr Asp Arg Phe Val Leu
                245                 250                 255

Tyr Lys Glu Gly Glu Arg Asp Phe Leu Gln Arg Pro Gly Gln Gln Pro
            260                 265                 270

Gln Ala Gly Leu Ser Gln Ala Asn Phe Thr Leu Gly Pro Val Ser Arg
        275                 280                 285
```

```
Ser Tyr Gly Gly Gln Tyr Arg Cys Tyr Gly Ala His Asn Leu Ser Ser
    290                 295                 300

Glu Trp Ser Ala Pro Ser Asp Pro Leu Asp Ile Leu Ile Thr Gly Gln
305                 310                 315                 320

Ile Tyr Asp Thr Val Ser Leu Ser Ala Gln Pro Gly Pro Thr Val Ala
                325                 330                 335

Ser Gly Glu Asn Met Thr Leu Leu Cys Gln Ser Arg Gly Tyr Phe Asp
                340                 345                 350

Thr Phe Leu Leu Thr Lys Glu Gly Ala Ala His Pro Pro Leu Arg Leu
            355                 360                 365

Arg Ser Met Tyr Gly Ala His Lys Tyr Gln Ala Glu Phe Pro Met Ser
370                 375                 380

Pro Val Thr Ser Ala His Ala Gly Thr Tyr Arg Cys Tyr Gly Ser Arg
385                 390                 395                 400

Ser Ser Asn Pro His Leu Leu Ser Phe Pro Ser Glu Pro Leu Glu Leu
                405                 410                 415

Met Val Ser Gly His Ser Gly Gly Ser Ser Leu Pro Pro Thr Gly Pro
                420                 425                 430

Pro Ser Thr Pro Gly Leu Gly Arg Tyr Leu Glu Val Leu Ile Gly Val
            435                 440                 445

Ser Val Ala Phe Val Leu Leu Leu Phe Leu Leu Leu Phe Leu Leu Leu
450                 455                 460

Leu Arg Gln Arg His Ser Lys His Arg Thr Ser Asp Gln Arg Lys Thr
465                 470                 475                 480

Asp Phe Gln Arg Pro Ala Gly Ala Ala Glu Thr Glu Pro Lys Asp Arg
                485                 490                 495

Gly Leu Leu Arg Arg Ser Ser Pro Ala Ala Asp Val Gln Glu Glu Asn
            500                 505                 510

Leu Cys Lys Arg Lys Arg Gly Asp Lys Trp Gly Cys Trp Arg Asp Arg
        515                 520                 525

Ser Pro Lys Ile Ser Val Ala Thr Gly Arg Gly Trp Glu Gly Ser Gly
    530                 535                 540

Ala Pro Trp Lys Met Val Leu Pro His Thr Val Gly Pro Pro Cys Ile
545                 550                 555                 560

Arg Trp Pro His Leu Gly Ala Gly Gln Gly Ala Ser Arg Thr Glu Arg
                565                 570                 575

Ser Gln Arg Thr Arg Arg Thr Pro Cys Ser Ala Pro Ala Asp Ala
                580                 585                 590

Ala Val Lys Asp Thr Gln Ser Glu Asp Arg Val Glu Leu Asp Ser Gln
            595                 600                 605

Ser Pro His Asp Glu Asp Pro Gln Ala Val Thr Tyr Ala Pro Val Lys
610                 615                 620

His Ser Ser Pro Arg Arg Glu Met Ala Ser Pro Ser Ser Leu Ser
625                 630                 635                 640

Gly Glu Phe Leu Asp Thr Lys Asp Arg Gln Val Glu Glu Asp Arg Gln
                645                 650                 655

Met Asp Thr Glu Ala Ala Ala Ser Glu Ala Ser Gln Asp Val Thr Tyr
                660                 665                 670

Ala Gln Leu His Ser Leu Thr Leu Arg Arg Lys Ala Thr Glu Pro Pro
            675                 680                 685

Pro Ser Gln Glu Gly Glu Pro Ala Glu Pro Ser Ile Tyr Ala Thr
            690                 695                 700
```

Leu Ala Ile His
705

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Glu Ser Val Leu Ile Ile Asp Thr Asn Leu
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Glu Ser Val Thr Ile Ile Asp Thr His Leu
1               5                   10

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gln Asn Val Gly Thr Ala
1               5

<210> SEQ ID NO 137
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gln Ser Leu Val His Ser Asn Gly Asn Thr Tyr
1               5                   10

<210> SEQ ID NO 138
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gln Ser Leu Val His Ser Asn Gly Tyr Thr Tyr
1               5                   10

<210> SEQ ID NO 139
<211> LENGTH: 6
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 139

Gln Asn Val Gly Ser Ala
1               5

<210> SEQ ID NO 140
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Arg Asp Ile Asn Gly Tyr
1               5

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ser Ser Val Ser Ser Gly Tyr
1               5

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ser Ser Val Ser Ser Thr Tyr
1               5

<210> SEQ ID NO 143
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gln Ser Leu Val His Ser Asn Gly Asp Thr Cys
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gln Ser Leu Leu Tyr Ser Ser Tyr Gln Lys Asn Tyr
1               5                   10
```

```
<210> SEQ ID NO 145
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gln Gly Ile Ser Asn Tyr
1               5

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Glu Asn Val Asp Arg Phe Gly His Asn Phe
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Glu Ser Val Asp Ser Tyr Gly Asn Ser Phe
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Lys Ser Val Ser Ser Gly Tyr Ser Tyr
1               5                   10

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ser Ser Leu Ser Ser Ser Tyr
1               5

<210> SEQ ID NO 150
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150
```

```
Glu Asn Ile Tyr Ser Asn
1               5

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gln Ser Val Thr Thr Ser Asp Tyr Ser Tyr
1               5                   10

<210> SEQ ID NO 152
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Lys Asn Ile Tyr Ser Asn
1               5

<210> SEQ ID NO 153
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gln Ser Leu Leu Asp Ser Asp Gly Lys Thr Tyr
1               5                   10

<210> SEQ ID NO 154
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gln Asp Ile Ser Asp Tyr
1               5

<210> SEQ ID NO 155
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gln Ser Leu Leu Asn Asn Ser Asn Gln Lys Asn Tyr
1               5                   10

<210> SEQ ID NO 156
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 156

His Asn Val Arg Thr Ala
1               5

<210> SEQ ID NO 157
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

His Ala Ser
1

<210> SEQ ID NO 158
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

His Ser Ser
1

<210> SEQ ID NO 159
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ala Thr Ser
1

<210> SEQ ID NO 160
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Lys Val Ser
1

<210> SEQ ID NO 161
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Thr Thr Ser
1
```

```
<210> SEQ ID NO 162
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Asn Val Lys
1

<210> SEQ ID NO 163
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Leu Val Ser
1

<210> SEQ ID NO 164
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Cys Leu Gln Ser Arg Lys Ile Pro Pro Thr Phe
1               5                   10

<210> SEQ ID NO 165
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Cys Gln Gln Trp Asn Thr Asn Pro Tyr Thr Phe
1               5                   10

<210> SEQ ID NO 166
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Cys Gln Gln Tyr Ser Ser Ser Pro Leu Thr Phe
1               5                   10

<210> SEQ ID NO 167
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 167

Cys Gln Gln Tyr Asn Gly Tyr Pro Tyr Thr Phe
1               5                   10

<210> SEQ ID NO 168
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Cys Ser Gln Ser Thr His Val Pro Trp Thr Phe
1               5                   10

<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Cys Ser Gln Ser Thr His Val Pro Tyr Thr Phe
1               5                   10

<210> SEQ ID NO 170
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Cys Gln Gln Tyr Thr Ser Tyr Pro Tyr Thr Phe
1               5                   10

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Cys His Gln Phe His Arg Ser Pro Phe Thr Phe
1               5                   10

<210> SEQ ID NO 172
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Cys His Gln Tyr His Arg Ser Pro Tyr Thr Phe
1               5                   10

<210> SEQ ID NO 173
<211> LENGTH: 11
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 173

Cys Gln Gln Tyr Tyr Asn Tyr Pro Trp Thr Phe
1               5                   10

<210> SEQ ID NO 174
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Cys Gln Gln Tyr Ser Lys Leu Pro Pro Thr Phe
1               5                   10

<210> SEQ ID NO 175
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Cys Gln Gln Gly Lys Thr Leu Pro Trp Thr Phe
1               5                   10

<210> SEQ ID NO 176
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Cys Gln Gln His Tyr Ser Thr Pro Leu Thr Phe
1               5                   10

<210> SEQ ID NO 177
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Cys Gln Gln Ala Asn Thr Leu Pro Trp Thr Phe
1               5                   10

<210> SEQ ID NO 178
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Cys Gln Gln Phe Ser Lys Phe Pro Trp Thr Phe
1               5                   10

<210> SEQ ID NO 179
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Cys Gln His His Tyr Gly Pro Pro Pro Thr Phe
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Cys Gln Gln Ser Asn Glu Asp Pro Pro Thr Phe
1               5                   10

<210> SEQ ID NO 181
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Cys Gln Gln Cys Asn Glu Asp Pro Trp Thr Phe
1               5                   10

<210> SEQ ID NO 182
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Cys Gln His Ile Arg Glu Leu Pro Trp Thr Phe
1               5                   10

<210> SEQ ID NO 183
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Cys Gln His Phe Trp Gly Thr Pro Tyr Thr Phe
1               5                   10

<210> SEQ ID NO 184
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Cys Gln Gln Ser Asn Glu Asp Pro Leu Thr Phe
1               5                   10

<210> SEQ ID NO 185
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Cys Gln Asn Ser Arg Glu Cys Pro Ser Trp Phe
1               5                   10

<210> SEQ ID NO 186
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Cys Gln His Phe Trp Gly Ser Pro Tyr Thr Phe
1               5                   10

<210> SEQ ID NO 187
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Cys Gln His Phe Trp Gly Thr Pro Leu Thr Phe
1               5                   10

<210> SEQ ID NO 188
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Cys Trp Gln Gly Thr His Leu Tyr Thr Phe
1               5                   10

<210> SEQ ID NO 189
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Cys Gln Gln Phe Ser Lys Leu Pro Trp Thr Phe
1               5                   10

<210> SEQ ID NO 190
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gly Phe Ser Leu Thr Ser Tyr Gly
1               5

<210> SEQ ID NO 191
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gly Tyr Thr Phe Thr Asp His Thr
1               5

<210> SEQ ID NO 192
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gly Tyr Thr Phe Asn Ser Tyr Trp
1               5

<210> SEQ ID NO 193
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gly Tyr Ala Phe Ser Ser Ser Trp
1               5

<210> SEQ ID NO 194
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Gly Phe Thr Phe Ile Asp Phe Gly
1               5

<210> SEQ ID NO 195
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gly Phe Thr Phe Ser Asp Phe Gly
```

```
<210> SEQ ID NO 196
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gly Tyr Thr Phe Thr Thr Tyr Pro
1               5

<210> SEQ ID NO 197
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gly Tyr Thr Phe Thr Gly Asn Trp
1               5

<210> SEQ ID NO 198
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gly Tyr Thr Phe Thr Gly Tyr Trp
1               5

<210> SEQ ID NO 199
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gly Tyr Thr Phe Thr Gly Asp Trp
1               5

<210> SEQ ID NO 200
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Phe Asn Ile Lys Asp Tyr Tyr
1               5

<210> SEQ ID NO 201
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 201

Gly Phe Ser Leu Thr Asn Tyr Gly
1               5

<210> SEQ ID NO 202
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Gly Phe Thr Phe Ser Ser Tyr Ala
1               5

<210> SEQ ID NO 203
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Trp Leu His Leu His Lys Leu Leu
1               5

<210> SEQ ID NO 204
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Gly Phe Ser Leu Ser Ser Tyr Gly
1               5

<210> SEQ ID NO 205
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gly Tyr Ser Ile Thr Asp Tyr Thr
1               5

<210> SEQ ID NO 206
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Tyr Thr Phe Thr Asp Tyr Asn
1               5

<210> SEQ ID NO 207

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Gly Tyr Thr Phe Ile Ser Tyr Phe
1               5

<210> SEQ ID NO 208
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gly Phe Ser Leu Ser Thr Phe Gly Met Gly
1               5                   10

<210> SEQ ID NO 209
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Phe Ser Phe Ser Asp Tyr Tyr
1               5

<210> SEQ ID NO 210
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gly Phe Thr Phe Ser Asp Tyr Tyr
1               5

<210> SEQ ID NO 211
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gly Asp Ser Ile Thr Ser Gly His
1               5

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212
```

```
Gly Tyr Ser Ile Thr Ser Gly Ser Tyr
1               5

<210> SEQ ID NO 213
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gly Tyr Thr Phe Ser Ser Tyr Trp
1               5

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gly Phe Thr Phe Ser Asp Ala Trp
1               5

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ile Trp Gly Asp Gly Ser Thr
1               5

<210> SEQ ID NO 216
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ile Tyr Pro Lys Asp Gly Tyr Thr
1               5

<210> SEQ ID NO 217
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ile Tyr Pro Gly Ser Gly Ser Thr
1               5

<210> SEQ ID NO 218
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 218

Ile Tyr Pro Gly Asp Gly Asp Thr
1               5

<210> SEQ ID NO 219
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ile Ser Ser Gly Ser Ser Thr Val
1               5

<210> SEQ ID NO 220
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Phe His Pro Phe Asn Asp Tyr Ser
1               5

<210> SEQ ID NO 221
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Ile Leu Ala Arg Ser Gly Asn Ile
1               5

<210> SEQ ID NO 222
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ile Leu Pro Gly Ser Ile Tyr Ile
1               5

<210> SEQ ID NO 223
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Ile Leu Pro Gly Ile Gly Tyr Thr
1               5
```

```
<210> SEQ ID NO 224
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ile Asp Ala Ile Asp Gly Glu Thr
1               5

<210> SEQ ID NO 225
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ile Ser Ser Gly Gly Asp Tyr Ile
1               5

<210> SEQ ID NO 226
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Ile Trp Ala Gly Lys Ile Thr
1               5

<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ile Trp Ala Gly Gly Ile Thr
1               5

<210> SEQ ID NO 228
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ile Asn Thr Asn Thr Gly Glu Pro
1               5

<210> SEQ ID NO 229
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229
```

```
Ile Asn Pro Tyr Asn Gly Arg Thr
1               5

<210> SEQ ID NO 230
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ile Tyr Trp Asp Asp Asp Lys
1               5

<210> SEQ ID NO 231
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Ile Ser Asp Gly Gly Asp Tyr Thr
1               5

<210> SEQ ID NO 232
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Ile Ser Tyr Asp Gly Thr Asn
1               5

<210> SEQ ID NO 233
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ile Ser Asp Gly Gly Asn Tyr Thr
1               5

<210> SEQ ID NO 234
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ile Tyr Pro Tyr Asn Gly Gly Thr
1               5

<210> SEQ ID NO 235
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 235

Ile Ser Tyr Ser Gly Ser Thr
1               5

<210> SEQ ID NO 236
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ile Leu Pro Gly Thr Gly Asp Ser
1               5

<210> SEQ ID NO 237
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ile Arg Ser Lys Ala His Asn His Val Thr
1               5                   10

<210> SEQ ID NO 238
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ile Trp Ala Gly Gly Asn Thr
1               5

<210> SEQ ID NO 239
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Cys Ala Arg Arg Ala Tyr Tyr Gly Thr Ser His Phe Asp Tyr Trp
1               5                   10                  15

<210> SEQ ID NO 240
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Cys Ala Lys Pro Asn Trp Asp Tyr Tyr Ala Met Asp Tyr Trp
1               5                   10
```

<210> SEQ ID NO 241
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Cys Ala Arg Thr Trp Asp Tyr Phe Asp Tyr Trp
1               5                   10

<210> SEQ ID NO 242
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Cys Ala Arg Arg Phe Arg Asp Tyr Tyr Gly Thr Val Phe Ala Asp Tyr
1               5                   10                  15

Trp

<210> SEQ ID NO 243
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Cys Ala Arg Gly Leu Gly Arg Arg Trp Phe Phe Asp Val Trp
1               5                   10

<210> SEQ ID NO 244
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Cys Ser Arg Glu Gly Asp Tyr Tyr Gly His Phe Glu Tyr Trp
1               5                   10                  15

<210> SEQ ID NO 245
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Cys Ala Arg Pro Glu Leu Pro Tyr Tyr Tyr Ala Met Asp Tyr Trp
1               5                   10                  15

<210> SEQ ID NO 246
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 246

Cys Ala Arg Pro Gly Leu Pro Tyr Tyr Tyr Ala Met Asp Tyr Trp
1               5                   10                  15

<210> SEQ ID NO 247
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Cys Ala Arg Leu Ser Asn Tyr Gly Ala Trp Phe Pro Tyr Trp
1               5                   10

<210> SEQ ID NO 248
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Cys Ala Arg Gly Leu Thr Gly Leu Phe Ala Tyr Trp
1               5                   10

<210> SEQ ID NO 249
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Cys Ala Lys Arg Arg Leu Leu Ala Met Asp Asp Trp
1               5                   10

<210> SEQ ID NO 250
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Cys Ala Lys Arg Arg Leu Leu Ser Met Asp Tyr Trp
1               5                   10

<210> SEQ ID NO 251
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Cys Ala Arg Arg Leu Phe Tyr Tyr Phe Asp Tyr Trp
1               5                   10

<210> SEQ ID NO 252

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Cys Gly Arg Gly Ala Leu Phe Ile Thr Thr Ser Leu Asp Tyr Trp
1               5                   10                  15

<210> SEQ ID NO 253
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Cys Ala Arg Glu Gly Asp Tyr Tyr Tyr Gly His Phe Asp Tyr Trp
1               5                   10                  15

<210> SEQ ID NO 254
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Cys Gly Lys Pro Asn Trp Asp Tyr Tyr Ala Met Asp Tyr Trp
1               5                   10

<210> SEQ ID NO 255
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Cys Ala Ser Asp Gly Tyr Pro Tyr Gly Met Asp Tyr Trp
1               5                   10

<210> SEQ ID NO 256
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Cys Thr Arg Asp Arg Lys Glu Pro Tyr Asp Ser Ser Tyr Arg Tyr Ala
1               5                   10                  15

Met Asp Tyr Trp
            20

<210> SEQ ID NO 257
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 257

Cys Ala Arg Gly Gly Asp Tyr Tyr Gly Ser Trp Tyr Phe Asp Val
1               5                   10                  15
Trp

<210> SEQ ID NO 258
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Cys Ala Arg Asp Arg Gly Ser Ser Gly Ser Tyr Tyr Ala Met Asp Tyr
1               5                   10                  15
Trp

<210> SEQ ID NO 259
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Cys Ala Arg Gly Gly Tyr Ser Gly Tyr Leu Tyr Tyr Phe Asp Tyr Trp
1               5                   10                  15

<210> SEQ ID NO 260
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Cys Ala Arg Gly Gly Asp Tyr Tyr Gly Ser Tyr Tyr Tyr Phe Asp Tyr
1               5                   10                  15
Trp

<210> SEQ ID NO 261
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Cys Ala Arg Ser Tyr Ala Asn Pro Tyr Tyr Ala Met Asp Tyr Trp
1               5                   10                  15

<210> SEQ ID NO 262
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Cys Ala Val Thr Asn Ser Ser Ala Met Asp Phe Trp
1               5                   10

<210> SEQ ID NO 263
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Cys Ala Arg Ile Thr Glu Thr Ala Met Asp Tyr Trp
1               5                   10

<210> SEQ ID NO 264
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Cys Ala Arg Asp Arg His Ser Gly Thr Tyr Ala Met Asp Tyr Trp
1               5                   10                  15

<210> SEQ ID NO 265
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Cys Ala Arg Glu Arg Gly Ile Tyr Ser Gly Asn Tyr Val Tyr Tyr Phe
1               5                   10                  15

Asp Tyr Trp

<210> SEQ ID NO 266
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Cys Ala Arg Glu Thr Leu Pro Ser Tyr Tyr Ala Met Asp Tyr Trp
1               5                   10                  15

<210> SEQ ID NO 267
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Cys Ala Arg Asn Asp Glu Gly Asp Ser Leu Thr Val Tyr Tyr Phe Val
1               5                   10                  15

Met Asp Tyr Trp
            20

```
<210> SEQ ID NO 268
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Cys Ala Arg Ser Arg Tyr Asp Gly Tyr Tyr Pro Ala Trp Leu Ala Tyr
1               5                   10                  15

Trp

<210> SEQ ID NO 269
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Cys Thr Arg Glu Arg Glu Ile Tyr Ser Gly Asn Tyr Val Tyr Phe Phe
1               5                   10                  15

Asp Tyr Trp

<210> SEQ ID NO 270
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Cys Thr Arg Ser Lys Arg Tyr Gly Asn Tyr Tyr Ala Met Asp Tyr Trp
1               5                   10                  15

<210> SEQ ID NO 271
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Cys Thr Arg Thr Thr Gly Tyr Ala Met Asp Tyr Trp
1               5                   10

<210> SEQ ID NO 272
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Cys Val Arg Asp Arg Gly Thr Ala Arg Ala Tyr Tyr Ala Met Asp Tyr
1               5                   10                  15

Trp
```